United States Patent
Ortiz et al.

(10) Patent No.: US 11,849,934 B2
(45) Date of Patent: Dec. 26, 2023

(54) SURGICAL ACCESS DEVICES AND METHODS PROVIDING SEAL MOVEMENT IN PREDEFINED MOVEMENT REGIONS

(71) Applicant: Cilag GmbH International, Zug (CH)

(72) Inventors: Mark S. Ortiz, Milford, OH (US); David T. Martin, Milford, OH (US); Matthew C. Miller, Cincinnati, OH (US); Mark J. Reese, Cincinnati, OH (US); Wells D. Haberstich, Loveland, OH (US); Carl Shurtleff, Mason, OH (US); Charles J. Scheib, Loveland, OH (US); Frederick E. Shelton, IV, Hillsboro, OH (US); Jerome R. Morgan, Cincinnati, OH (US); Daniel H. Duke, Franklin, OH (US); Daniel J. Mumaw, Cincinnati, OH (US); Gregory W. Johnson, Milford, OH (US); Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 320 days.

(21) Appl. No.: 17/065,924

(22) Filed: Oct. 8, 2020

(65) Prior Publication Data
US 2021/0022724 A1 Jan. 28, 2021

Related U.S. Application Data

(63) Continuation of application No. 16/213,587, filed on Dec. 7, 2018, now Pat. No. 10,813,632, which is a
(Continued)

(51) Int. Cl.
*A61B 17/02* (2006.01)
*A61B 17/34* (2006.01)
*A61M 13/00* (2006.01)

(52) U.S. Cl.
CPC ...... *A61B 17/0293* (2013.01); *A61B 17/0218* (2013.01); *A61B 17/3423* (2013.01);
(Continued)

(58) Field of Classification Search
CPC ..... A61B 17/02; A61B 17/0293; A61B 17/34; A61B 17/3421–3431; A61B 17/3462; A61B 2017/3464–3466; A61B 2017/347
See application file for complete search history.

(56) References Cited

U.S. PATENT DOCUMENTS 3,402,710 A 9/1968 Paleschuck
3,654,965 A 4/1972 Gramain
(Continued)

FOREIGN PATENT DOCUMENTS

EP 0568383 A1 11/1993
EP 0646358 A1 4/1995
(Continued)

OTHER PUBLICATIONS

[No Author Listed] Product Brochure "Access the Future of Laparoscopic Surgery" Advanced Surgical Concepts Limited, Inc.
(Continued)

*Primary Examiner* — Eduardo C Robert
*Assistant Examiner* — Michelle C Eckman
(74) *Attorney, Agent, or Firm* — Mintz Levin Cohn Ferris Glovsky and Popeo, P.C.

(57) ABSTRACT

Various methods and devices are provided for allowing multiple surgical instruments to be inserted into sealing elements of a single surgical access device. The sealing elements can be movable along predefined pathways within the device to allow surgical instruments inserted through the sealing elements to be moved laterally, rotationally, angularly, and vertically relative to a central longitudinal axis of
(Continued)

the device for ease of manipulation within a patient's body while maintaining insufflation.

18 Claims, 37 Drawing Sheets

Related U.S. Application Data continuation of application No. 15/369,220, filed on Dec. 5, 2016, now Pat. No. 10,182,805, which is a continuation of application No. 14/594,535, filed on Jan. 12, 2015, now Pat. No. 9,538,997, which is a continuation of application No. 12/399,656, filed on Mar. 6, 2009, now Pat. No. 8,961,406.

(52) U.S. Cl.
CPC ...... *A61B 17/3462* (2013.01); *A61B 17/3474* (2013.01); *A61M 13/003* (2013.01); *A61B 2017/0225* (2013.01); *A61B 2017/3419* (2013.01); *A61B 2017/3445* (2013.01); *A61B 2017/3447* (2013.01); *A61B 2017/3466* (2013.01)

(56) References Cited

U.S. PATENT DOCUMENTS

| | | | |
|---|---|---|---|
| 4,112,932 A | 9/1978 | Chiulli | |
| 4,306,545 A | 12/1981 | Ivan et al. | |
| 2,129,391 A | 9/1983 | Frederick | |
| 4,402,683 A | 9/1983 | Kopman | |
| 4,417,888 A | 11/1983 | Cosentino et al. | |
| 5,183,464 A | 2/1993 | Dubrul et al. | |
| 5,183,471 A | 2/1993 | Wilk | |
| 5,197,955 A | 3/1993 | Stephens et al. | |
| 5,207,213 A | 5/1993 | Auhll et al. | |
| 5,209,737 A | 5/1993 | Ritchart et al. | |
| 5,209,741 A | 5/1993 | Spaeth | |
| 5,269,772 A | 12/1993 | Wilk | |
| 5,285,945 A | 2/1994 | Brinkerhoff et al. | |
| 5,308,336 A | 5/1994 | Hart et al. | |
| 5,320,611 A | 6/1994 | Bonutti et al. | |
| 5,330,437 A | 7/1994 | Durman | |
| 5,366,478 A | 11/1994 | Brinkerhoff et al. | |
| 5,375,588 A | 12/1994 | Yoon | |
| 5,385,553 A | 1/1995 | Hart et al. | |
| 5,385,560 A | 1/1995 | Wulf | |
| 5,391,154 A | 2/1995 | Young | |
| 5,395,367 A | 3/1995 | Wilk | |
| 5,431,676 A | 7/1995 | Dubrul et al. | |
| 5,443,452 A | 8/1995 | Hart et al. | |
| 5,443,484 A | 8/1995 | Kirsch et al. | |
| 5,480,410 A | 1/1996 | Cuschieri et al. | |
| 5,492,304 A | 2/1996 | Smith et al. | |
| 5,496,280 A | 3/1996 | Vandenbroek et al. | |
| 5,545,179 A | 8/1996 | Williamson, IV | |
| 5,569,205 A | 10/1996 | Hart et al. | |
| 5,569,254 A | 10/1996 | Carlson et al. | |
| 5,584,850 A | 12/1996 | Hart et al. | |
| 5,634,911 A | 6/1997 | Hermann et al. | |
| 5,634,937 A | 6/1997 | Mollenauer et al. | |
| 5,643,301 A | 7/1997 | Mollenauer | |
| 5,653,705 A | 8/1997 | de la Torre et al. | |
| 5,658,272 A | 8/1997 | Hasson | |
| 5,672,168 A | 9/1997 | de la Torre et al. | |
| 5,676,657 A | 10/1997 | Yoon | |
| 5,695,448 A | 12/1997 | Kimura et al. | |
| 5,752,970 A | 5/1998 | Yoon | |
| 5,814,058 A | 9/1998 | Carlson et al. | |
| 5,827,319 A | 10/1998 | Carlson et al. | |
| 5,865,807 A | 2/1999 | Blake, III | |
| 5,891,013 A | 4/1999 | Thompson | |
| 5,906,577 A | 5/1999 | Beane et al. | |
| 5,951,466 A | 9/1999 | Segermark et al. | |
| 5,957,913 A | 9/1999 | de la Torre et al. | |
| 5,990,382 A | 11/1999 | Fox | |
| 5,997,515 A | 12/1999 | de la Torre et al. | |
| 6,004,303 A | 12/1999 | Peterson | |
| 6,024,736 A | 2/2000 | de la Torre et al. | |
| 6,066,090 A | 5/2000 | Yoon | |
| 6,077,288 A | 6/2000 | Shimomura et al. | |
| 6,086,603 A | 7/2000 | Termin et al. | |
| 6,120,513 A | 9/2000 | Bailey et al. | |
| 6,123,689 A | 9/2000 | To et al. | |
| 6,162,196 A | 12/2000 | Hart et al. | |
| 6,217,555 B1 | 4/2001 | Hart et al. | |
| 6,245,052 B1 | 6/2001 | Orth et al. | |
| 6,258,069 B1 | 7/2001 | Carpentier et al. | |
| 6,277,064 B1 | 8/2001 | Yoon | |
| 6,315,770 B1 | 11/2001 | de la Torre et al. | |
| 6,319,246 B1 | 11/2001 | de la Torre et al. | |
| 6,328,730 B1 | 12/2001 | Harkrider, Jr. | |
| 6,348,034 B1 | 2/2002 | Thompson | |
| 6,352,503 B1 | 3/2002 | Matsui et al. | |
| 6,382,211 B1 | 5/2002 | Crook | |
| 6,440,061 B1 | 8/2002 | Wenner et al. | |
| 6,447,489 B1 | 9/2002 | Peterson | |
| 6,454,783 B1 | 9/2002 | Piskun | |
| 6,458,077 B1 | 10/2002 | Boebel et al. | |
| 6,551,270 B1 | 4/2003 | Bimbo et al. | |
| 6,551,282 B1 | 4/2003 | Exline et al. | |
| 6,589,167 B1 | 7/2003 | Shimomura et al. | |
| 6,605,063 B2 | 8/2003 | Bousquet | |
| 6,613,038 B2 | 9/2003 | Bonutti et al. | |
| 6,669,674 B1 | 12/2003 | Macoviak et al. | |
| 6,702,787 B2 | 3/2004 | Racenet et al. | |
| 6,706,033 B1 | 3/2004 | Martinez et al. | |
| 6,706,050 B1 | 3/2004 | Giannadakis | |
| 6,807,965 B1 | 10/2004 | Hickle | |
| 6,905,057 B2 | 6/2005 | Swayze et al. | |
| 6,908,430 B2 | 6/2005 | Caldwell et al. | |
| 6,939,296 B2 | 9/2005 | Ewers et al. | |
| 6,945,932 B1 | 9/2005 | Caldwell et al. | |
| 6,972,026 B1 | 12/2005 | Caldwell et al. | |
| 7,014,628 B2 | 3/2006 | Bousquet | |
| 7,052,454 B2 | 5/2006 | Taylor | |
| 7,083,626 B2 | 8/2006 | Hart et al. | |
| 7,118,528 B1 | 10/2006 | Piskun | |
| 7,153,261 B2 | 12/2006 | Wenchell | |
| 7,163,510 B2 | 1/2007 | Kahle et al. | |
| 7,201,734 B2 | 4/2007 | Hickle | |
| 7,214,185 B1 | 5/2007 | Rosney et al. | |
| 7,247,154 B2 | 7/2007 | Hickle | |
| 7,338,473 B2 | 3/2008 | Campbell et al. | |
| 7,344,547 B2 | 3/2008 | Piskun | |
| 7,393,322 B2 | 7/2008 | Wenchell | |
| 7,413,559 B2 | 8/2008 | Stubbs et al. | |
| 7,850,600 B1 | 12/2010 | Piskun | |
| 8,206,294 B2 | 6/2012 | Widenhouse et al. | |
| 8,251,900 B2 | 8/2012 | Ortiz et al. | |
| 8,361,109 B2 | 1/2013 | Cropper et al. | |
| 8,721,536 B2 | 5/2014 | Marino et al. | |
| D720,068 S | 12/2014 | Oberlaender | |
| 8,961,406 B2* | 2/2015 | Ortiz | A61B 17/3474 600/206 |
| 9,538,997 B2* | 1/2017 | Ortiz | A61B 17/3474 |
| 9,707,011 B2 | 7/2017 | Malkowski et al. | |
| 10,182,805 B2* | 1/2019 | Ortiz | A61M 13/003 |
| 10,813,632 B2* | 10/2020 | Ortiz | A61B 17/3423 |
| 2002/0042606 A1 | 4/2002 | Castaneda et al. | |
| 2002/0156432 A1 | 10/2002 | Racenet et al. | |
| 2003/0028179 A1 | 2/2003 | Piskun | |
| 2003/0040753 A1 | 2/2003 | Daum et al. | |
| 2003/0139756 A1 | 7/2003 | Brustad | |
| 2004/0015185 A1 | 1/2004 | Ewers et al. | |
| 2004/0106942 A1 | 6/2004 | Taylor et al. | |
| 2004/0138528 A1 | 7/2004 | Richter et al. | |
| 2004/0167543 A1 | 8/2004 | Mazzocchi et al. | |
| 2004/0199181 A1 | 10/2004 | Knodel et al. | |
| 2004/0215063 A1 | 10/2004 | Bonadio et al. | |
| 2004/0230160 A1 | 11/2004 | Blanco | |
| 2004/0230161 A1 | 11/2004 | Zeiner | |

(56) References Cited

U.S. PATENT DOCUMENTS

| | | |
|---|---|---|
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0070946 A1 | 3/2005 | Franer et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0024500 A1 | 2/2006 | Seo |
| 2006/0071432 A1 | 4/2006 | Staudner |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247500 A1 | 11/2006 | Voegele et al. |
| 2006/0247673 A1 | 11/2006 | Voegele et al. |
| 2006/0253077 A1 | 11/2006 | Smith |
| 2006/0264706 A1 | 11/2006 | Piskun |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0118021 A1 | 5/2007 | Pokorney |
| 2007/0151566 A1 | 7/2007 | Kahle et al. |
| 2007/0185453 A1 | 8/2007 | Michael et al. |
| 2007/0208312 A1 | 9/2007 | Norton et al. |
| 2007/0255218 A1 | 11/2007 | Franer |
| 2007/0255219 A1 | 11/2007 | Vaugh et al. |
| 2007/0260121 A1 | 11/2007 | Bakos et al. |
| 2007/0260273 A1 | 11/2007 | Cropper et al. |
| 2008/0027476 A1 | 1/2008 | Piskun |
| 2008/0051739 A1 | 2/2008 | McFarlane |
| 2008/0065021 A1 | 3/2008 | Jenkins et al. |
| 2008/0119821 A1 | 5/2008 | Agnihotri et al. |
| 2008/0255519 A1 | 10/2008 | Piskun et al. |
| 2009/0005799 A1 | 1/2009 | Franer et al. |
| 2009/0036745 A1 | 2/2009 | Bonadio et al. |
| 2009/0093683 A1 | 4/2009 | Richard et al. |
| 2009/0093752 A1 | 4/2009 | Richard et al. |
| 2009/0187079 A1 | 7/2009 | Albrecht et al. |
| 2009/0221966 A1* | 9/2009 | Richard ............ A61B 17/3421 604/164.04 |
| 2009/0227843 A1* | 9/2009 | Smith ............... A61B 17/3423 600/201 |
| 2009/0287163 A1* | 11/2009 | Fischvogt ......... A61M 39/0247 604/264 |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0113882 A1 | 5/2010 | Widenhouse et al. |
| 2010/0113886 A1 | 5/2010 | Piskun et al. |
| 2010/0204548 A1 | 8/2010 | Bonadio et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0240960 A1 | 9/2010 | Richard |
| 2010/0249518 A1* | 9/2010 | Battles ............ A61M 39/0606 600/204 |
| 2010/0249525 A1 | 9/2010 | Shelton, IV et al. |
| 2010/0268035 A1 | 10/2010 | Oberlander et al. |
| 2010/0274093 A1 | 10/2010 | Shelton, IV |
| 2010/0286484 A1 | 11/2010 | Stellon et al. |
| 2010/0298646 A1 | 11/2010 | Stellon et al. |
| 2010/0312060 A1 | 12/2010 | Widenhouse et al. |
| 2010/0312061 A1 | 12/2010 | Hess et al. |
| 2010/0312063 A1 | 12/2010 | Hess et al. |
| 2010/0312065 A1 | 12/2010 | Shelton, IV et al. |
| 2010/0312066 A1 | 12/2010 | Cropper et al. |
| 2011/0015491 A1* | 1/2011 | Ravikumar ............ A61B 1/32 600/233 |
| 2011/0021876 A1 | 1/2011 | Rockrohr |
| 2011/0034935 A1 | 2/2011 | Kleyman |
| 2011/0034946 A1 | 2/2011 | Kleyman |
| 2011/0034947 A1 | 2/2011 | Kleyman |
| 2011/0054257 A1 | 3/2011 | Stopek |
| 2011/0071359 A1 | 3/2011 | Bonadio et al. |
| 2011/0190590 A1 | 8/2011 | Wingardner, III et al. |
| 2011/0208007 A1 | 8/2011 | Shohat et al. |
| 2011/0251466 A1 | 10/2011 | Kleyman et al. |
| 2011/0295076 A1 | 12/2011 | Smith |
| 2012/0022333 A1 | 1/2012 | Main et al. |
| 2012/0130188 A1 | 5/2012 | Okoniewski |
| 2012/0157784 A1 | 6/2012 | Kleyman et al. |
| 2012/0157785 A1 | 6/2012 | Kleyman |
| 2012/0253132 A1 | 10/2012 | Davis |
| 2013/0085341 A1 | 4/2013 | Nobis et al. |
| 2013/0085342 A1 | 4/2013 | Stefanchik et al. |
| 2013/0253132 A1 | 9/2013 | Mijolovic et al. |
| 2015/0073222 A1 | 3/2015 | Kishi |
| 2015/0173735 A1 | 6/2015 | Ortiz et al. |
| 2015/0216562 A1 | 8/2015 | Norton et al. |
| 2015/0238179 A1 | 8/2015 | Kanehira et al. |
| 2017/0056064 A1 | 3/2017 | Zergiebel et al. |
| 2018/0338777 A1 | 11/2018 | Bonadio et al. |
| 2019/0117209 A1 | 4/2019 | Augelli et al. |
| 2019/0117255 A1 | 4/2019 | Kleyman et al. |
| 2019/0117257 A1 | 4/2019 | Kleyman et al. |
| 2019/0159769 A1 | 5/2019 | Ortiz et al. |
| 2019/0223852 A1 | 7/2019 | Atwell |

FOREIGN PATENT DOCUMENTS

| | | |
|---|---|---|
| EP | 0950376 A1 | 10/1999 |
| EP | 1350476 A1 | 10/2003 |
| EP | 1 629 787 A2 | 3/2006 |
| EP | 1 716 813 A1 | 11/2006 |
| EP | 1731105 A1 | 12/2006 |
| EP | 2 098 182 A2 | 9/2009 |
| EP | 2119404 A1 | 11/2009 |
| EP | 2168512 A1 | 3/2010 |
| FR | 2710270 A1 | 3/1995 |
| JP | 2006320750 A | 11/2006 |
| WO | WO-02/17800 A2 | 3/2002 |
| WO | WO-2005/087112 A1 | 9/2005 |
| WO | WO-2005/094432 A2 | 10/2005 |
| WO | WO-2006/019592 A2 | 2/2006 |
| WO | WO-2006/019723 A2 | 2/2006 |
| WO | WO-2006/035446 A2 | 4/2006 |
| WO | WO-2006/110733 A2 | 10/2006 |
| WO | WO-2007/119232 A2 | 10/2007 |
| WO | WO-2008/024502 A2 | 2/2008 |
| WO | WO-2008/093313 A1 | 8/2008 |
| WO | WO-2008/121294 A1 | 10/2008 |
| WO | WO-2008/149332 A1 | 12/2008 |
| WO | WO-2009/035663 A2 | 3/2009 |

OTHER PUBLICATIONS

[No Author Listed] Web Page www.websurg.com/notes/videos.php <http://www.websurg.com/notes/videos.php>, Screenshots videos "Notes Hybrid Sleeve Gastrectomy Performed During Course" Vix, MD; Solano, MD; Asakuma, MD, Feb. 2008.

(56) References Cited

OTHER PUBLICATIONS

[No Author Listed] Web Page www.websurg.com/notes/videos.php <http://www.websurg.com/notes/videos.php>, Screenshots videos "Transvaginal Hybrid Notes Sleeve Gastrectomy Porcine Model" Vix, MD; Solano, MD; Asakuma, MD, Dec. 2007.
Ahmad G, Duffy JM, Phillips K, Watson A., "Laparoscopic Entry Techniques" Cochrane Database Syst Rev., (2):CD006583, Apr. 16, 2008.
Bucher P, Pugin F, Morel P., "Single Port Access Laparoscopic Right Hemicolectomy" Int J Colorectal Dis., Jul. 8, 2008.
Canes D, Desai MM, Aron M, Haber GP, Goel RK, Stein RJ, Kaouk JH, Gill IS., "Transumbilical Single-Port Surgery: Evolution and Current Status" Eur Urol., Jul. 14, 2008.
European Search Report for Application No. 09252291, dated Jan. 19, 2010.
European Search Report for Application No. 09252296, dated Feb. 4, 2010.
European Search Report for EP 09 25 2312 dated Feb. 25, 2010. (5 pages).
European Search Report, 10250402.4, dated Jul. 27, 2010.
European Search Report, 10250406.5, dated Jun. 9, 2010.
Gill IS, Canes D, Aron M, Haber GP, Goldfarb DA, Flechner S, Desai MR, Kaouk JH, Desai MM., "Single Port Transumbilical (E-NOTES) Donor Nephrectomy" Journal Urol., 180(2):637-41; Aug. 2008.
Goel RK, Kaouk JH., "Single Port Access Renal Cryoablation (SPARC): A New Approach" Eur Urol. Jun. 2008;53(6):1204-9. Epub Mar. 18, 2008.
Johnston D , Dachtler J , Sue-Ling HM, King RF, Martin I. G, Roderick F.G. "The Magenstrasse and Mill Operation for Morbid Obesity" Obesity Surgery, Apr. 2003.
Kaouk JH, Haber GP, Goel RK, Desai MM, Aron M, Rackley RR, Moore C, Gill IS., "Single-port Laparoscopic Surgery in Urology: Iniitial Experience", Urology., 71(1):3-6., Jan. 2008.
Kaouk JH, Palmer JS., "Single-port Laparoscopic Surgery: Initial Experience in Children for Varicocelectomy" BJU Int.;102(1):97-9. Epub Mar. 5, 2008.
Ponsky LE, Cherullo EE, Sawyer M, Hartke D., "Single Access Site Laparoscopic Radical Nephrectomy: Initial Clinical Experience" J Endourol., 22(4):663-6, Apr. 2008.
Ponsky TA, Lukish JR., "Single Site Laparoscopic Gastrostomy with a 4-mm Bronchoscopic Optical Grasper" J Pediatric Surgery, 43(2):412-4, Feb. 2008.
Rane A, Rao P, Rao P. Single-port-access Nephrectomy and Other Laparoscopic Urologic Procedures Using a Novel Laparoscopic Port (R-port), Urology. (2):260-3; discussion, Epub May 12, 2008.
Sumiyama, C. Gostout, E.Rajan, T.Bakken, M.Knipschield, S.Chung, P.Cotton, R.Hawes, A.Kalloo, A.Kalloo, S.Kantsevoy and P.Pasricha "Transgastric Cholecystectomy: Transgastric Accessibility to The Gallbladder Improved with the SEMF Method and a Novel Multibending Therapeutic Endoscope" Gastrointestinal Endoscopy , vol. 65, Issue 7, Jun. 2007.
Vassallo C, et al. "The Super-Magenstrasse and Mill Operation with Pyloroplasty: Preliminary Results", Obesity Surgery, Aug. 17, 2007.
European Search Report, 10250402.4, dated Jul. 2, 2013.
U.S. Appl. No. 12/399,547, filed Mar. 6, 2009, U.S. Pat. No. 8,251,900, Mark S. Ortiz et al.
U.S. Appl. No. 12/399,656, filed Mar. 6, 2009, U.S. Pat. No. 8,961,406, Mark S. Ortiz et al.
U.S. Appl. No. 14/594,535, filed Jan. 12, 2015, U.S. Pat. No. 9,538,997, Mark S. Ortiz et al.
U.S. Appl. No. 15/369,220, filed Dec. 5, 2016, U.S. Pat. No. 10,182,805, Mark S. Ortiz et al.
U.S. Appl. No. 16/213,587, filed Dec. 7, 2018, U.S. Pat. No. 10,813,632, Mark S. Ortiz et al.

* cited by examiner

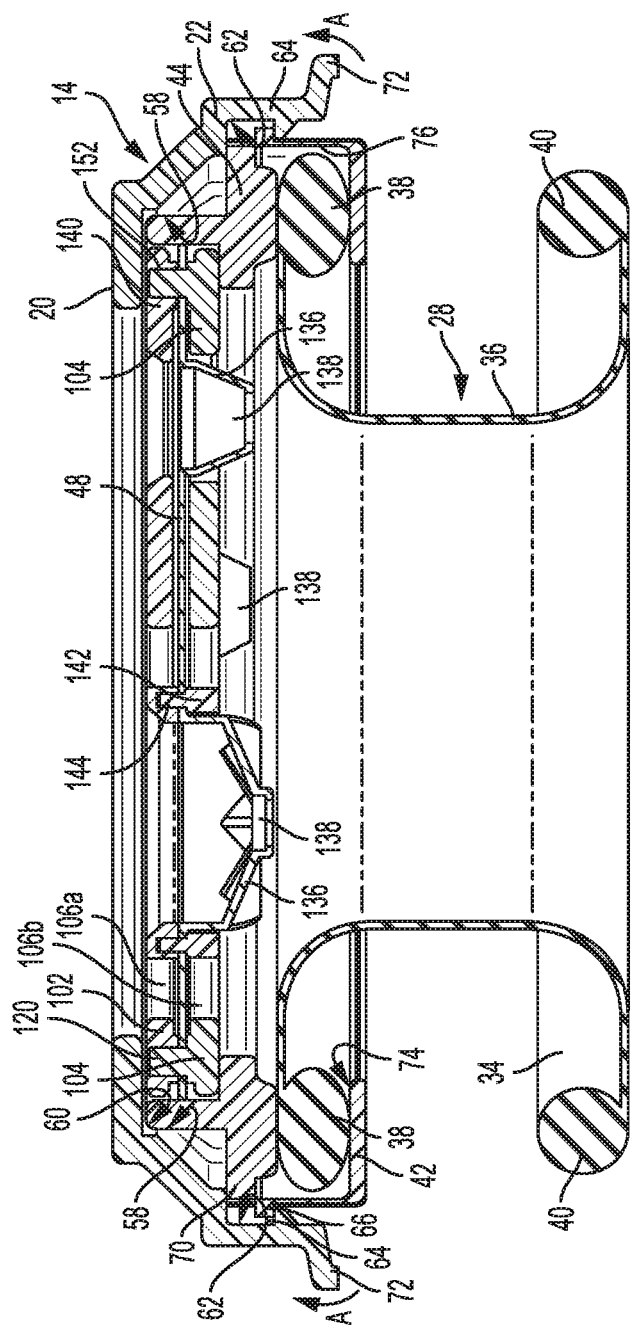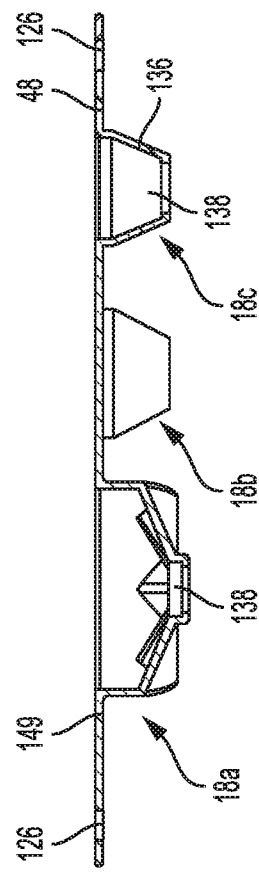

SURGICAL ACCESS DEVICES AND METHODS PROVIDING SEAL MOVEMENT IN PREDEFINED MOVEMENT REGIONS

CROSS REFERENCE TO RELATED APPLICATION

This application is a continuation of U.S. application Ser. No. 16/213,587 (now U.S. Pat. No. 10,813,632) filed Dec. 7, 2018 and entitled "Surgical Access Devices and Methods Providing Seal Movement in Predefined Movement Regions," which is a continuation of U.S. application Ser. No. 15/369,220 (now U.S. Pat. No. 10,182,805) filed on Dec. 5, 2016 and entitled "Surgical Access Devices and Methods Providing Seal Movement in Predefined Movement Regions," which is a continuation of U.S. application Ser. No. 14/594,535 (now U.S. Pat. No. 9,538,997) filed on Jan. 12, 2015 and entitled "Surgical Access Devices and Methods Providing Seal Movement in Predefined Movement Regions," which is a continuation of U.S. patent application Ser. No. 12/399,656 (now U.S. Pat. No. 8,961,406) filed on Mar. 6, 2009 and entitled "Surgical Access Devices and Methods Providing Seal Movement in Predefined Movement Regions," which are hereby incorporated by reference in their entireties.

FIELD OF THE INVENTION

The present invention relates to surgical access devices for providing surgical access into a body cavity.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm diameter straight tubular cannula or trocar sleeve is then inserted into the abdominal cavity. A laparoscopic telescope connected to an operating room monitor is used to visualize the operative field, and is placed through a the trocar sleeve. Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. Instruments used for mini-laparoscopic procedures are, however, generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller 2-3 mm incisions may still cause undesirable cosmetic outcomes and wound complications (bleeding, infection, pain, keloid formation, etc.).

Since the benefits of smaller and fewer body cavity incisions are proven, it would be desirable to perform an operation utilizing only a single incision in the navel. An umbilicus is well-hidden and the thinnest and least vascularized area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems which allow laparoscopic procedures to be performed entirely through the umbilicus or a surgical port located elsewhere while at the same time reducing or eliminating the "chopstick effect."

SUMMARY OF THE INVENTION

The present invention generally provides devices for allowing surgical access to an interior of a patient's body. In one embodiment, a surgical access device is provided and can include a housing having a central axis and a working channel extending therethrough. A seal member can be disposed in the housing and can be configured to seal the working channel. In addition, a plurality of sealing elements can be disposed in the seal member and configured to receive and form a seal around an instrument inserted therethrough and into the working channel. The plurality of sealing elements can include at least one movable sealing element that is movable independent of the other sealing elements within a predetermined path.

In some exemplary embodiments, the seal member can be rotatable about the central axis of the housing to enable collective movement of the plurality of sealing elements. The surgical access device can also include a plurality of movable sealing elements wherein each of the plurality of movable sealing elements is movable independent of the other sealing elements within a predetermined path, such as an elongate track, that is unique to each movable sealing element. The movable sealing elements can be slidable within the elongate track and can be movable in any direction within the elongate track. In one exemplary embodiment, the elongate track can extend in a complete circle within the seal member and the sealing element can be movable around the circle within the track.

The seal member can have various configurations, for example, the seal member can include a deformable membrane and at least a portion of each sealing element can be integrally formed with the deformable membrane. Each sealing element can be angularly movable relative to a planar surface of the housing such that a central axis of the sealing element is non-parallel with the central axis of the housing. At least one of the sealing elements can have an opening with a diameter different than a diameter of an opening in the other sealing elements. In some embodiments, a retractor can extend from the housing and can have an opening formed therethough for receiving surgical instruments. The housing can optionally be rotatable relative to the retractor. The surgical access device can also include a safety shield extending through the retractor and configured to protect the retractor from sharp surgical instruments inserted therethrough.

In other aspects, a surgical access device is provided and can include a housing having a central axis and a working channel extending therethrough, a seal member disposed within the housing and configured to seal the working channel, and a plurality of sealing elements disposed in the seal member. The plurality of sealing elements can be collectively rotatable about the central axis of the housing, and at least one sealing element can be independently movable within a predefined elongate pathway with respect to others of the plurality of sealing elements. The sealing element can be movable in all directions within its predefined elongate pathway.

In some embodiments, the plurality of sealing elements can include a plurality of movable sealing elements and each movable sealing element can be configured for lateral and/or angular movement with respect to the central axis of the housing. At least one of the sealing elements can be configured to rotate 360 degrees about a central axis of the housing. In addition, each sealing element can be angularly movable relative to a planar surface of the housing such that a central axis of the sealing element is non-parallel with the central axis of the housing.

The seal member can have various configurations and can include a flexible membrane that is configured to deform while maintaining a seal in response to movement of a surgical instrument inserted through one of the plurality of sealing elements. In some embodiments, a selective locking mechanism can be included that can be configured to selectively lock a position of at least one of the sealing elements within the seal member against movement in at least one direction. The selective locking mechanism can also be configured to be unlocked to allow the position of at least one sealing element within the seal member to be changed to a new position and can be configured to relock the sealing element against movement in at least one direction in the new position.

In another exemplary embodiment, a surgical access device is provided that can include a flexible retractor having an opening extending therethrough and that is configured to be positioned within a surgical incision, a housing coupled to a portion of the retractor that can be rotatable relative to the retractor, and a base member disposed within the housing that includes a plurality of sealing elements formed therein. The sealing elements can be configured to allow positioning of surgical instruments therethrough in a sealing arrangement. A majority of the sealing elements can be movable sealing elements that are movable independent of the other of the plurality of sealing elements within a predefined movement region within the base member.

In some embodiments, the base member can include an upper bearing plate and a lower bearing plate. Each bearing plate can have predefined movement regions formed therein to guide movement of the movable sealing elements. The base member can further include a deformable seal member disposed between the upper and lower bearing plates that is effective to seal a working channel extending through the housing and the retractor. The plurality of sealing elements can optionally each include a flexible sealing membrane integrally formed with the deformable seal member and configured to form a seal around a surgical instrument inserted therethrough.

In one embodiment, the plurality of sealing elements can each include an upper seal support and a lower seal support that are configured to mate together such that the flexible sealing membrane of the sealing element is coupled between the upper and lower seal supports. The upper seal support can be movable within the predefined movement region formed in the upper bearing plate and the lower seal support can be movable within the predefined movement region formed in the lower bearing plate. The surgical access device can also include an insufflation port extending from a side wall of the housing and configured to provide insufflation into a body through a working channel extending through the housing and the retractor.

In other aspects, methods for accessing a surgical site within a body are also provided and can include inserting a flexible retractor of a surgical access device into an opening in a body in proximity to an interior surgical site, inserting a surgical instrument into a sealing element disposed within a sealing member of a housing of the surgical access device such that the surgical instrument extends through a working channel of the surgical access device and into the interior surgical site, and moving the surgical instrument laterally and/or angularly to cause corresponding lateral and/or angular movement of the sealing element within a predefined pathway formed in the housing to better access the interior surgical site.

In some embodiments, moving the surgical instrument laterally and/or angularly to cause corresponding lateral and/or angular movement of the sealing element within a predefined pathway can include stretching and pushing the sealing member. In other embodiments, moving the surgical instrument laterally can cause corresponding lateral movement of the sealing element within a predefined pathway and can include moving the sealing element from a center portion of the predefined pathway to one end of the predefined pathway.

Certain exemplary methods can also include inserting a second surgical instrument into a second sealing element disposed within the sealing member of the housing of the surgical access device such that the second surgical instrument extends through the working channel of the surgical access device and into the interior surgical site. The method can further include moving the second surgical instrument laterally and/or angularly to cause corresponding lateral and/or angular movement of the second sealing element within a second predefined pathway independently of the surgical instrument within the predefined pathway.

BRIEF DESCRIPTION OF THE DRAWINGS

The invention will be more fully understood from the following detailed description taken in conjunction with the accompanying drawings, in which:

FIG. 5 is a cross-sectional view of the surgical access device of FIG. 1;

FIG. 6 is a cross-sectional view of a sealing member of the surgical access device of FIG. 1.

DETAILED DESCRIPTION OF THE INVENTION

Figure 1:
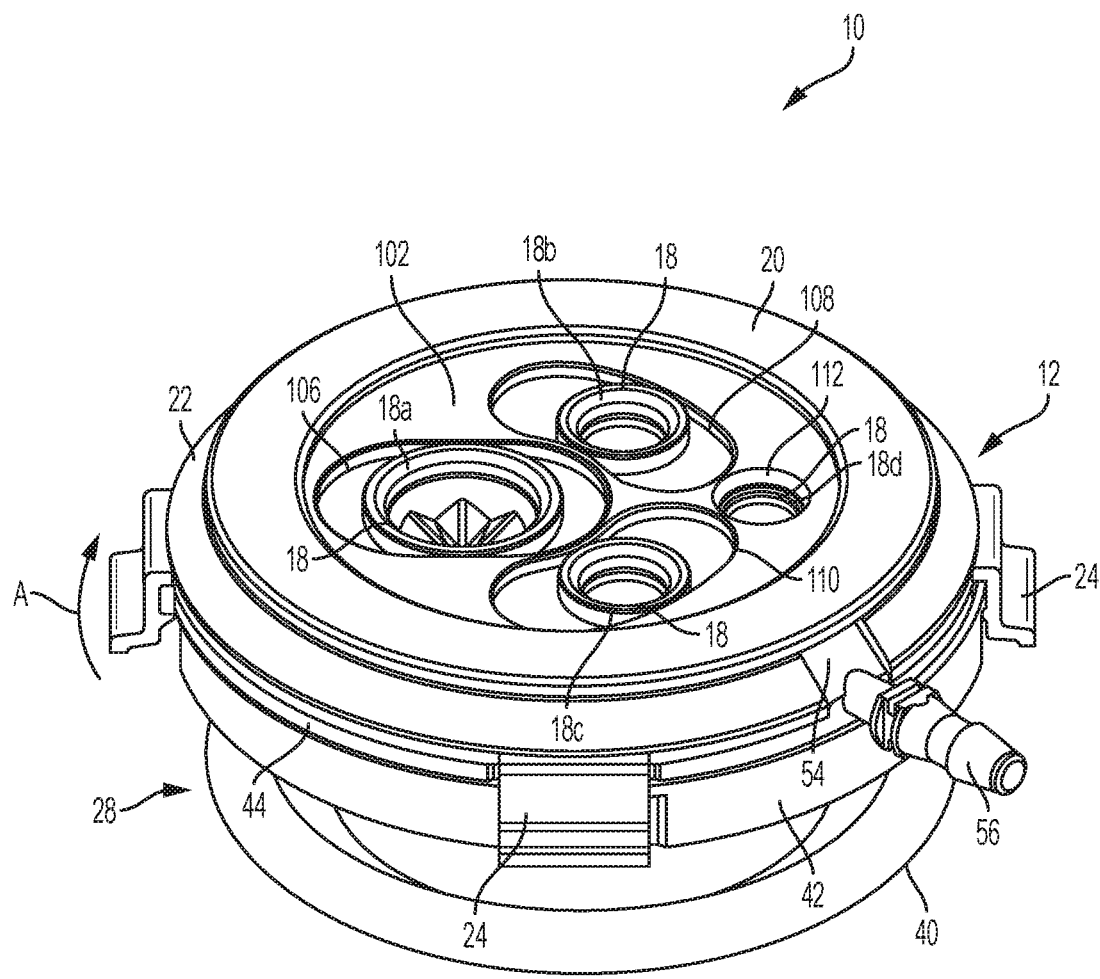
FIG. 1 is a perspective view of one embodiment of a surgical access device having sealing elements disposed in predefined paths.
Figure 2:
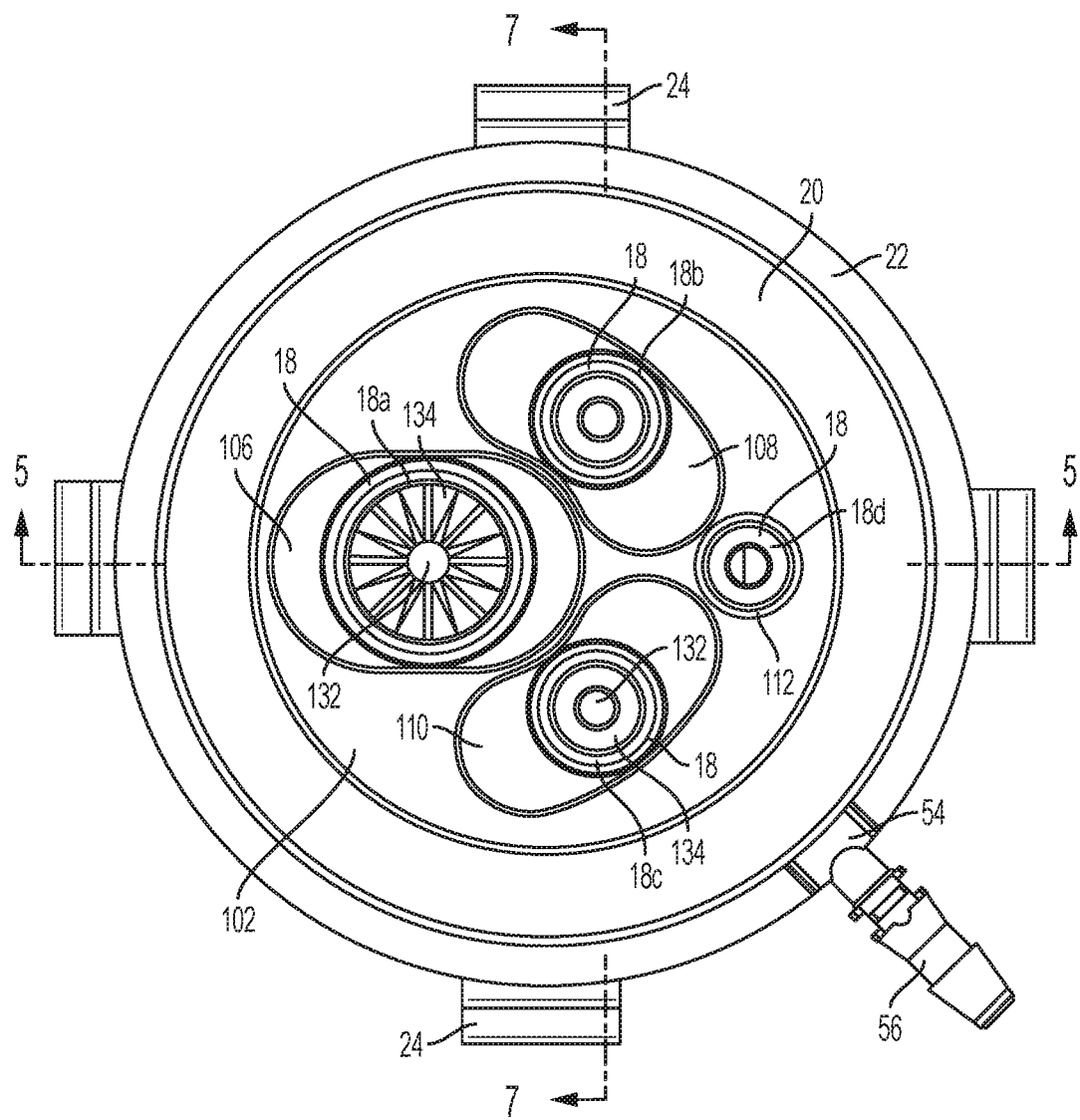
FIG. 2 is top view of the surgical access device of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those of skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides improved surgical access devices that allow multiple surgical instruments to be inserted into sealing elements of a single surgical access device. The improved surgical access devices allow surgical instruments inserted through the sealing elements to be moved laterally, rotationally, angularly, and vertically for ease of manipulation within a patient's body while maintaining insufflation.

In certain exemplary embodiments, a housing is provided having a base member with a plurality of sealing elements coupled thereto for receiving and forming a seal around surgical instruments inserted therein. The base member can provide one or more predetermined paths, predefined movement regions, and/or predefined elongate pathways that can guide lateral, independent movement of the sealing elements therein, thereby allowing for lateral movement of surgical instruments inserted within the sealing elements. The housing can define a central longitudinal axis, and the plurality of sealing elements can each have a central axis that can be angularly adjustable relative to the central longitudinal axis of the housing within the predetermined paths of the base member, thereby allowing a surgeon more control over the insertion of multiple surgical instruments. In some embodiments, the plurality of sealing elements can be collectively rotated about the central axis of the housing to enable greater surgeon maneuverability within the device.

The various surgical access devices can further include a wound protector, cannula, ring retractor, or other member for forming a pathway through tissue (hereinafter generally referred to as a retractor). The retractor can extend from the housing and it can be configured to be positioned within an opening in a patient's body. The sealing elements can each define working channels extending through the housing that are generally aligned with the retractor. Any and all of the surgical access devices described herein can also include various other features, such as one or more ventilation ports to allow evacuation of smoke during procedures that utilize cautery and/or one or more insufflation ports through which the surgeon can insufflate the abdomen to cause pneumoperitenium, as described for example in U.S. Patent Application No. 2006/0247673 entitled "Multi-port Laparoscopic Access Device" filed Nov. 2, 2006 and incorporated herein by reference in its entirety. The insufflation port can be any size and can accept a leur lock or a needle, as will be appreciated by those skilled in the art.

In use, the surgical access devices disclosed herein can be utilized to provide access to a patient's body cavity. The retractor can be positionable within an opening in a patient's body such that a distal portion of the retractor extends into a patient's body cavity and a proximal portion is coupled to a housing positioned adjacent to the patient's skin on an exterior of the patient's body. A lumen in the retractor can form a pathway through the opening in a patient's body so that surgical instruments can be inserted from outside the body, through the sealing elements, to an interior body cavity. The elasticity of the skin of the patient can assist in the retention of the retractor in the body opening or incision made in the body. The retractor can be placed in any opening within a patient's body, whether a natural orifice or an opening made by an incision. In one embodiment, the retractor can be substantially flexible so that it can easily be maneuvered into and within tissue as needed. In other embodiments, the retractor can be rigid or semi-rigid. The retractor can be formed of any suitable material known in the art, for example silicone, urethane, thermoplastic elastomer, and rubber.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Some of the embodiments disclosed herein can be used with only one type of seal, for example an instrument seal, that prevents air and/or gas from escaping when a surgical instrument is inserted therethrough, but otherwise does not form a seal when no instrument is disposed therethrough. Other embodiments can include various sealing elements that are known in the art, and can include at least one instrument seal, at least one channel seal or zero-closure seal that seals the working channel created by the sealing port when no instrument is disposed therethrough, and/or a combination instrument seal and channel seal that is effective to both form a seal around an instrument disposed therethrough and to form a seal in the working channel when no instrument is disposed therethrough. A person skilled in the art will appreciate that various seals known in the art can be used including, for example, duckbill seals, cone seals, flapper valves, gel seals, diaphragm seals, lip seals, gimbal seals, deep cone seals, iris seals, slit seals, etc. A person skilled in the art will also appreciate that any combination of seals can be included in any of the embodiments described herein, whether or not a particular seal combination is specifically discussed in the corresponding description of a particular embodiment.

One aspect of the embodiments disclosed herein is that exemplary surgical access devices provide for greater maneuverability of surgical instruments within a patient while maintaining insufflation. In one embodiment, this greater maneuverability can be provided by having predefined movement regions, predefined elongate pathways, tracks, and/or predetermined paths formed within the housing that allow sealing elements, and surgical instruments disposed within the sealing elements, to be independently moved within and/or along the predetermined paths to allow for a greater range of motion. In addition, the sealing elements can be angled relative to the predetermined paths to allow for angular manipulation of the surgical instruments as well as lateral movement along the predefined paths. In some embodiments, each sealing element can include a flexible sealing membrane that can be integrally formed with a flexible sealing member. The flexible sealing member can provide a gas tight seal within the housing and across the working channel and can stretch, twist, bunch, and otherwise deform to allow the sealing elements to move laterally, angularly, and vertically within their predetermined paths and relative to other sealing elements. In addition, the entire sealing member can be rotated 360 degrees to thereby rotate the sealing elements to allow a change in position of surgical instruments inserted through the sealing elements. It will be appreciated by those skilled in the art that any of the various aspects and features of the surgical access device embodiments described herein can be used in and applied to any and all of the various other embodiments, to various devices known in the art, or to devices yet to be developed.

One exemplary embodiment of a surgical access device 10 is illustrated in FIGS. 1-6. As shown, the surgical access device 10 can generally include a housing 12 with a retractor 28 extending distally therefrom. The housing 12 and the retractor 28 can define a working channel extending therethrough and a central longitudinal axis 30. The housing 12 can generally include one or more sealing elements 18 and/or sealing members 48 and the retractor 28 can be configured to be positioned within an opening in a patient's body to provide access to an interior surgical site. The tissue surrounding an opening in which the retractor 28 is placed can exert a pressure on the retractor 28 to hold the retractor 28 in place within a body such that the housing 12 is positioned against tissue on the exterior of the body. In this way, an access pathway to an interior surgical site is created through which surgical instruments can be inserted to perform a surgical procedure.

As noted above, the retractor 28 can extend from the housing, and in one embodiment, the retractor 28 is a substantially flexible member having a proximal flange 32 and a distal flange 34 with an inner elongate portion 36 extending therebetween. The proximal flange 32 can be positioned within a distal portion of the housing 12. A proximal o-ring 38 can be included within the proximal flange 32 to add structural support to the proximal flange 32 and to aid in allowing rotation of the housing 12 relative to the retractor 28, as will be described in more detail below. A distal o-ring 40 can optionally be included within the distal flange 34 of the retractor 28 to provide structural support to the retractor 28 within a patient's body. The proximal and distal o-rings 38, 40 can be flexible or substantially rigid as needed for use in a particular application.

Figure 3:
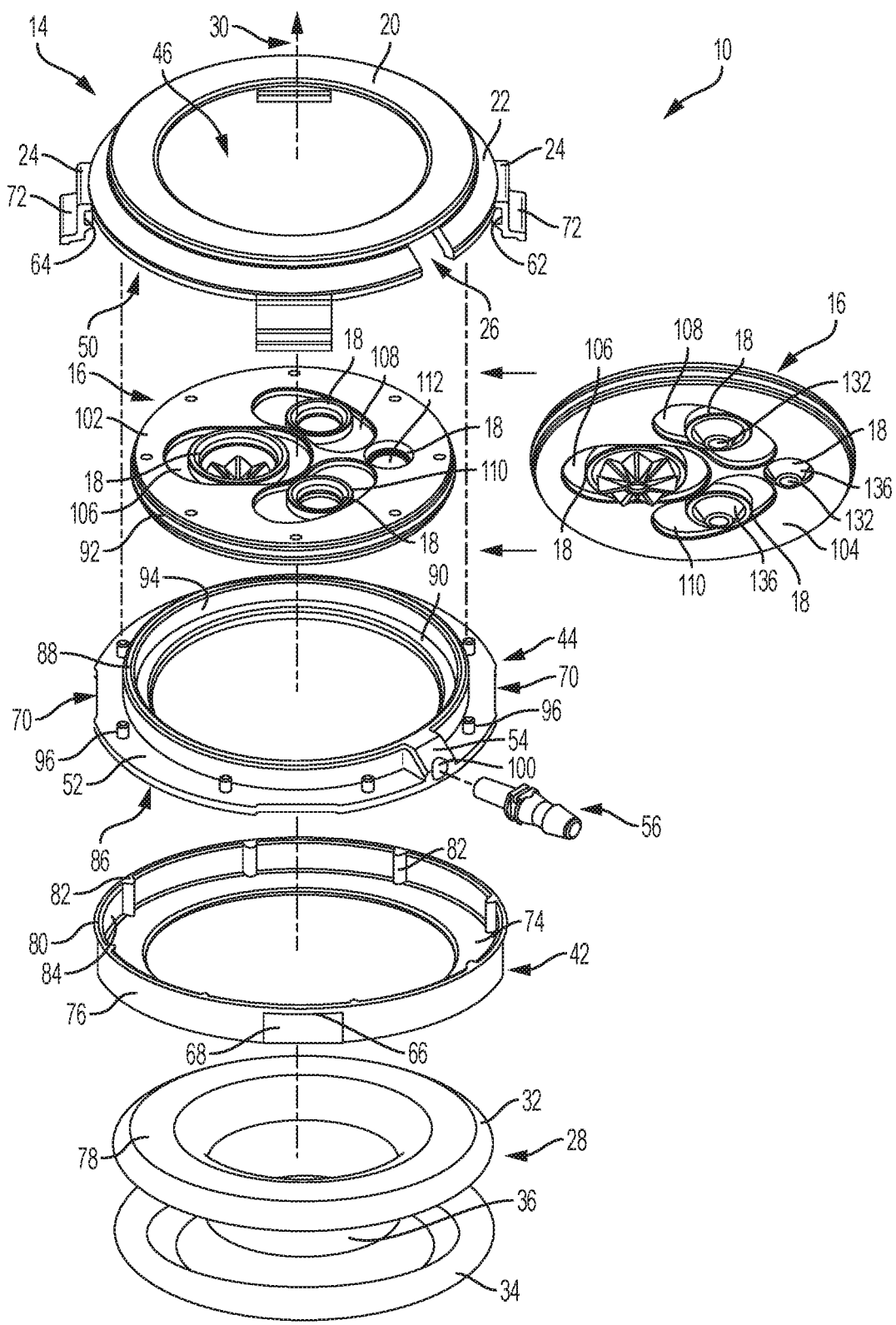
FIG. 3 is an exploded view of the surgical access device of FIG. 1.

Referring particularly to FIG. 3, the device 10 can include a housing cover 14 and a housing support 42 that can be mated together to generally form the structure of the housing 12. The housing 12 can further include a base member 16 and a base member support 44 secured between the housing cover 14 and the housing support 42. In some embodiments, the housing cover 14 can be formed of a crown 20 and cover flange 22 with one or more latches 24 extending from the cover flange 22 to aid in securing the housing cover 14 to the housing support 42. The crown 20 of the housing cover 14 can generally serve as a top most portion of the housing 12 and is in the shape or form of a ring defining an opening 46 in the housing cover 14 that allows access to the sealing elements 18. The crown 20 can have a diameter that is, for example, smaller than a diameter of the cover flange 22. In other embodiments, the crown 20 can have a diameter that is the same as, or larger than, a diameter of the cover flange 22 depending on the requirements of a particular surgical access device.

In the illustrated embodiment, the crown 20 and the cover flange 22 are integrally formed as a single component and the cover flange 22 extends distally at an angle from the crown 20 in an expanding diameter. In other embodiments, the crown 20 and the cover flange 22 can be adhered and/or fastened together with any mating mechanism known in the art, such as adhesive, screws, threads, etc. The cover flange 22 can have a ring-like shape with a diameter that can generally define an outer diameter or outer circumference of the housing 12. A distal surface 50 of the cover flange 22 can be substantially level or flat to enable flush mating with an outer rim 52 of the base member support 44. A notch 26 can be formed in the cover flange 22 to receive an insufflation access port 54 formed in the base member support 44 that can receive an insufflation port 56. One or more apertures or openings 58, shown in FIGS. 5 and 6, can be formed into the cover flange 22 around a circumference thereof to enable further mating between the housing cover 14 and the base member support 54, as will be described in more detail below. In some embodiments, the openings 58 in the cover flange 22 can extend upward or proximally from the distal surface 50 of the cover flange 22 to a lower or distal surface 60 of the crown 20. As will be appreciated by those skilled in the art, any number of mating or coupling mechanisms can be formed in and/or around the housing cover 14 to allow mating with other components of the housing 12.

As noted above, one or more latches 24 can extend from the cover flange 22 of the housing cover 14 to allow the housing cover 14 to mate or couple with the housing support 42. As shown most clearly in FIGS. 5 and 6, the latches 24 can include a recessed groove 62 having an inner lip 64 that can support and seat an outer rim 66 formed by a recessed portion 68 of the housing support 42. The recessed groove 62 within the latch 24 can also receive a recessed lip 70 of the base member support 44 seated on top of the outer rim 66, thereby securing all components of the housing 12 together. An outer lip 72 of the latch 24 allows for the latch 24 to be manually moved outward and upward, as indicated by the directional arrow A in FIG. 5, to enable the housing cover 14 to be unlatch from the rest of the housing 12. As will be appreciated, any number of mating and/or coupling mechanisms can be used to mate the housing cover 14 with the rest of the housing 12, including but not limited to, adhesives, threads, screws, bayonet latches, etc.

Referring to FIGS. 3, 5, and 6, the housing support 42 is illustrated as a generally ring-shaped member having a seating flange 74 with a circumferential sidewall 76 extending proximally from an outer circumference of the seating flange 74. The seating flange 74 can be configured to seat the proximal flange 32 of the retractor 28 such that a top surface 78 of the proximal flange 32 is positioned slightly below a top surface 80 of the circumferential sidewall 76. The proximal flange 32 can generally be seated within the housing support 42 without the aid of any securement mechanism in order to allow the housing 12 to be moved relative to the retractor 28. Thus, the proximal flange 32 of the retractor 28 can have a diameter smaller than a diameter of the circumferential sidewall 76, and in some embodiments, can have a diameter significantly smaller than a diameter of the circumferential sidewall 76 to allow for both lateral, sliding movement and rotational, sliding movement of the housing 12 relative to the retractor 28. In other embodiments, the diameter of the proximal flange 32 can be only slightly smaller than a diameter of the circumferential sidewall 76 to prevent such lateral, sliding movement while still allowing for rotational, sliding movement. The housing support 42 can optionally include one or more frictional protrusions 82 extending inward from an inner surface 84 of the circumferential sidewall 76 to provide a surface against which the proximal flange 32 can move as the housing 12 is being moved or rotated relative to the retractor 28. As shown, the inner elongate portion 36 of the retractor 28 can extend proximally through the opening formed in the housing support 42, thereby defining the working channel through which instruments can be inserted.

While the housing support 42 can have many configurations, in the illustrated embodiment, the top surface 80 of the circumferential sidewall 76 has a diameter equal to a diameter of the base member support 44 and can thus sit flush against a bottom or distal surface 86 of the base member support 44. The sidewall 76 can also have other diameters smaller or larger than the base member support 44 as needed in a particular application. As previously noted, the housing support 42 can have one or more recessed portions 68 formed in the circumferential sidewall 76 for mating with one or more latches 24 of the housing cover 14. The proximal outer rim 66 of the recessed portion 68 can be seated by the inner lip 64 of the recessed grooves 62 of the latches 24 extending from the housing cover 14.

Figure 7:
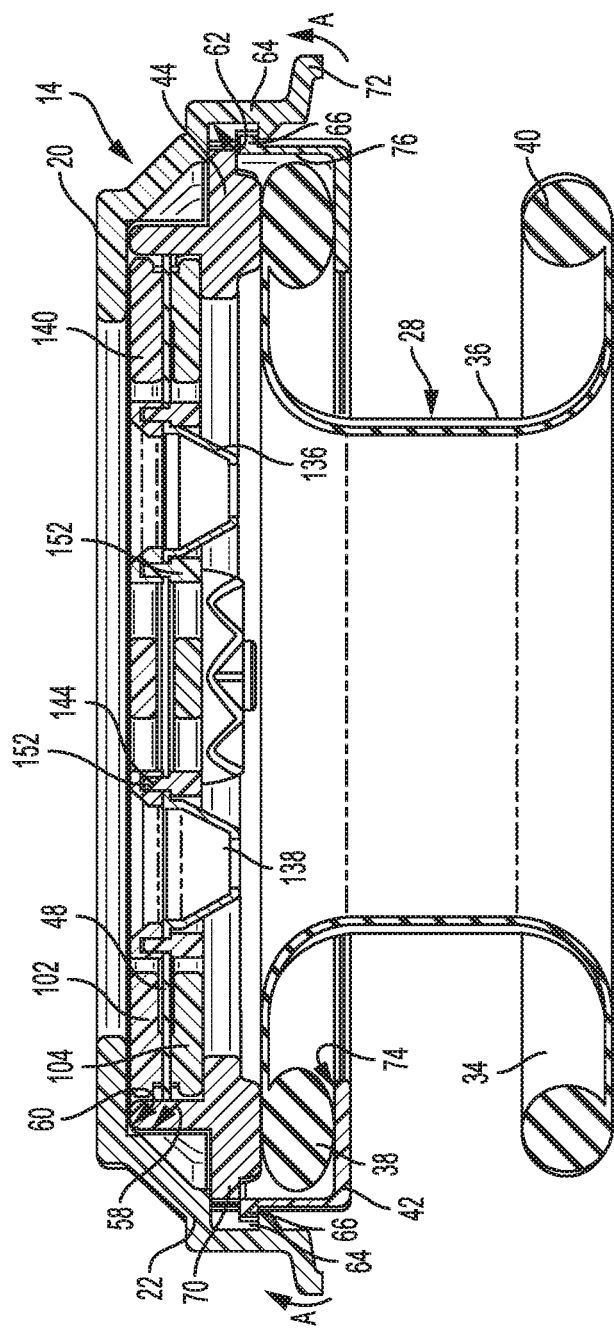
FIG. 7 is another cross-sectional view of the surgical access device of FIG. 1.

As also noted above, the base member 16 and the base member support 44 can be secured between the housing cover 14 and the housing support 42. The base member 16 can generally be seated or disposed within the base member support 44, and the base member support 44 can provide the connection or coupling to the housing cover 14 and the housing support 42. As shown in FIGS. 3, 5, and 7 the base member support 44 has a planar flange portion in the shape of a ring with a circular sidewall 88 extending proximally from the planar flange portion such that the flange portion is divided into two sections. A first section or inner rim 90 forms a seating area with the sidewall 88 for receiving and seating the base member 16. The second section or outer rim 52 provides mating elements for mating the base member support 42 to the housing cover 14.

In some embodiments, an inner surface 94 of the sidewall 88 can include threads formed therearound and/or another engagement mechanism for mating with corresponding threads or engagement mechanisms formed on an outer circumference 92 of the base member 16, thereby securing the base member while still allowing rotation thereof. In the illustrated embodiment, the base member 16 fits securely within the base member support 44 through a loose press fit and/or interference fit connection between the outer circumference 92 of the base member 16 and the inner surface 94 of the sidewall 88. The loose press fit or interference fit can be such that the base member 16 is freely rotatable in both directions relative to the base member support 42 and the rest of the housing 12. Rotation of the base member 16 relative to the base member support 42 and the housing 12 allows rotation of all of the sealing elements 18 disposed within the base member 16 as a unit, as will be described further below.

There are many ways in which the base member support 42 and the housing cover 14 can be joined, but in one embodiment, the outer rim 52 of the base member support 42 can include one or more mating protrusions 96 extending therefrom for mating with one or more corresponding openings 58 in the housing cover 14. A press fit, interference fit, and/or adhesive, for example, can be used to join the protrusions 96 with the openings 58 in the housing cover 14. When secured between the housing cover 14 and the housing support 42, a proximal or top surface of the outer rim 52 can be positioned adjacent to the distal surface 50 of the cover flange 22. The outer rim 52 can have an outer circumference that is substantially flush with the outer circumference of the cover flange 22. The distal or bottom surface 86 of the outer rim 52 can be positioned adjacent to the top surface 80 of the circumferential wall 76 of the housing support 42, and its outer circumference can also be substantially flush with the outer circumference of the housing support 42. One or more recessed slots 70 can be formed around an outer circumference of the outer rim 52 to correspond with the recessed portions 68 formed in the housing support 42 for receiving the housing cover latch 24. As noted above, the recessed portion 68 can be securely grasped on top of the outer rim 66 of the housing support 42 within the groove 62 of the latch 24.

The insufflation access port 54 can be formed in the base member support 44 and can consist of an opening 100 extending from the outer circumference of the outer rim 52 and through the sidewall 88 into the working channel. The opening 100 can receive the insufflation port 56 for introducing insufflation gases through the working channel and into a body. The opening 100 can extend into the working channel at a position below or distal to the base member 16 and the sealing elements 18 disposed in the base member 16. In this way, insufflation gases can be introduced and retained in the working channel and body by the sealing elements 18 when surgical instruments are inserted therethrough. In the illustrated embodiment, the insufflation port 56 extends perpendicularly to the central longitudinal axis 30 of the housing 12, but as will be appreciated by those skilled in the art, insufflation access ports 54 can be positioned at any suitable place within the housing 12. In addition, the insufflation ports 56 can extend from the housing 12 at any angle relative to its central longitudinal axis 30, including parallel thereto.

Figure 4:
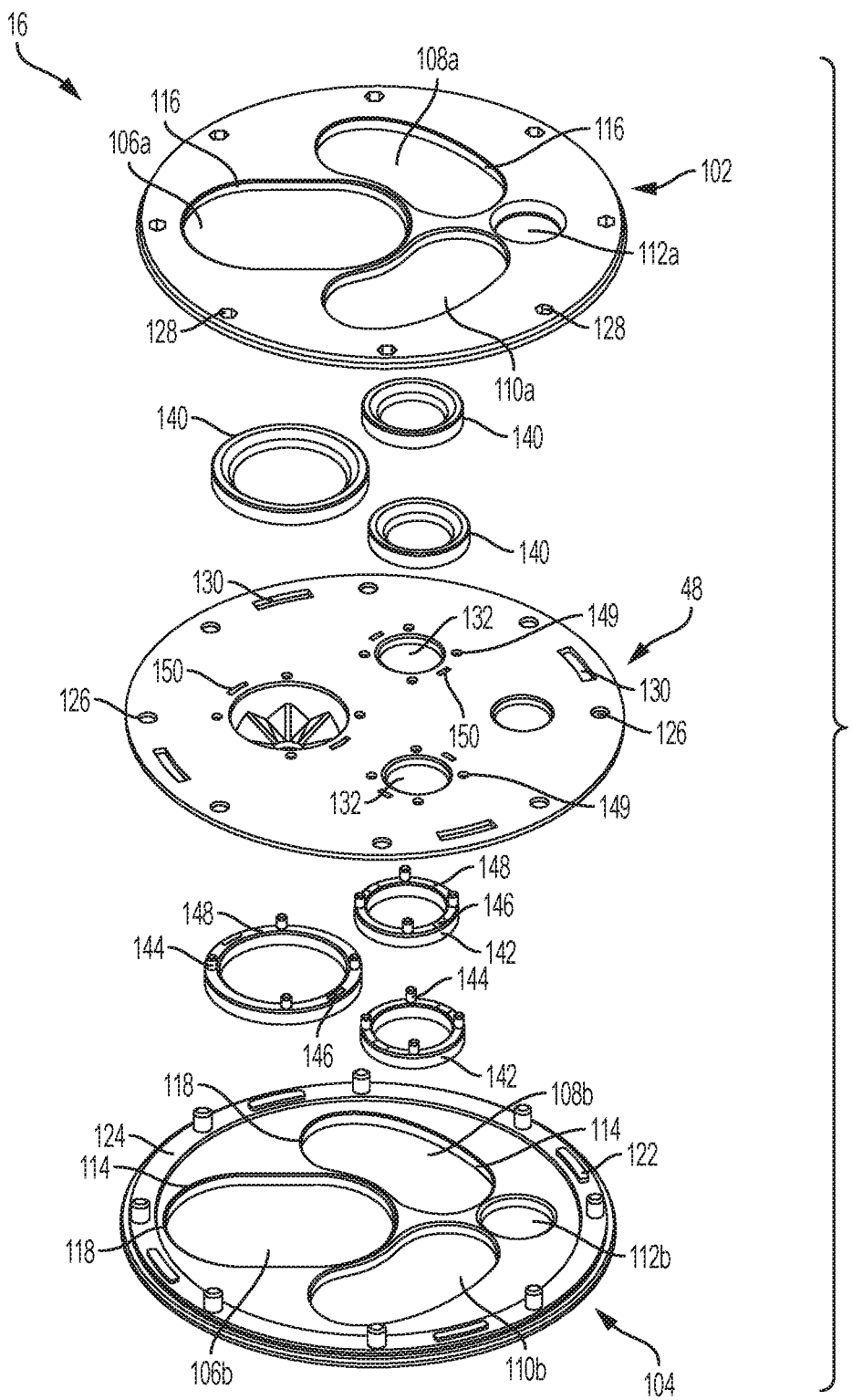
FIG. 4 is an exploded view of a base member included in the surgical access device of FIG. 1.

Referring now to FIGS. 1 and 4, the various components of the exemplary base member 16 are illustrated in more detail. As shown, the base member 16 can include an upper bearing plate 102, a lower bearing plate 104, and the sealing member 48 disposed between the two bearing plates 102, 104. The sealing elements 18 can extend through the sealing member 48 and the bearing plates 102, 104, as will be described in more detail below. The upper and lower bearing plates 102, 104 can each include one or more predefined movement regions, predefined elongate pathways, predetermined paths, and/or tracks formed therein that are provided to guide movement of the sealing elements 18. The bearing plates 102, 104 are generally each substantially flat, circular elements that, in some embodiments, can be substantially rigid. In other embodiments, one or both of the bearing plates 102, 104 can be substantially flexible as needed in a particular application. Each bearing plate 102, 104 can be formed of any suitable material known in the art, including but not limited to, polycarbinate and/or high density polyethelene. In the illustrated embodiment, three generally elongate tracks 106, 108, 110 are provided in the upper and lower bearing plates 102, 104 for receiving three movable sealing elements 18a, 18b, 18c therein. In addition, a fourth, generally circular opening 112 is provided to receive a more constrained, non-movable sealing element 18d therein. As will be appreciated by those of skill in the art, any number of tracks can be disposed in the bearing plates 102, 104 as needed.

While the tracks 106, 108, 110 can have any size, shape, length, and curvature known in the art, in the illustrated embodiment, the tracks 106, 108, 110 are generally elongate and have a width substantially corresponding to a diameter of the sealing element 18 disposed therein and a length corresponding to between about one and a half to two times the diameter of the sealing element 18 disposed therein. In other embodiments, the tracks 106, 108, 110 can have a width and/or a length corresponding to anywhere between about two to five times a diameter of the sealing element 18 disposed therein. The number of tracks within a bearing plate can range between one and any number (two, three, four, five, six, etc.) that can reasonably fit within a diameter of the bearing plates 102, 104. Thus, a single track formed within the base member 16 can have a substantially large size relative to the size of the bearing plates 102, 104, while multiple tracks formed within the base member 16 can have a smaller size relative to the size of the bearing plates 102, 104. Multiple tracks can also have substantially different sizes from one another.

Figure 38A:
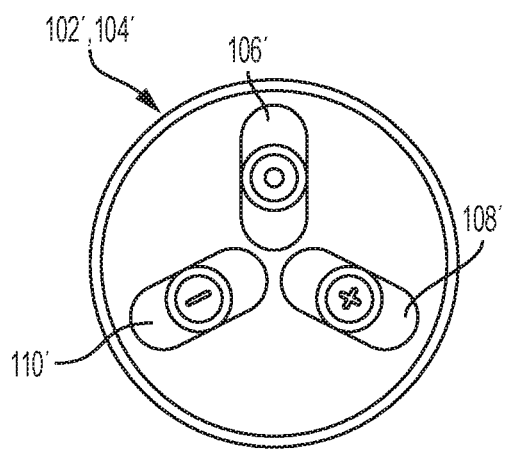
FIG. 38A is a top view of one embodiment of a base member having tracks formed therein.
Figure 38B:
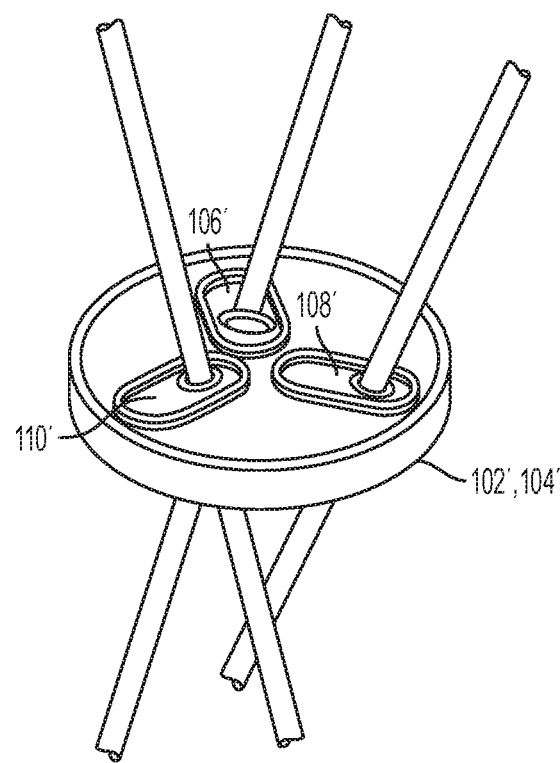
FIG. 38B is a perspective view of the base member of FIG. 38A.
Figure 38C:
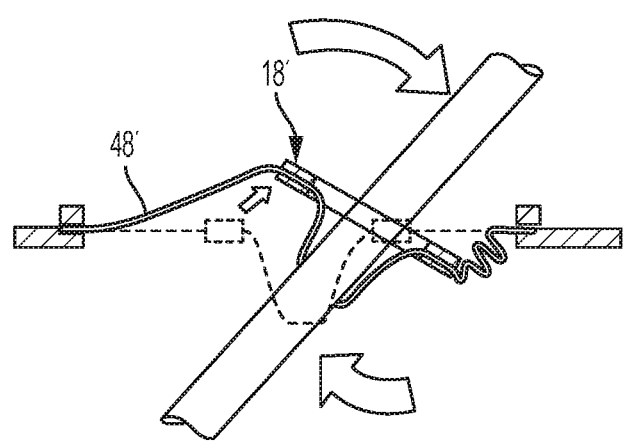
FIG. 38C is a cross-sectional view of a sealing element in the base member of FIG. 38A.

The tracks 106, 108, 110 can generally be positioned and spaced within the upper and lower bearing plates 102, 104 in any way as needed in a particular application. In the embodiment shown in FIGS. 1-6, a first track 106 is a substantially straight track and extends from a position adjacent to an outer diameter of the upper and lower bearing plates 102, 104 into a center portion of the plates 102, 104. Second and third tracks 108, 110 can be positioned on opposite sides of the first track 106 and can also extend from a position adjacent to an outer diameter of the upper and lower bearing plates 102, 104. As shown, the second and third tracks 108, 110 curve slightly inward around a portion of the first track 106 that extends into the center of the bearing plates 102, 104. The fourth opening 112 is disposed at a position substantially opposite to a position of the first track 106. In other embodiments, the tracks 106, 108, 110 can be situated around a diameter of the bearing plates 102, 104 or, as shown in FIGS. 38A-38C, tracks 106', 108', 110' can all extend from an outer diameter into a center of the bearing plates 102', 104'. As shown, the bearing plates 102', 104' can have a sealing element 18' formed therein with a flexible sealing member 48' therearound. In addition, in some embodiments all of the tracks 106, 108, 110 can be straight and in other embodiments, all of the tracks 106, 108, 110 can have a curvature. There are many configurations possible for the shape and positioning of the tracks 106, 108, 110 within the bearing plates 102, 104 and such configurations should not be limited to the several that are noted herein.

In the illustrated embodiment, the upper bearing plate tracks 106a, 108a, 110a can have smooth interior sidewalls 116 to enable smooth movement of the movable sealing elements 18a, 18b, 18c within the upper bearing plate tracks 106a, 108a, 110a. In addition, the lower bearing plate tracks 106b, 108b, 110b can have interior sidewalls with a smooth proximal portion 114 corresponding in size to the sidewalls 116 of the upper bearing plate tracks 106a, 108a, 110a to enable smooth movement of the sealing elements 18a, 18b, 18c within the tracks 106b, 108b, 110b. A lower or distal portion 118 of the sidewalls can extend or protrude slightly into the tracks 106b, 108b, 110b to form a lip extending therearound that has a size slightly smaller than a size of the proximal portion 114 and a size of the sidewalls 116 of the upper bearing plate tracks 106a, 108a, 110a. The sealing elements 18a, 18b, 18c can move and/or slide along the lip formed in the lower bearing plates tracks 106b, 108b, 110b and vertical and/or longitudinal movement of the sealing elements 18a, 18b, 18c below the lower bearing plate tracks 106b, 108b, 110b is restrained or prohibited while vertical and/or longitudinal movement of the sealing elements 18a, 18b, 18c above the upper bearing plate tracks 106a, 108a, 110a is not restrained or prohibited. In other embodiments, the sidewalls 116, 114, 118 of the upper and lower bearing plate tracks 106a, 106b, 108a, 108b, 110a, 110b are completely smooth, with no lip, such that vertical and/or longitudinal movement below and above the tracks is allowed.

In other exemplary embodiments, engagement elements, such as grooves or recesses, can extend around the sidewalls 116, 114, 118 in the upper and/or lower bearing plate tracks 106a, 106b, 108a, 108b, 110a, 110b that are configured to mate with corresponding engagement elements formed around the sealing elements 18a, 18b, 18c to provide constrained vertical and/or longitudinal movement of the sealing elements 18a, 18b, 18c while allowing lateral, guided movement within the tracks 106, 108, 110. A person skilled in the art will appreciate the various ways of allowing or preventing movement of the sealing elements 18a, 18b, 18c within the bearing plate tracks 106, 108, 110 as needed for a particular application. In addition, one or more tracks 106, 108, 110 can provide constrained movement of a sealing element 18a, 18b, 18c disposed therein while one or more tracks 106, 108, 110 can provide a full range of movement and/or motion of a sealing element 18a, 18b, 18c disposed therein.

The upper and lower bearing plates 102, 104 can be joined or coupled together by any method known in the art, including but not limited to, adhesive, screws, press fit, interference fit, etc. In the illustrated embodiment, one or more cylindrical protrusions 120 and one or more elongate protrusions 122 are formed around an outer rim 124 of the lower bearing plate 104 such that they extend proximally therefrom. The cylindrical protrusions 120 are configured to extend through securement openings 126 formed around an outer diameter of the sealing member 48 and into corresponding openings 128 formed around an outer diameter of the upper bearing plate 102 such that a press fit or interference fit is achieved between the cylindrical protrusions 120 and the openings 128 in the upper bearing plate 102. The elongate protrusions 122 are configured to secure the lower bearing plate 104 to the sealing member 48 and thus extend into corresponding elongate slots 130 formed around the outer diameter of the sealing member 48. In this way, the base member 16 is secured together with the sealing member 48 coupled between the upper and lower bearing plates 102, 104.

The sealing member 48 can have many configurations and in the illustrated embodiment, the sealing member 48 generally seals the working channel of the surgical access device 10 by providing an air and gas tight seal between the upper bearing plate 102 and the lower bearing plate 104. The sealing member 48 can be composed of a flexible, stretchable, and/or deformable material that is able to flex, stretch, bunch and/or otherwise deform to allow the sealing elements 18a, 18b, 18c disposed therethrough to be moved within their respective tracks 106, 108, 110 within the bearing plates 102, 104. In the illustrated embodiment, the sealing member 48 is a relatively thin, deformable membrane that has a diameter corresponding to a diameter of the upper and lower bearing plates 102, 104 such that it can be positioned and form a seal between the upper and lower bearing plates 102, 104. The sealing member 48 can be formed of any suitable material known in the art, including but not limited to, silicone, urethane, sanaprene, isoprene, and/or krayton.

The sealing member 48 can include one or more openings 132 formed therethrough that define openings for one or more sealing elements 18. As noted above, each sealing element 18 can be a movable sealing element, for example, movable sealing elements 18a, 18b, 18c, or a non-movable sealing element, for example, non-movable sealing element 18d. Movable sealing elements 18a, 18b, 18c are generally configured to be independently movable within their respective bearing plate tracks 106, 108, 110 relative to the housing, each other, and to non-movable sealing elements. The non-movable sealing element 18d is generally configured to be secured within a circular opening, for example, opening 112, in the bearing plates 102, 104 that does not provide room for the sealing element 18d to move. In some embodiments, the movable sealing elements 18a, 18b, 18c compose a majority of the total number of sealing elements 18 disposed within the base member 16. In addition, one or more sealing elements 18 can have an opening with a different diameter than an opening of the other sealing elements 18. For example, one or more movable sealing elements 18a, 18b, 18c can have an opening with a diameter that is the same as, larger than, or smaller than openings in other movable sealing elements 18a, 18b, 18c and in other non-movable sealing element 18d. One or more non-movable sealing elements 18d can have an opening with a diameter that is the same as, larger than, or smaller than openings in other non-movable sealing elements (not shown) and in other movable sealing elements 18a, 18b, 18c.

Figure 8:
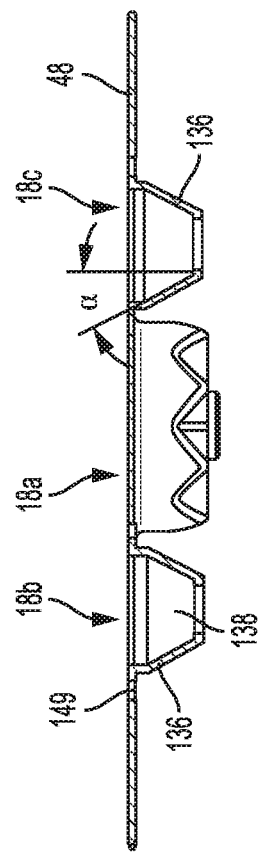
FIG. 8 is another cross-section view of the sealing membrane of the surgical access device of FIG. 1
Figure 9:
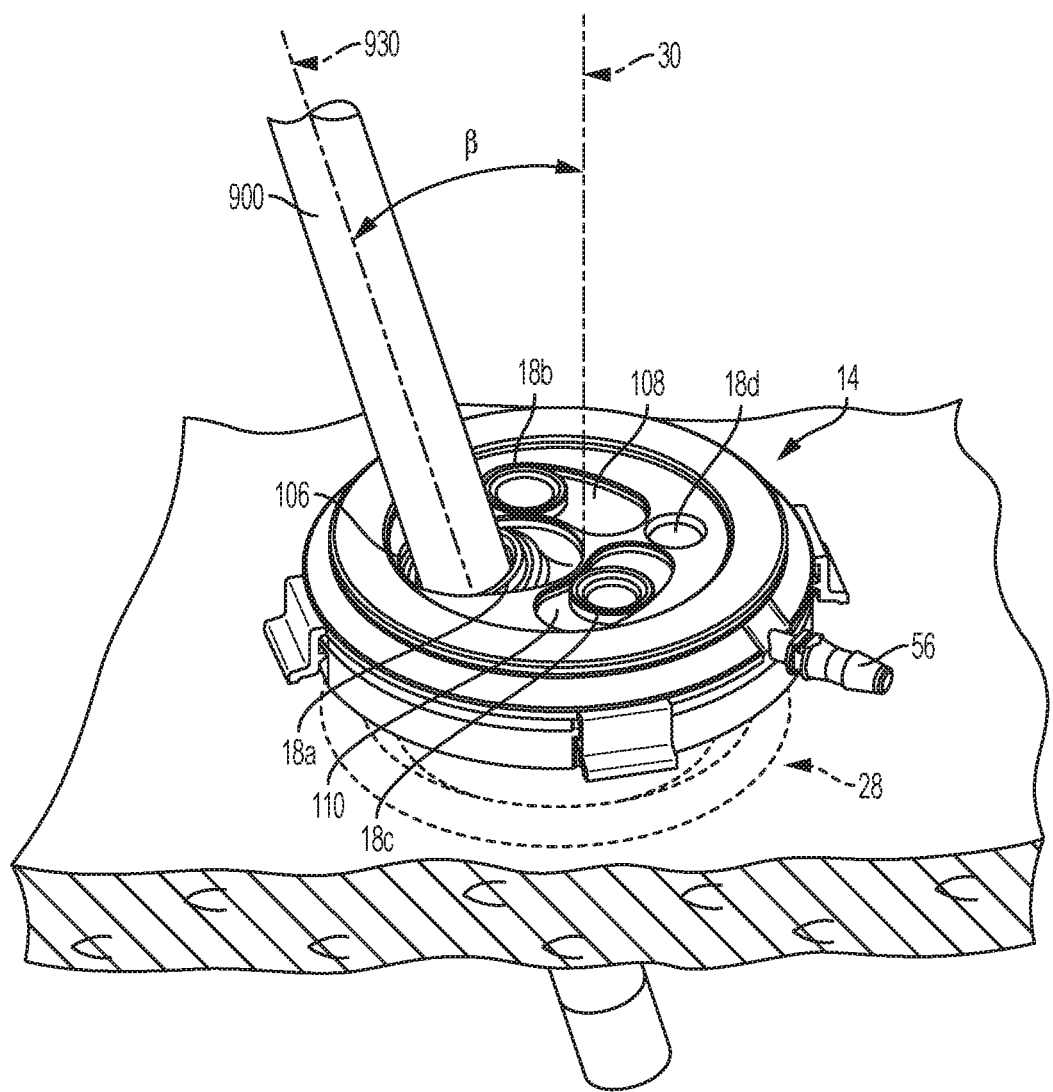
FIG. 9 is a perspective view of the surgical access device of FIG. 1 with a surgical instrument disposed through a sealing element and positioned at an angle with respect to a central longitudinal axis of the surgical access device.
Figure 10:
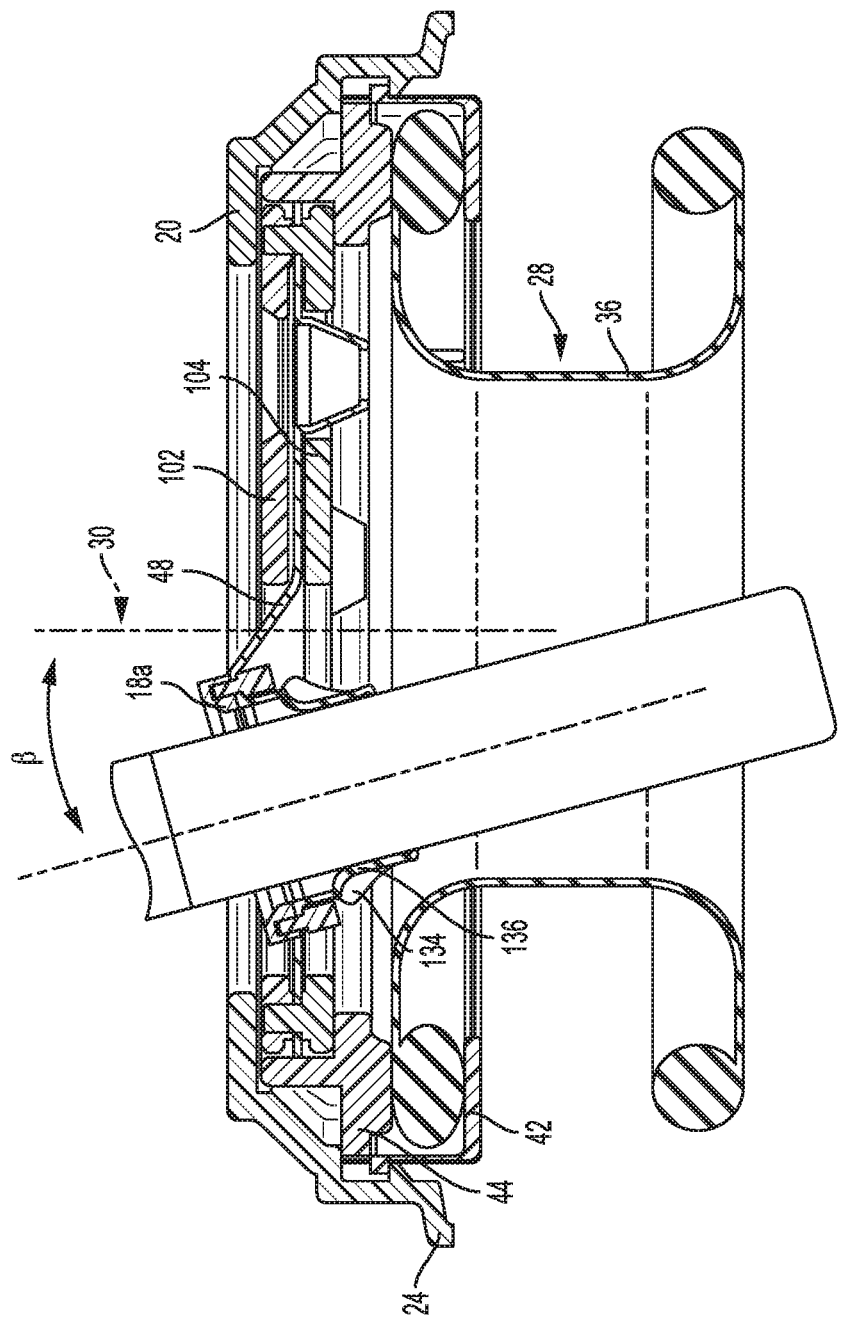
FIG. 10 is a cross-section view of the surgical access device of FIG. 1 showing a surgical instrument disposed through a sealing element and positioned at an angle with respect to the central longitudinal axis of the surgical access device.
Figure 13:
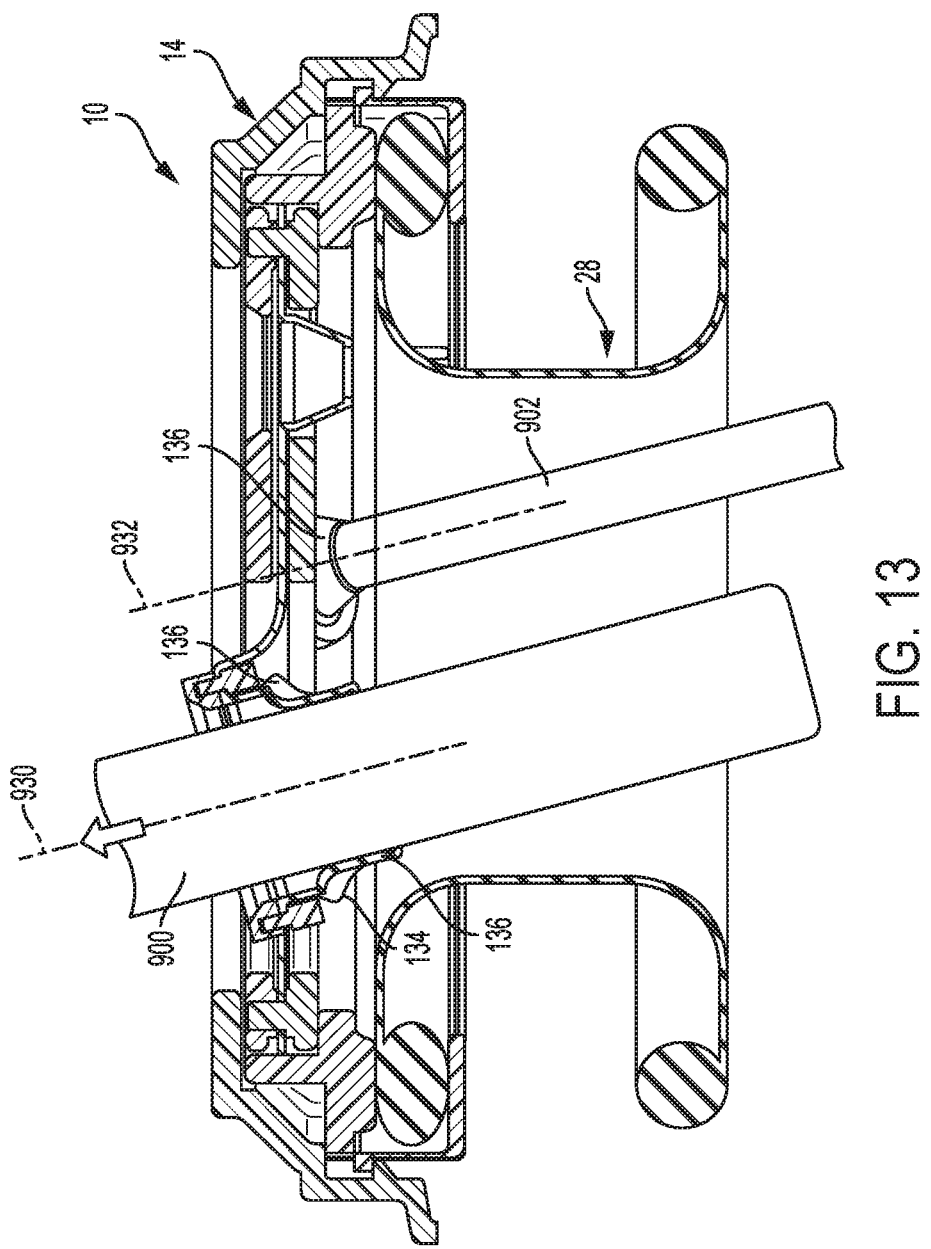
FIG. 13 is a cross-sectional view of the surgical access device of FIG. 1 showing surgical instruments disposed through the sealing elements.

The sealing elements 18 can have many configurations and constructions, but in the illustrated embodiment, the sealing elements 18 each include a sealing membrane 134, formed integrally with the sealing member 48, that is configured to form a seal around a surgical instrument positioned therethrough. The sealing membrane 134 can generally have a cone-like shape with flexible conical walls 136 and an opening 138, shown most clearly in FIGS. 5 and 6, at the apex of the cone that is smaller than a diameter of a surgical instrument such that the opening 138 can deform to form a seal around an instrument inserted therethrough. Each sealing membrane 134 can be the same as every other sealing membrane 134 or one or more sealing membranes 134 can be different than another. As shown in FIGS. 5-8, the sealing membrane 134 of sealing element 18*a* can have a fluted form in which the conical walls 136 are folded in v-shaped, accordion style folds. This construction assists in preventing eversion of the sealing membrane 134 when an instrument is withdrawn from the sealing element 18*a*. In particular, as shown most clearly in FIGS. 10 and 13, as a surgical instrument is withdrawn from the sealing element 18*a*, the fluted form bunches beneath the sealing member 48 and thus provides a bracing that prevents the sealing element 18*a* from everting. In some embodiments, the conical walls 136 of the sealing elements 18*b*, 18*c* do not have fluted forms and instead have a steep angle α relative to a lateral plane of the sealing member 48, as shown in FIG. 8, that resists eversion when a surgical instrument is withdrawn from the sealing element 18*b*, 18*c*. As will be appreciated, any of the sealing elements 18 can have one or more of the various available constructions for their respective sealing membrane 134. As will be appreciated by those skilled in the art, the sealing elements 18 can also be formed as separate elements apart from the sealing member 48 and do not have to be formed integrally therewith.

The sealing elements 18 can be constructed in various ways, but in the illustrated embodiment, the sealing elements 18 can include upper and lower seal supports 140, 142, shown most clearly in FIG. 4. The upper and lower seal supports 140, 142 can be substantially rigid rings that are configured to engage upper and lower surfaces of a perimeter of the opening 132 of the sealing member 48 therebetween. The seal supports 140, 142 serve to further define the openings formed through the sealing member 48, provide support thereto for the insertion and withdrawal of surgical instruments, and for the movable sealing elements 18*a*, 18*b*, 18*c*, can provide a structure that can move, slide, and/or otherwise travel along and within the tracks 106, 108, 110 in the upper and lower bearing plates 102, 104.

The upper and lower seal supports 140, 142 can be joined or coupled together by any method known in the art including, but not limited to, adhesives, screws, threads, etc. In the illustrated embodiment, the lower seal support 142 includes several cylindrical protrusions 144 and several elongate protrusions 146 formed around its circumference and extending in a proximal direction from its proximal surface 148. The cylindrical protrusions 144 can extend through corresponding openings 149 formed around a circumference of the sealing element openings 132 in the sealing member 48 and into corresponding openings 152 within the upper seal supports 140. The elongate protrusions 146 can extend through corresponding elongate slots 150 formed adjacent to the circumference of the sealing element openings 132 formed in the sealing member 48. In this way, a circumference surrounding each sealing membrane 134 is clamped, coupled, or otherwise secured between the upper and lower seal supports 140, 142. When mated together, the sealing elements 18 are able to form an air and gas tight seal around a surgical instrument inserted therethrough while the sealing member 48 seals the rest of the working channel between the upper bearing plate 102 and the interior of a body.

Referring now to FIGS. 9-13, exemplary movement and positioning variations and configurations of the movable sealing elements 18*a*, 18*b*, 18*c* are illustrated. As noted above, the sealing member 48 is flexible and thus will stretch, bunch, twist and otherwise deform in response to movement of the various sealing elements 18*a*, 18*b*, 18*c* within the upper and lower bearing plate tracks 106, 108, 110. More particularly, because the upper and lower seal supports 140, 142 grasp the sealing member 48 around the sealing membranes 134, the sealing elements 18*a*, 18*b*, 18*c* are able to pull and push the sealing member 48 in response to movement of surgical instruments disposed therein.

Figure 11:
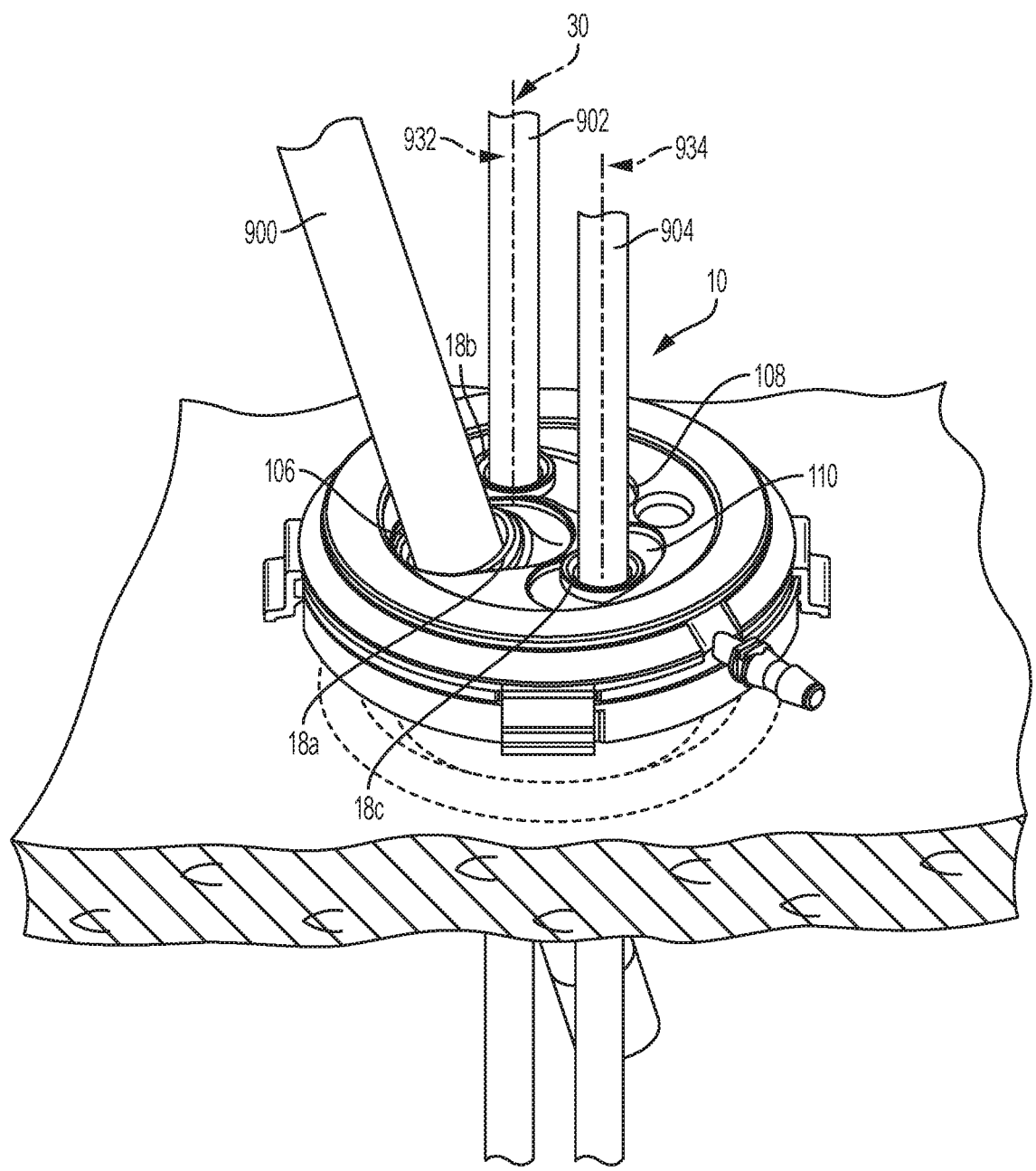
FIG. 11 is a perspective view of the surgical access device of FIG. 1 disposed in tissue and having three surgical instruments disposed through three sealing elements.
Figure 12:
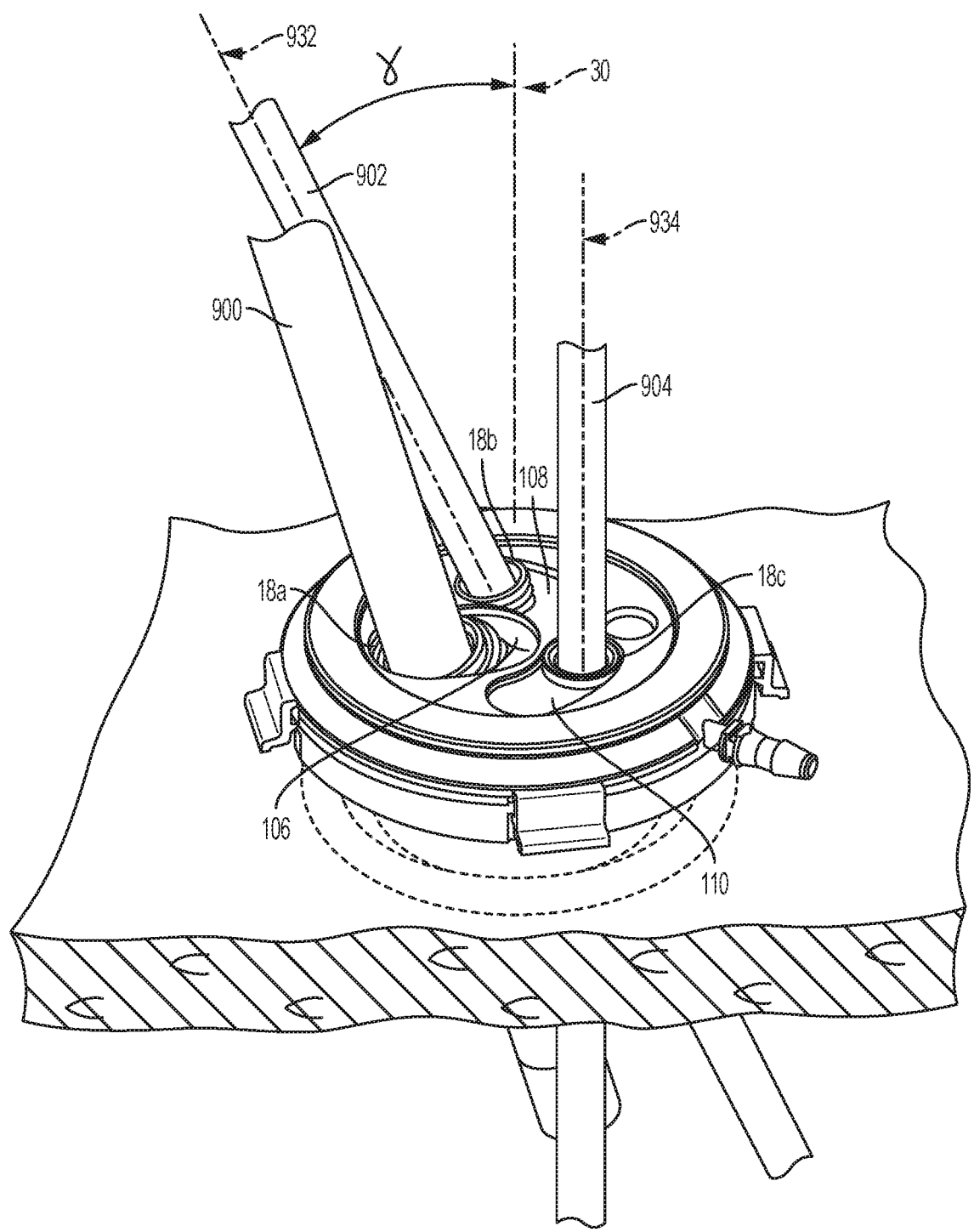
FIG. 12 is a perspective view of the surgical access device of FIG. 1 disposed in tissue and having three surgical instruments disposed through three sealing elements at various angles.

In the illustrated embodiment, the sealing elements 18*a*, 18*b*, 18*c* are each independently movable laterally within and along the length and/or width of their respective bearing plate tracks 106, 108, 110. Each of the sealing elements 18*a*, 18*b*, 18*c* can independently and selectively be moved laterally from an initial resting position, such as a relatively center position in the tracks 106, 108, 110 to either of opposed ends of the tracks 106, 108, 110, and anywhere in between, whether along a straight line of a track 106 or along a curved path that follows the curve of tracks 108, 110. In the initial position, the seal member 48 is not stretched, and in the moved position, the seal member 48 stretches to allow a seal to be maintained. The tracks 106, 108, 110 containing each sealing element 18*a*, 18*b*, 18*c* define the predetermined path of movement allowed. For example, in FIGS. 9, 11, and 12 a surgical instrument 900 is inserted through the sealing element 18*a*, which is moved from its natural, center position within the track 106 to one end of the track 106 near the outer circumference of the device 10. In addition, as shown in FIGS. 11 and 12, a surgical instrument 902 is positioned within sealing element 18*b*, which is also moved from its natural, center position in the track 108 to one end of the track 108. A surgical instrument 904 is positioned within the sealing element 18*c* and is positioned in a center portion of the track 110 in FIG. 11 and is moved to one end of the track 110 in FIG. 12. Accordingly, some variations of the possible lateral movement of the sealing elements 18*a*, 18*b*, 18*c* within their respective tracks 106, 108, 110 can be seen. Of course, many other variations and combinations of lateral movement are also possible.

Each sealing element 18*a*, 18*b*, 18*c* can also be moved angularly within each track 106, 108, 110 such that a longitudinal axis of the sealing element 18*a*, 18*b*, 18*c* is movable and adjustable relative to the central longitudinal axis 30 of the housing 12. The sealing elements 18*a*, 18*b*, 18*c* can be pivoted out of a lateral plane of the tracks 106, 108, 110 within the base member 16. The sealing member 48 can stretch and bunch around each sealing element 18*a*, 18*b*, 18*c* to enable each sealing element 18*a*, 18*b*, 18*c* to be pivoted to an angle with respect to the lateral plane while maintaining a seal around an instrument inserted therethrough. In the illustrated embodiments, the sealing elements 18*a*, 18*b*, 18*c* are angularly adjustable at any position along a lateral, long-axis of the elongate tracks 106, 108, 110. For example, in FIGS. 9 and 10, a central longitudinal axis 930 of the sealing element 18*a*, in which the surgical instrument 900 is disposed, is positioned at an angle β with respect to the central longitudinal axis 30 of the housing 12. As shown in FIGS. 11 and 12, the sealing element 18*b*, in which the surgical instrument 902 is disposed, is moved from a position in which its central longitudinal axis 932 is parallel with the central longitudinal axis 30 of the housing 12 (FIG. 11) to a position in which its central longitudinal axis 932 is at an angle γ with respect to the central longitudinal axis 30 of the housing 12 (FIG. 12). At the same time, a central longitudinal axis 934 of the sealing element 18*c* remains parallel with the central longitudinal axis 30 of the housing 12 in both configurations. The above described variations in angular adjustment are just a few of the many configurations possible. All of the sealing elements 18*a*, 18*b*, 18*c* are completely and independently angularly adjustable within their respective tracks 106, 108, 110 at any lateral position within the tracks 106, 108, 110. For example, the sealing elements 18*a*, 18*b*, 18*c* can be angularly adjustable at any position along both a long-axis and a short-axis of the elongate tracks 106, 108, 110, and/or angularly adjustable at any position around 360 degrees laterally within the tracks 106, 108, 110.

The sealing elements 18a, 18b, 18c can also be moved vertically relative to the base member 16 and parallel relative to the central longitudinal axis 30 of the housing 12. As noted above, in some embodiments, the lips formed in the lower bearing plate tracks 106b, 108b, 110b can prevent vertical movement below the bearing plate tracks 106b, 108b, 110b, while vertical movement above the upper bearing plate tracks 106a, 108a, 110a is allowed. Thus, a surgical instrument disposed within a sealing element 18a, 18b, 18c can be pulled proximally from the sealing element 18a, 18b, 18c, whether for complete withdrawal or for adjustment purposes, and the movement can lift the sealing elements 18a, 18b, 18c above the plane of the base member 16. In other embodiments, vertical movement is allowed in both directions above and below the bearing plate tracks 106, 108, 110.

As will be appreciated by those skilled in the art, combinations of any of the lateral, angular, and vertical movement is also allowed. A particular sealing element 18a, 18b, 18c can be independently moved laterally within a track 106, 108, 110 while its central longitudinal axis is at an angle relative to the central longitudinal axis 30 of the housing 12. In addition, a particular sealing element 18a, 18b, 18c can be independently moved vertically while its central longitudinal axis is at an angle relative to the central longitudinal axis 30 of the housing 12. Such vertical movement is thus no longer strictly parallel to the central longitudinal axis 30 of the housing 12, but is instead movement that is at an angle relative to the central longitudinal axis 30 of the housing 12. Any and all combinations of independent lateral, angular, and vertical movement of each movable sealing element 18a, 18b, 18c is accomplished due to the flexibility of the sealing member 48 being configured to stretch, twist, bunch, and otherwise deform in response to the movement. In addition, all such movement is performed while the working channel is sealed due to the seal formed by the sealing elements 18a, 18b, 18c around a surgical instrument inserted therethrough and due to the flexibility of sealing member 48 that able to maintain a seal during deformation.

As noted above, the base member 16 can also be rotated within and relative to the base member support 44, and thus relative to the housing 12. Accordingly, the base member 16 provides multiple ways in which the sealing elements 18 can be moved to provide better access for surgical instruments inserted therein. By rotating the base member 16, the sealing elements 18 can all be rotated as a collective unit around the central longitudinal axis 30 of the housing 12. In addition, each sealing element 18a, 18b, 18c can be moved laterally, angularly, and vertically within the base member 16, as described above, to enable better access and maneuverability.

Figure 14:
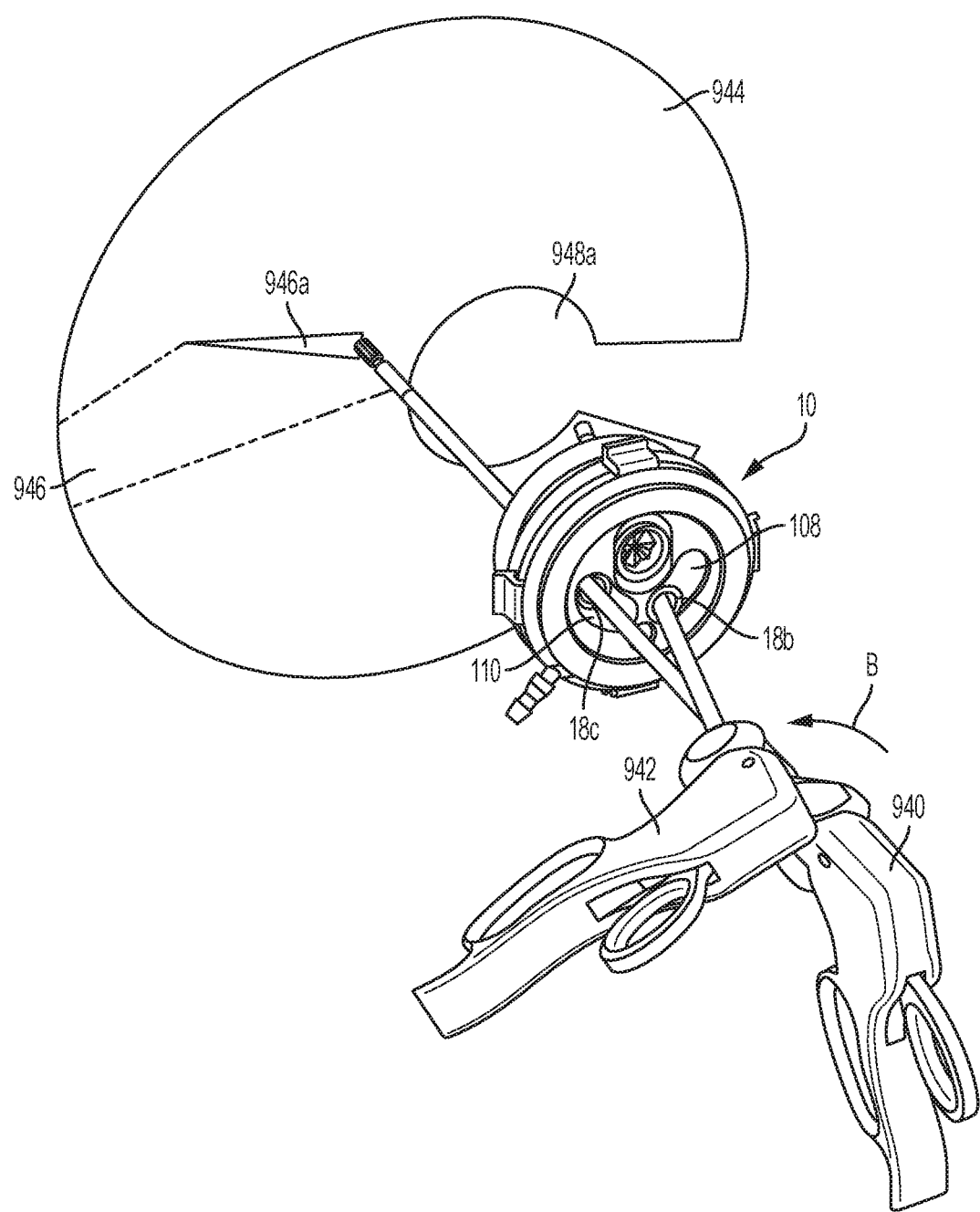
FIG. 14 is a perspective view illustrating a first range of motion of the surgical access device of FIG. 1.
Figure 15:
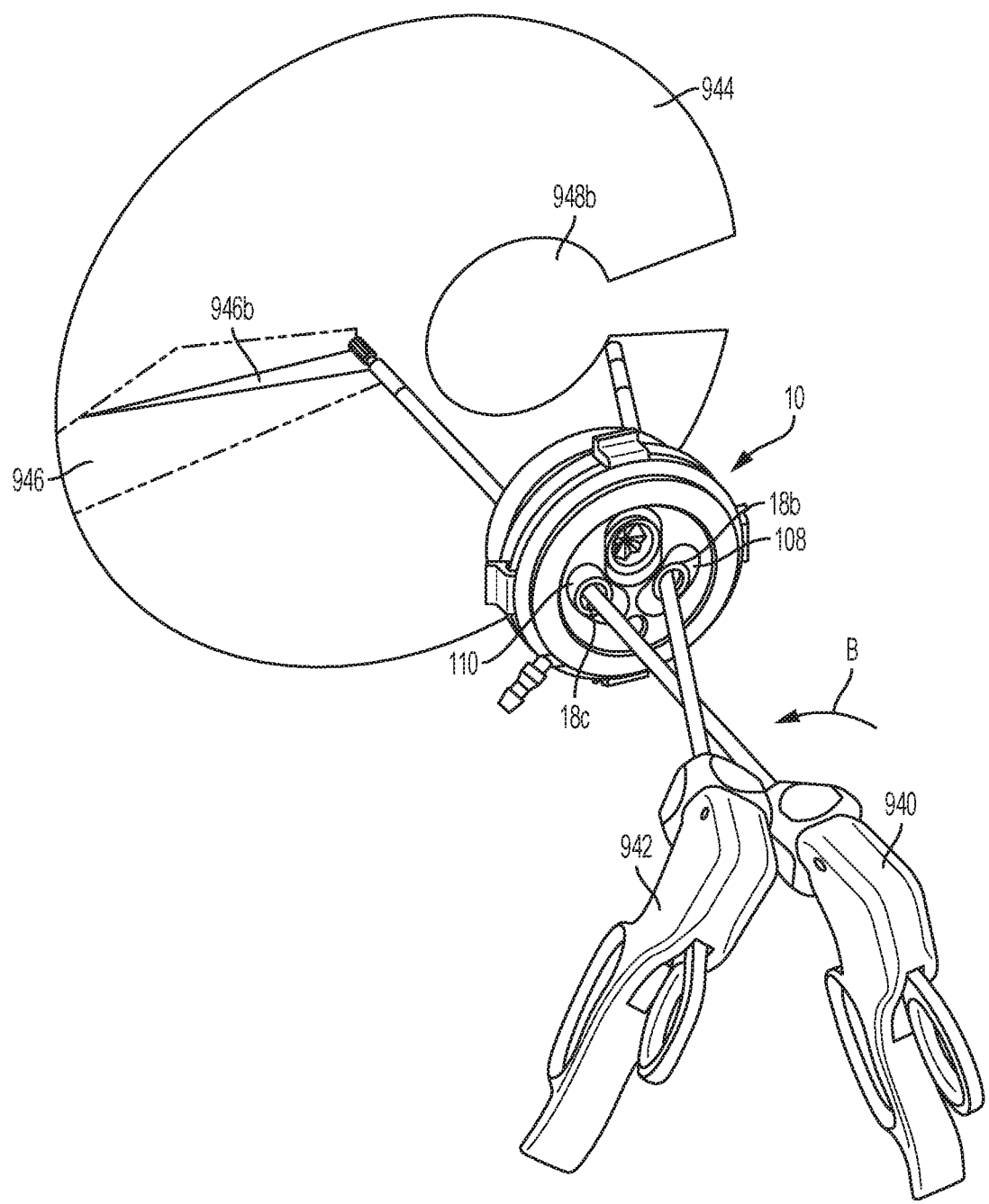
FIG. 15 is a perspective view illustrating a second range of motion of the surgical access device of FIG. 1.
Figure 16:
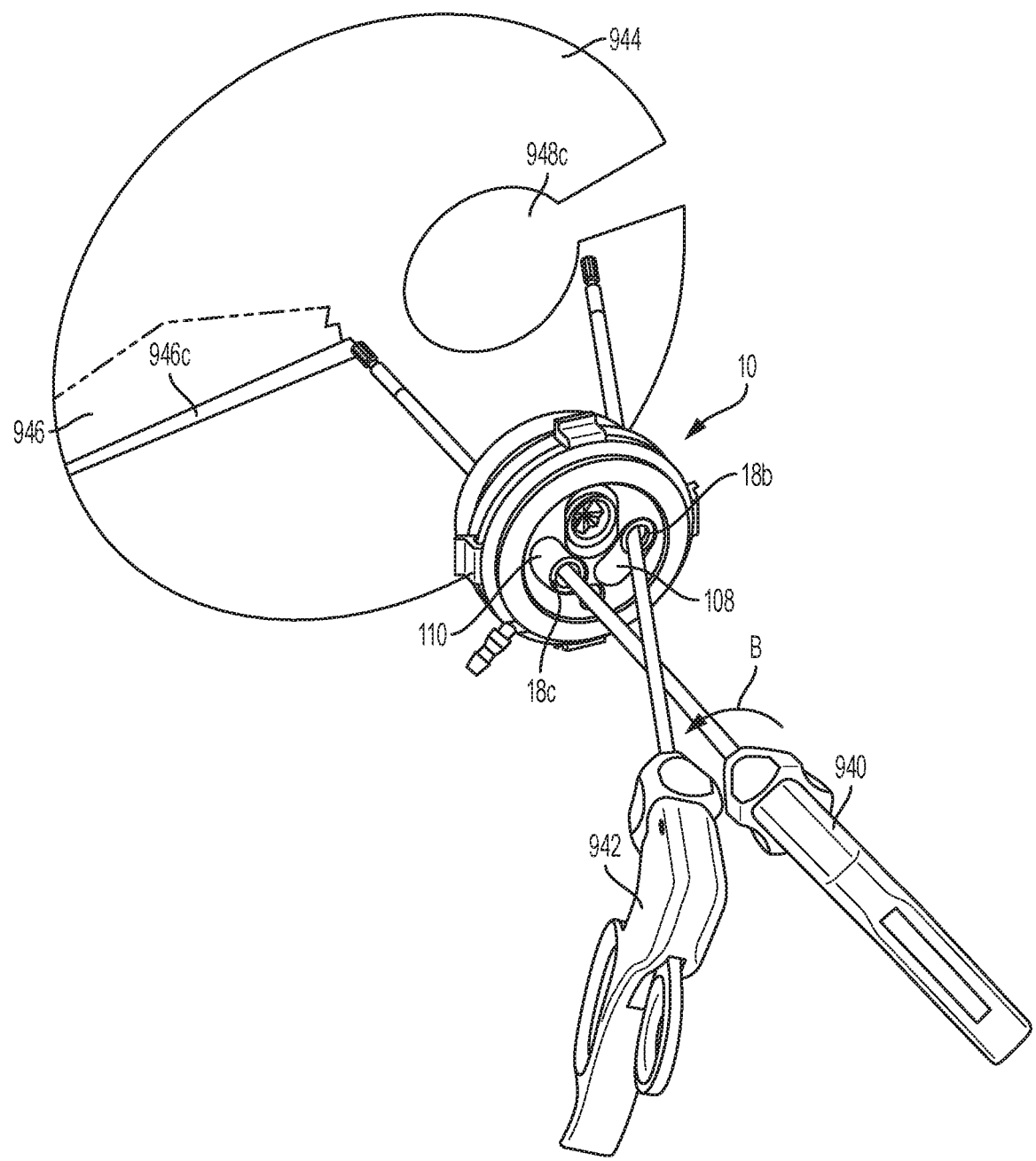
FIG. 16 is a perspective view illustrating a third range of motion of the surgical access device of FIG. 1.
Figure 17:
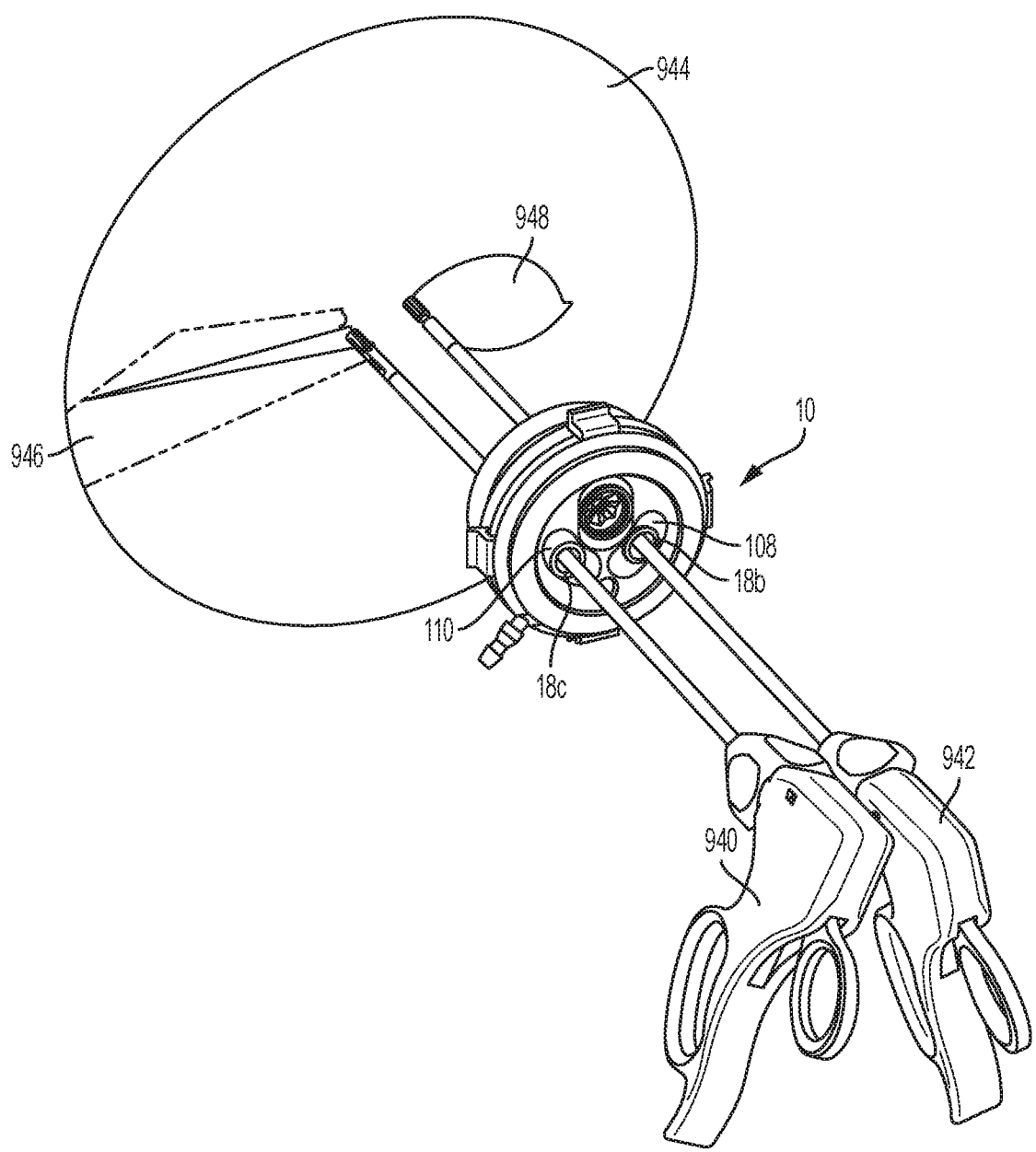
FIG. 17 is a perspective view illustrating all three ranges of motion of FIGS. 17-19.

FIGS. 14-17 illustrate one embodiment of the range of motion that the surgical access device 10 can provide during surgical procedures. In particular, FIGS. 14-16 illustrate a series of possible ranges of motion for various positions of the sealing elements 18. FIG. 17 combines the three series shown in FIGS. 14-16 to give a complete picture of one embodiment of the range of motion possible with the surgical access device 10. In all illustrations, an assumption is made that a first surgical instrument 940, disposed through the sealing element 18c, remains perpendicular to a lateral axis or a lateral surface of the housing 12 as a second surgical instrument 942, disposed through the sealing element 18b, is moved through various angles relative to the lateral axis or the lateral surface of the housing 12.

In FIG. 14, a target diameter 944 is illustrated and represents the target space over which one or both of the first and second surgical instruments 940, 942 can move during a surgical procedure. The first surgical instrument 940 is positioned through the sealing element 18c, which is positioned at a left-hand end of the track 110. The second surgical instrument 942 is positioned through the sealing element 18b, which is positioned at a left-hand end of the track 108. The two sealing elements 18c, 18b are positioned at the same, left-hand end of the tracks 110, 108. In this position, there is a triangular shaped space 946a behind the surgical instrument 940 that cannot be accessed by any angular movement of the second instrument 942. As the second surgical instrument 942 is moved through its entire angular range, it will pass over the first surgical instrument 940, as illustrated by the arrow B. A key-hole shape 948a is also shown and generally illustrates the area over which the instrument 942 cannot reach while in this lateral position within the track 108 due to, for example, handle and shaft interference between the two instruments 940, 942. Thus, the entire target diameter 944, minus the triangle 946a and the key-hole shape 948a, can be reached by the second surgical instrument 942 during a surgical procedure while the sealing elements 18c, 18b are in the far, left-hand end position within their tracks 110, 108.

In FIG. 15, the target diameter 944 is again illustrated. The first surgical instrument 940 is positioned through the sealing element 18c, which is positioned at a center portion of the track 110. The second surgical instrument 942 is positioned through the sealing element 18b, which is positioned at a center portion of the track 108. In this position, there is a triangular shaped space 946b behind the first surgical instrument 940 that cannot be accessed by any angular movement of the second surgical instrument 942. As the second surgical instrument 942 is moved through its entire angular range, it will pass over the first surgical instrument 940, as illustrated by the arrow B. A key-hole shape 948b is also shown and generally illustrates the area over which the second surgical instrument 942 cannot reach while in this center, lateral position within the track 108 due to, for example, handle and shaft interference between the two instruments 940, 942. Thus, the entire target diameter 944, minus the triangle 946b and the key-hole shape 948b, can be reached by the surgical instrument 942 while the sealing elements 18c, 18b are in center positions within their respective tracks 110, 108.

In FIG. 16, the target diameter 944 is again illustrated. The first surgical instrument 940 is positioned through the sealing element 18c, which is positioned at a right-hand end of the track 110. The second surgical instrument 942 is positioned through the sealing element 18b, which is positioned at a right-hand end of the track 108. The two sealing elements 18c, 18b are positioned at the same, right-hand end of the tracks 110, 108. In this position, there is a triangular shaped space 946c behind the first surgical instrument 940 that cannot be accessed by any angular movement of the second surgical instrument 942. As the second surgical instrument 942 is moved through its entire angular range, it will pass over the first surgical instrument 940, as illustrated by the arrow B. A key-hole shape 948c is also shown and generally illustrates the area over which the second surgical instrument 942 cannot reach while in this lateral position within the track 108 due to, for example, handle and shaft interference between the two instruments 940, 942. Thus, the entire target diameter 944, minus the triangle 946c and the key-hole shape 948c, can be reached by the second surgical instrument 942 during a surgical procedure while the sealing elements 18c, 18b are in the far, right-hand end position within their tracks 110, 108.

As noted above, FIG. 17 represents the combination of FIGS. 14-16 to illustrate one embodiment of the full range of motion available during a surgical procedure to the second surgical instrument 942 disposed through the surgical access device 10. The target diameter 944 is again shown. An area 946, enclosed by dotted lines, represents the combination of triangles 946a, 946b, 946c and is essentially an area where a small portion of the target diameter 944 becomes unavailable to the second surgical instrument 942 at each lateral position within the track 108 due to, for example, interference between the two shafts. An area 948 is a combination of the key-holes 948a, 948b, 948c and is the only area within the target diameter 944 that can be unavailable to the second surgical instrument 942 during a surgical procedure. Accordingly, almost the entire target diameter 944 is accessible to the second surgical instrument 942, while another surgical instrument 940 is disposed through the surgical access device 10, just by moving the second surgical instrument 942 along the track 108 and through the various possible angular orientations. Of course, the inaccessible area 948 is accessible by another surgical instrument disposed through the sealing element 18c and/or 18a. In addition, as noted above, the base member 16 is rotatable relative to the rest of the housing 12, and thus with a slight rotation of the base member 16, the second surgical instrument 942 can access the area 948. Additionally, the entire housing 12 is rotatable relative to the retractor 28, providing a similar type of access to the second surgical instrument 942. As will be appreciated, this series of range of motion illustrations is only one example of many possible ranges of motion that the surgical access device 10 can provide.

Figure 18:
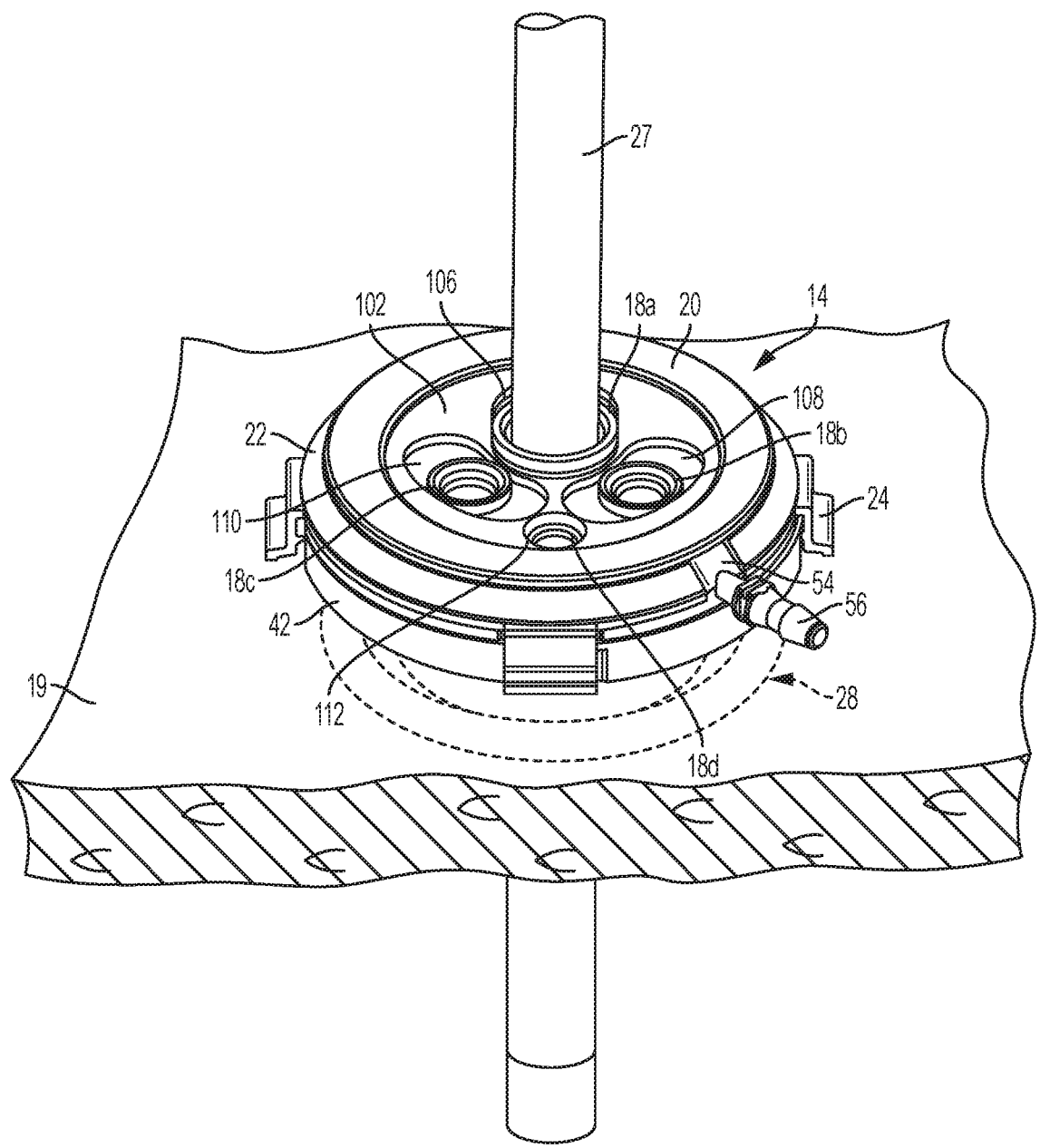
FIG. 18 is a perspective view of the surgical access device of FIG. 1 disposed in tissue with a surgical instrument disposed within a sealing element.
Figure 19:
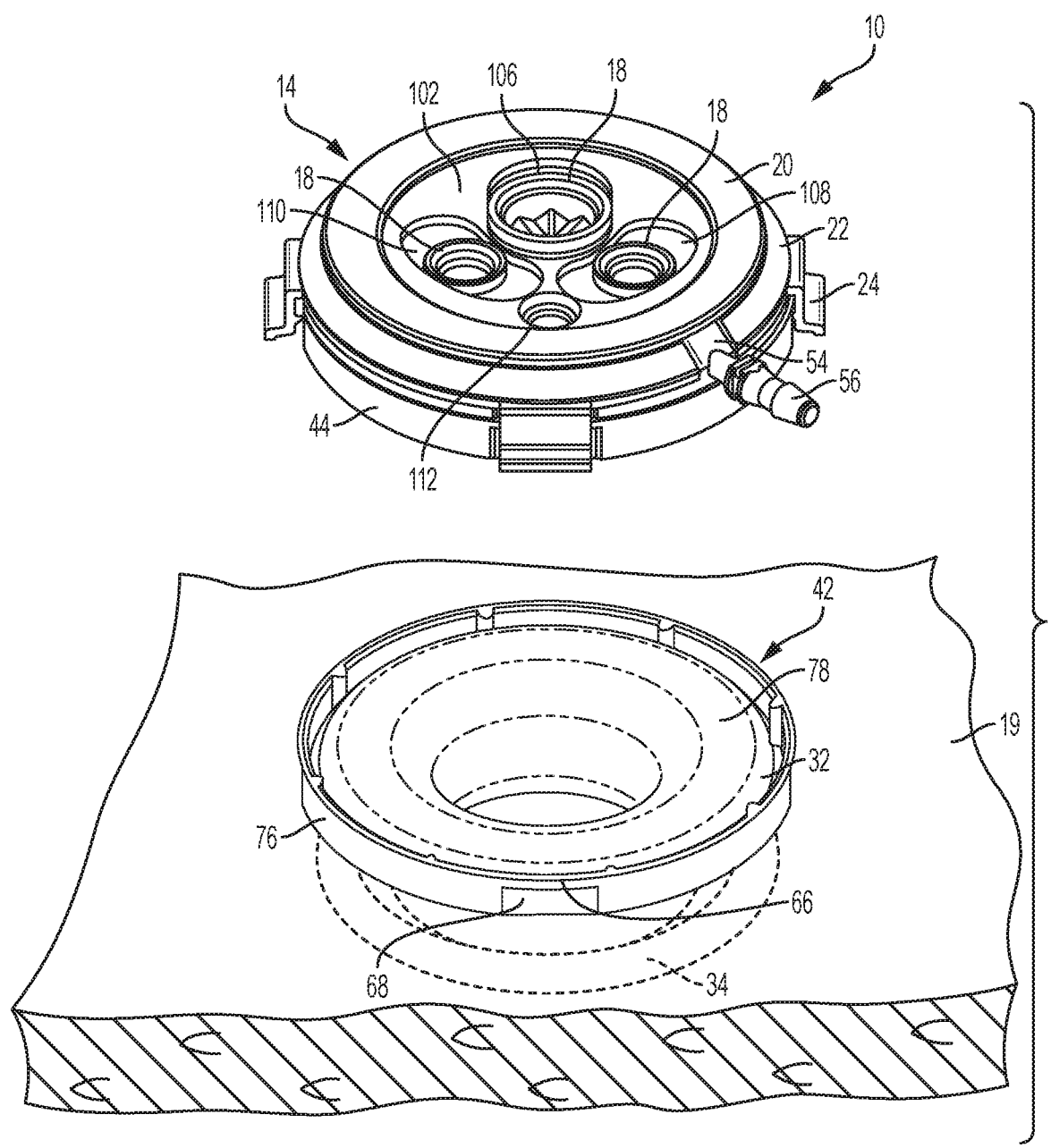
FIG. 19 is a perspective view of a housing support and a retractor of the surgical access device of FIG. 1 disposed in tissue with a top portion of the housing detached therefrom.
Figure 20:
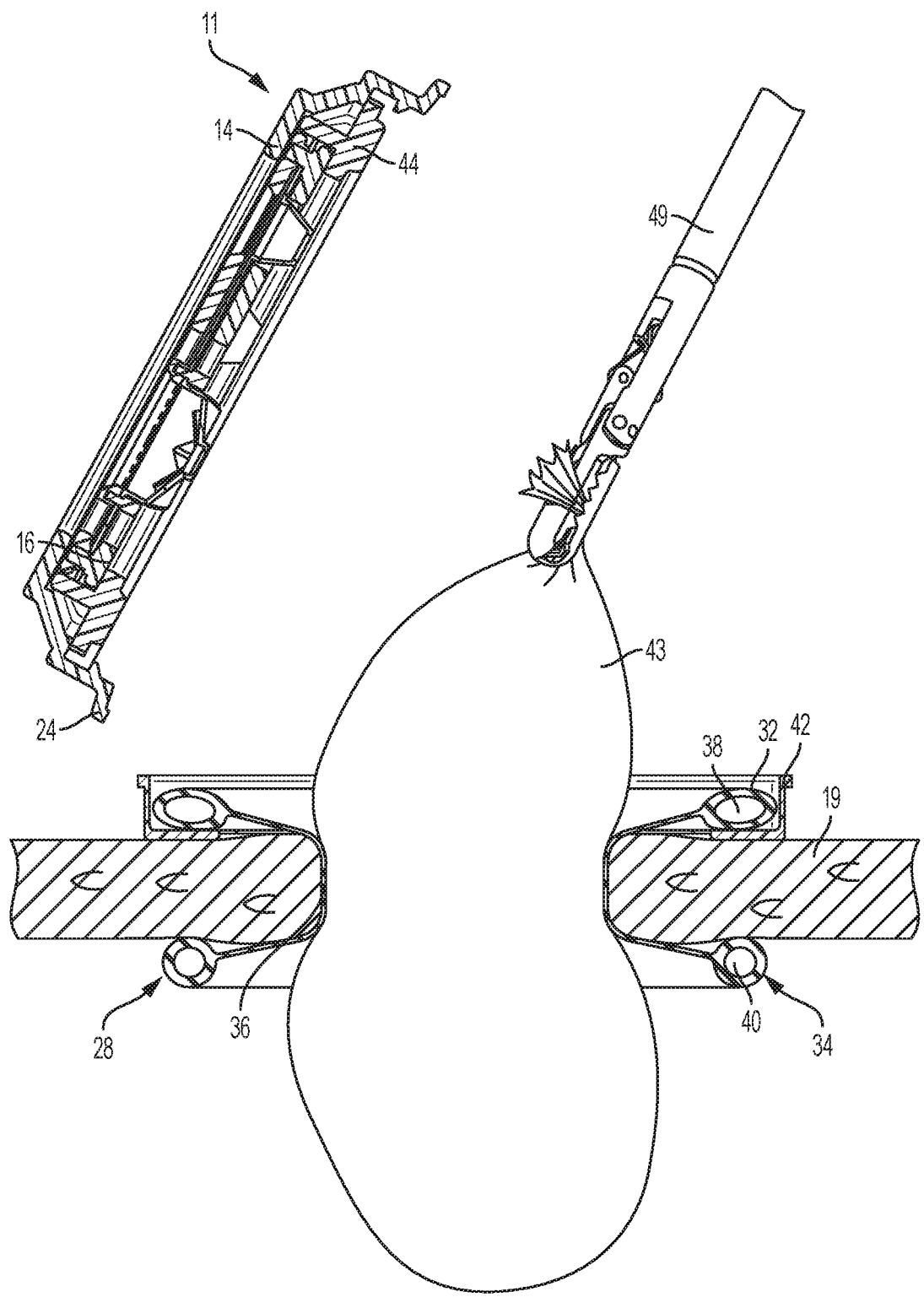
FIG. 20 is a cross-sectional view of tissue being removed through the retractor and the housing support of the surgical access device of FIG. 1.
Figure 21:
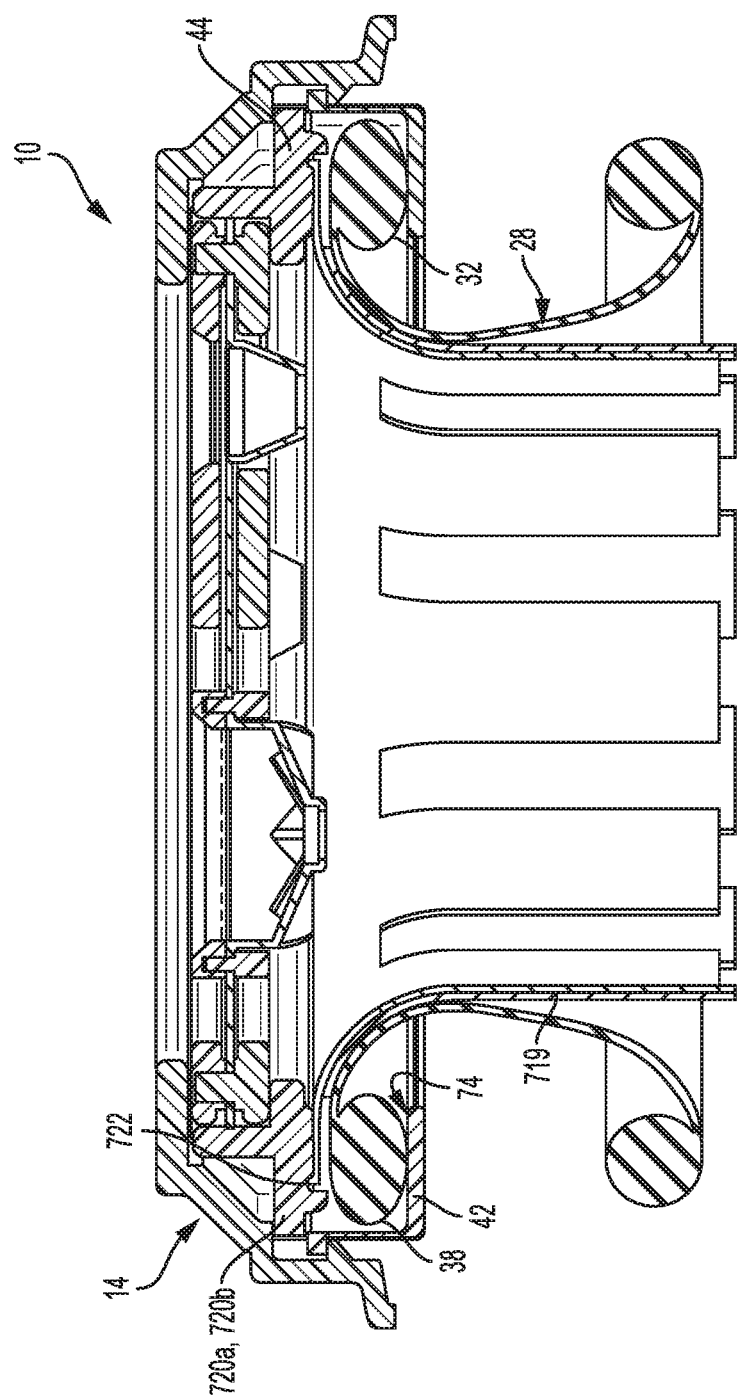
FIG. 21 is a cross-sectional view of the surgical access device of FIG. 1 including one embodiment of a safety shield.
Figure 22:
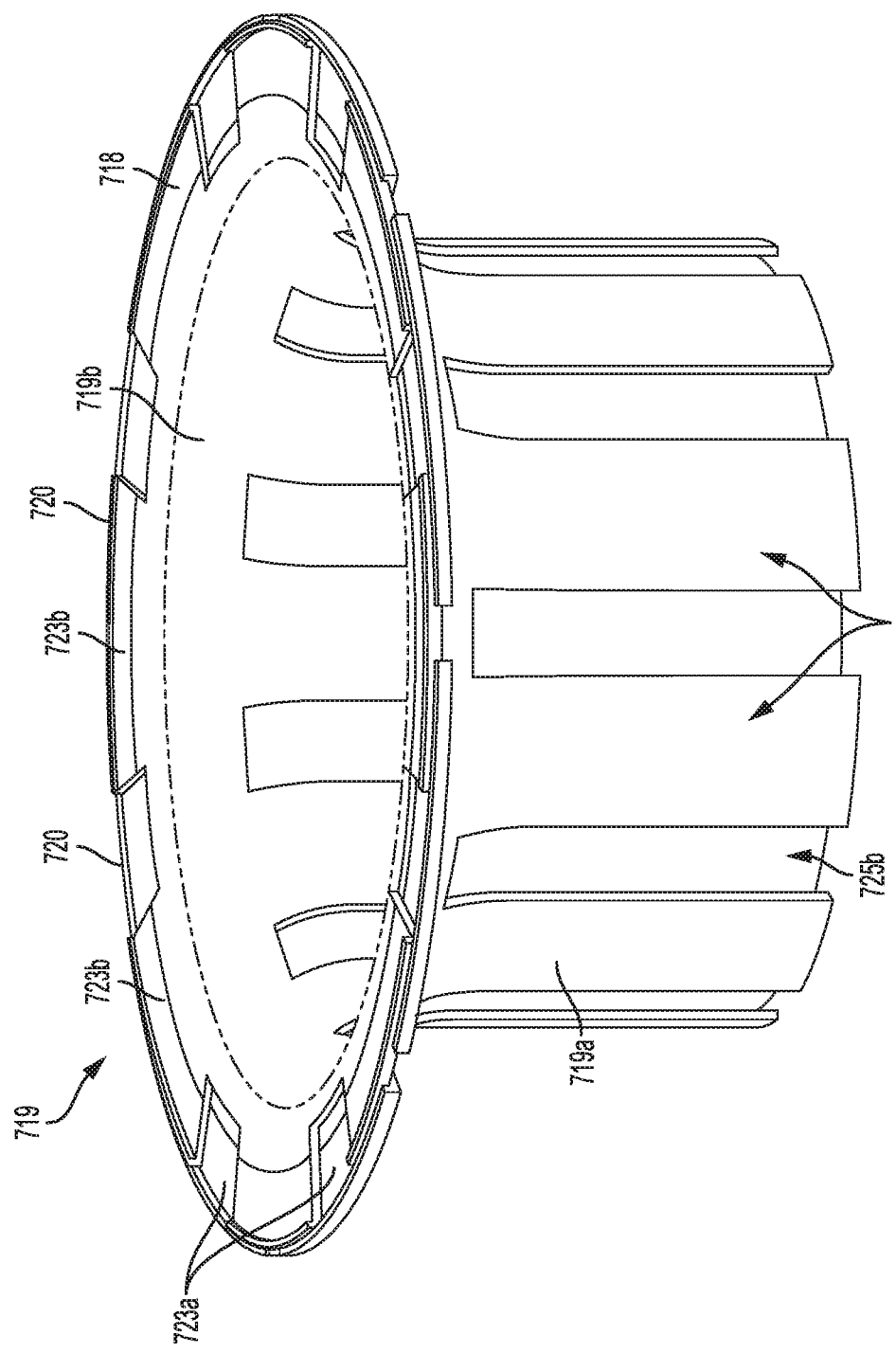
FIG. 22 is a perspective view of the safety shield of FIG. 21.
Figure 23:
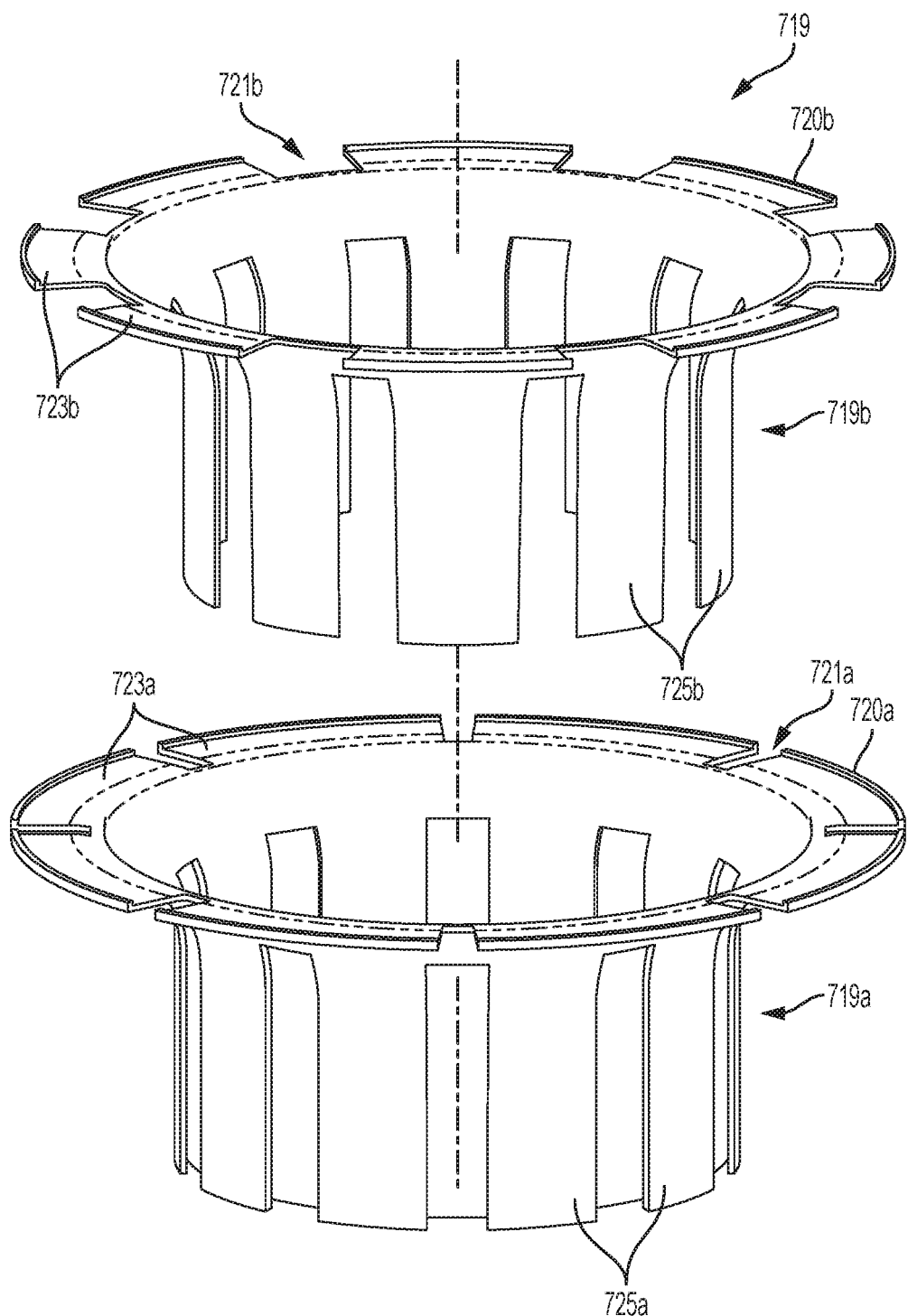
FIG. 23 is an exploded view of the safety shield of FIG. 21.

In use, as shown in FIGS. 18-20, the retractor 28 of the exemplary access device 10 can be positioned within any opening in a patient's body, including natural openings and surgically formed openings. In the illustrated embodiment, the retractor is positioned through an opening within tissue 19. The retractor 28 is held in place by the tissue 19 within the opening such that the housing 12 is positioned against an outer surface of the patient's body. Before insertion of any surgical instruments into the housing 12, the housing 12 can be rotated in either direction by any amount relative to the retractor 28 to enable proper positioning of the sealing elements 18. Once a proper position is achieved, various surgical instruments, for example surgical instrument 27, can be inserted through the movable and immovable sealing elements 18 disposed within the housing 12 and into the working channel of the surgical access device.

In the illustrated embodiment, one sealing element 18a has a diameter than is larger than the other sealing elements 18b, 18c, 18d. Thus, the sealing element 18a can receive the surgical instrument 27 having a larger diameter, such as an endoscopic camera and/or light. In addition, in the illustrated embodiment, the immovable sealing element 18d has a diameter smaller than the other sealing elements 18a, 18b, 18c and can receive an instrument with a smaller diameter, for example, a surgical retractor. The other two movable sealing elements 18b, 18c can receive any number of other surgical instruments as may be needed in a particular application. A person skilled in the art will appreciate that the sealing elements 18 can have various diameter and that any surgical instrument having a suitable diameter can be inserted in any one of the various sealing elements.

Once surgical instruments are disposed within the sealing elements 18 as needed, insufflation of the interior surgical site can be achieved by flowing an insufflation gas through the insufflation port 56 and into the sealed working channel. The surgical instruments within the sealing elements 18a, 18b, 18c can then be moved laterally, angularly, and vertically, as described above, to achieve optimal positioning of the surgical instruments within the interior surgical site. In addition, the base member 16 can be rotated relative to the base member support 44 and the housing 12 to rotate all of the sealing elements 18, and the instruments disposed in the sealing elements 18, as a collective unit. The housing 12 can also be rotated as needed to achieve better positioning for, for example, the insufflation port 56. During the surgical procedure, the surgical instruments disposed in the sealing elements 18 can be repeatedly and independently moved and manipulated within their respective tracks 106, 108, 110 to facilitate ease of use.

Upon completion of a surgical procedure, insufflation pressure can be released through the insufflation port 56, and the surgical instruments can be withdrawn from the sealing elements. Using the latches 24, a top portion 11 of the housing 12, including the housing cover 14, the base member 16, and the base member support 44, can be unlatched and removed from the housing support 42, as shown most clearly in FIG. 20. The retractor 28 remains within the opening in the tissue 19 and the housing support 42 remains adjacent to the tissue 19 on an exterior thereof. Tissue 43 that was cut or dissected during the surgical procedure can be withdrawn through the working channel of the retractor 28 as needed using a surgical instrument 49. The retractor 28 can then be removed from the opening in the tissue 19 upon completion of the procedure. As will be appreciated, the top portion 11 of the housing 12 can also be latched back to the housing support 42 as needed if further surgical procedures are required.

In some embodiments, such as that shown in FIGS. 21-28, the surgical access device 10 can also include a shield 719 configured to extend through the retractor 28 to thereby provide a protective lining as surgical instruments are inserted through the device 10. The shield 719 can have a length corresponding to a length of the retractor 28, but can also have a length less than or considerably longer than the length of the retractor depending on a specific application. The shield 719 can be mated to the retractor 28 using any attachment mechanism, e.g., adhesive, screws, press fit, etc., as will be appreciated by a person skilled in the art. As illustrated, the shield 719 can be configured to engage a proximal flange 32 of the retractor 28 that is seated in the housing support 42 and the distal surface 86 of the base member support 44. The proximal o-ring 38 within the flange 32 can help provide structure to the proximal flange 32 and therefore help provide a more stable engagement surface for the shield 719. Lips 720a, 720b can be formed around an outer circumference of a proximal rim 718 of the shield 719 and can fit within and engage a recess 722 formed in the distal surface 86 of the base member support 44 to provide further securement of the shield 719 between the proximal flange 32 and the base member support 44.

The shield 719 can have any size, shape, and configuration. In this illustrated embodiment, the shield 719 includes a circumferentially expandable, cylindrically-shaped member having an outer layer 719a and an inner layer 719b configured to be disposed within in the outer layer 719a. The outer and inner layers 719a, 719b can each respectively include a circumferential proximal rim 721a, 721b having a plurality of flanges 723a, 723b extending radially outward therefrom. The outer and inner layers 719a, 719b can include any number of flanges 723a, 723b, and the flanges 723a, 723b can be spaced equidistantly or any other distance apart from one another around their respective proximal rims 721a, 721b. The outer and inner flanges 723a, 723b can each be configured to at least partially overlap to form a continuous proximal flange of the shield 719 that is configured to engage the proximal flange 32 of the retractor 28. Alternatively, as shown, a portion of the outer and inner flanges 723a, 723b can be configured to engage one another to form a "broken" proximal flange of the shield 719. In other embodiments, none of the outer and inner flanges 723a, 723b can overlap one another when the inner layer 719b is disposed in the outer layer 719a.

The outer and inner layers 719a, 719b of the shield 719 can also include a plurality of respective distal elongate fingers 725a, 725b distally extending from the proximal rim 721a, 721b and configured to at least partially overlap and engage one another when the inner layer 719b is disposed in the outer layer 719a to form a continuous distal surface configured to engage at least a portion of an inner wall of the inner elongate portion 36 of the retractor 28. The distal fingers 725a, 725b can thus be configured to protect the inner elongate portion 36 of the retractor 28 from damage but be configured to be selectively movable when in contact with a surgical instrument such that the surgical instrument can optionally push between the distal fingers 725a, 725b to help provide the surgical instrument with free angular range of motion through the device 10. The distal fingers 725a, 725b can also be configured to be selectively movable when the retractor 28 bends when in position in tissue, if the retractor 28 is flexible.

Figure 24:
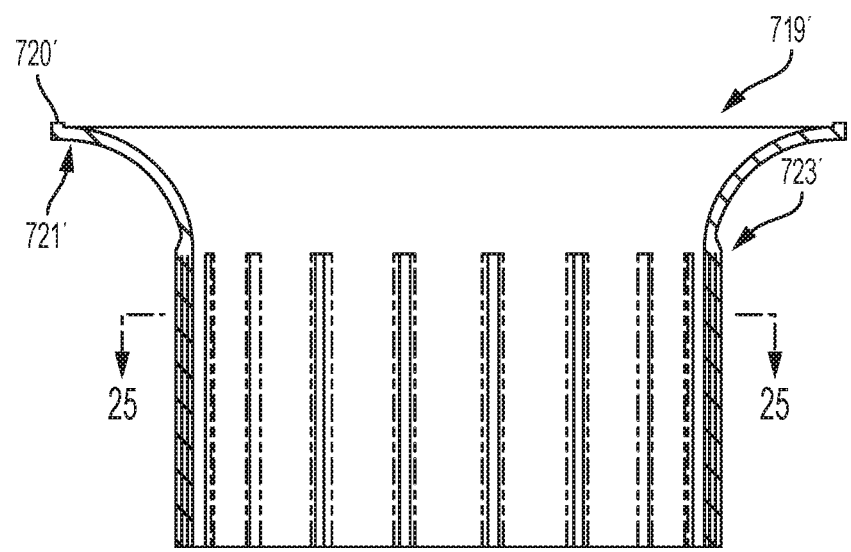
FIG. 24 is a cross-sectional side view of a second embodiment of a safety shield.
Figure 25:
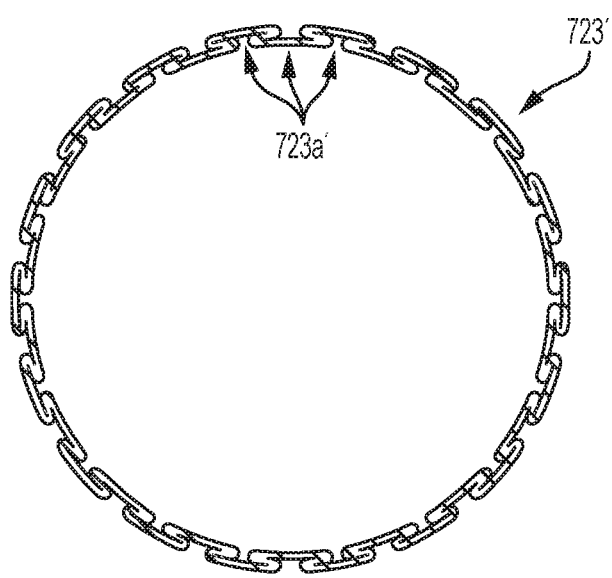
FIG. 25 is a cross-sectional top view of the safety shield of FIG. 24.
Figure 26:
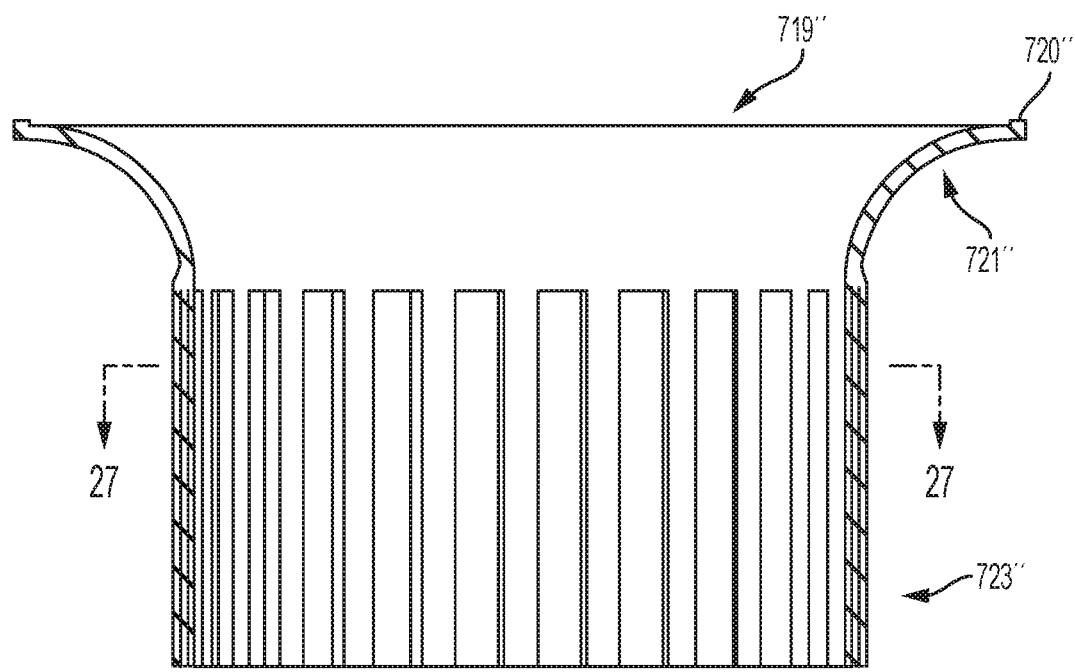
FIG. 26 is a cross-sectional side view of a third embodiment of a safety shield.
Figure 27:
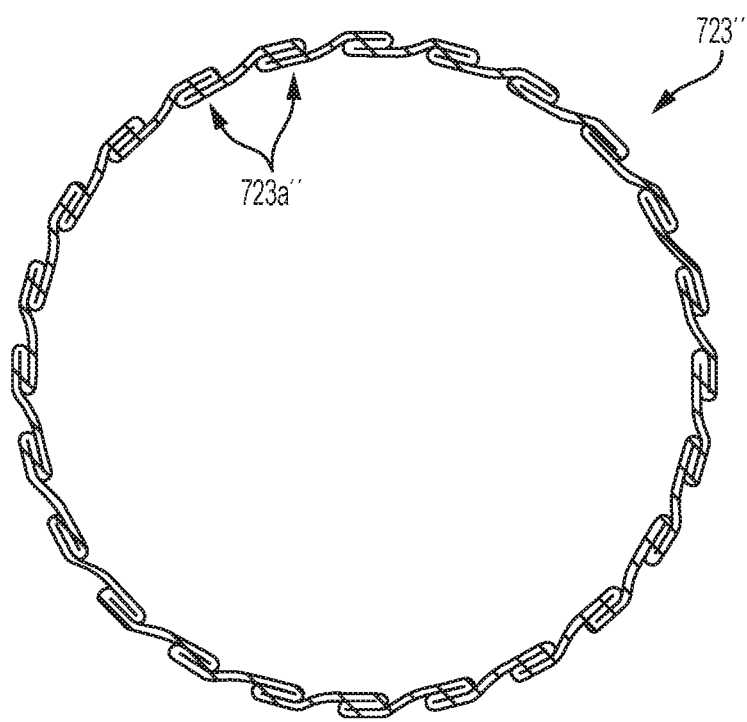
FIG. 27 is a cross-sectional top view of the safety shield of FIG. 26.
Figure 28:
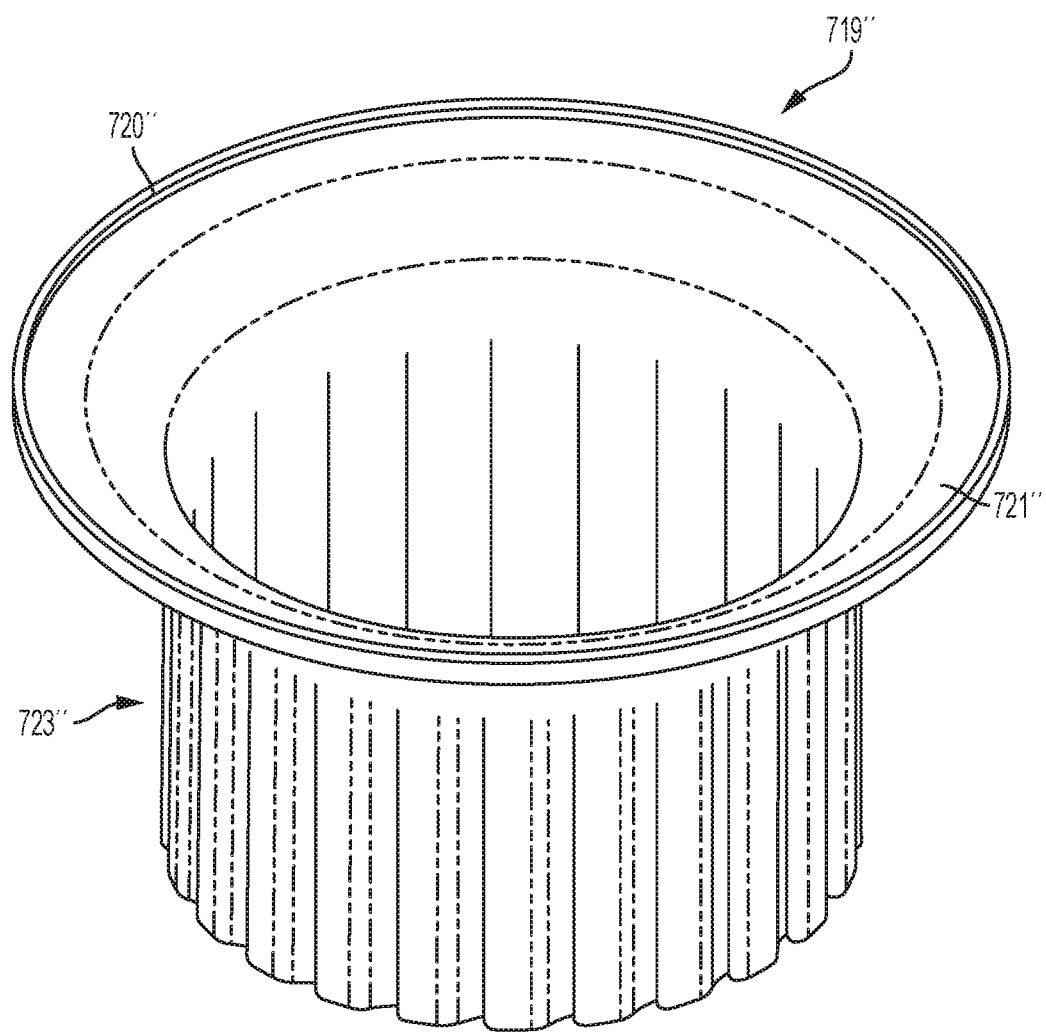
FIG. 28 is a perspective view of the safety shield of FIG. 26.

A shield can include a plurality of layers as discussed above, or a shield can be a singular member, which can make the shield easier to dispose in a retractor. FIGS. 24 and 25 illustrate one embodiment of a singular shield 719'. The alternate shield 719' can include a circumferential proximal rim 721' with or without radially extending flanges and with a lip 720' for mating with the device 10, as described above. Instead of having a plurality of fingers distally extending from the proximal rim 721', the alternate shield 719' can include a pleated distal portion 723' that simulates distal fingers. The pleated distal portion 723' can have a variety of sizes, shapes, and configurations. As shown, the pleated distal portion 723' can include a plurality of box pleats 723a' folded in the shield 719' circumferentially around the distal portion 723'. In this way, the pleated distal portion 723' can be configured to be selectively movable when the retractor 719' bends, if the retractor 719' is flexible, and/or when a surgical instrument presses against an inner wall of the pleated distal portion 723'. In another embodiment of a singular retractor shield 719", shown in FIGS. 26-28, the shield 719" can include a pleated distal portion 723" distally extending from a proximal rim 721" having a lip 720" and having a plurality of knife pleats 723a" formed circumferentially therearound. As will be appreciated, any type of shield can be used as needed in a particular application and can be interchanged before, during, and/or after a procedure as needed.

Other exemplary surgical access devices are also provided. In one embodiment shown in FIGS. 29A and 29B, a base member 200 of a housing for a surgical access device is provided having three sealing elements 202 attached or coupled to independently slidably rotatable rims 204a, 204b, 204c. As shown, the three slidably rotatable rims 204a, 204b, 204c are provided concentrically adjacent to one another near an outer circumference of the base member 200. The rotatable rims 204a, 204b, 204c can each have an elongate sealing element arm 205 extending radially therefrom. The rotatable rims 204a, 204b, 204c can be independently rotatable, thus allowing the sealing element arms 205 extending therefrom to be rotatable relative to the other sealing element arms 205 coupled to the other rims 204a, 204b, 204c. During use, a particular sealing element arm 205 can be rotated by a surgical instrument disposed therein, which causes the rim 204a, 204b, 204c to rotate relative to the other rims 204a, 204b, 204c. In this way, independent rotation of the sealing elements 202 relative to each other and relative to the base member 200 can be achieved.

Figure 29A:
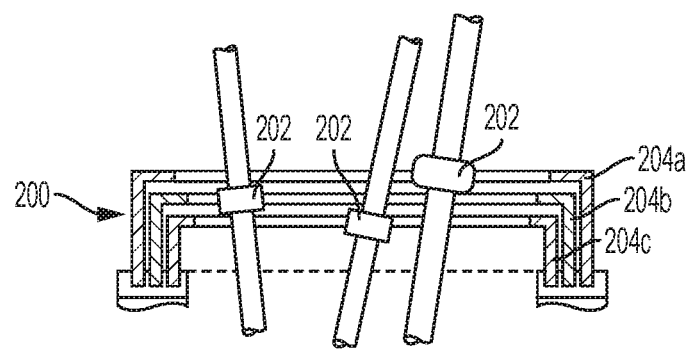
FIG. 29A is a cross-sectional view of another embodiment of a base member of a surgical access device having rotatable sealing elements.

In some embodiments, a flexible sealing member can form at least a center portion of the base member 200, and sealing membranes of each sealing element 202 can be integrally formed with the sealing member. The sealing membranes can be, for example, flexible, conically shaped elements that are configured to receive and form a seal around an instrument inserted therethrough. The sealing member can stretch, twist, bunch, and otherwise deform to allow movement of the sealing elements 202 around the base member 200 while maintaining a seal across a working channel of the access device. In addition to lateral, rotational movement of the sealing elements 202 around the circumference of the base member 200, the sealing elements 202 can also be moved angularly with respect to a central longitudinal axis of the base member 200, as shown in FIG. 29A, and vertically parallel to the central longitudinal axis of the base member. In some embodiments, the flexible sealing member can form just a center portion of the base member 200. In other embodiments, the flexible sealing member can form an entire layer of the base member 200.

Figure 29B:
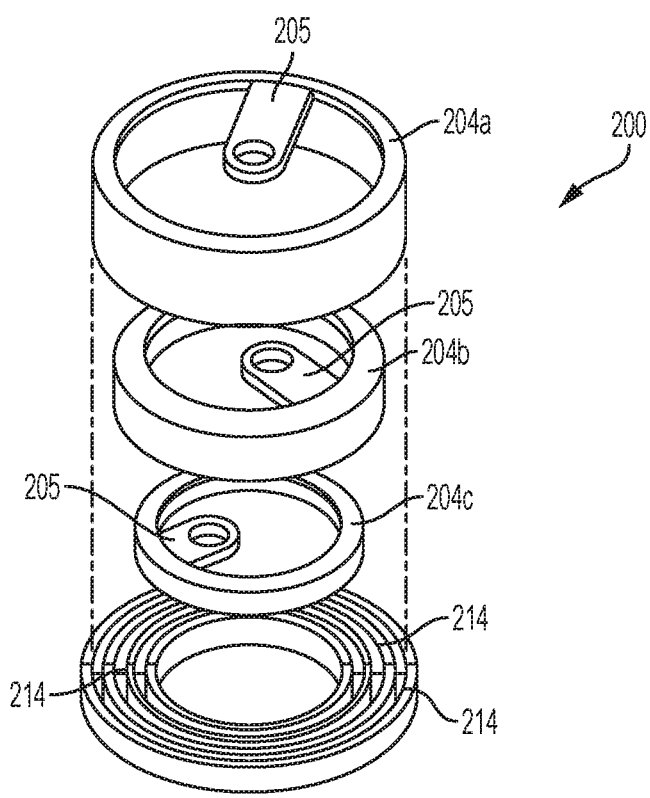
FIG. 29B is an exploded view of the base member of FIG. 29A illustrating rotatable rims for rotating the sealing elements.

An exemplary mechanism for accomplishing rotation of three independent rims is shown most clearly in FIG. 29B. As shown, three tracks or grooves 214 can be formed around an outer circumference of the base member 200 and can each receive a slidably rotatable rim 204a, 204b, 204c. Each rotatable rim 204a, 204b, 204c can move or slide within its groove 214 to accomplish rotation. Each sealing element 202 can be attached to one of the rotatable rims 204a, 204b, 204c and can thereby be rotated around the circumference of the base member 200. In other embodiments, each rim 204a, 204b, 204c can simply be positioned adjacent to one another such that the rims 204a, 204b, 204c are slidably rotatable relative to each other around the circumference of the base member 200. A person skilled in the art will appreciate the various methods of accomplishing rotation of the rims 204a, 204b, 204c.

Figure 30:
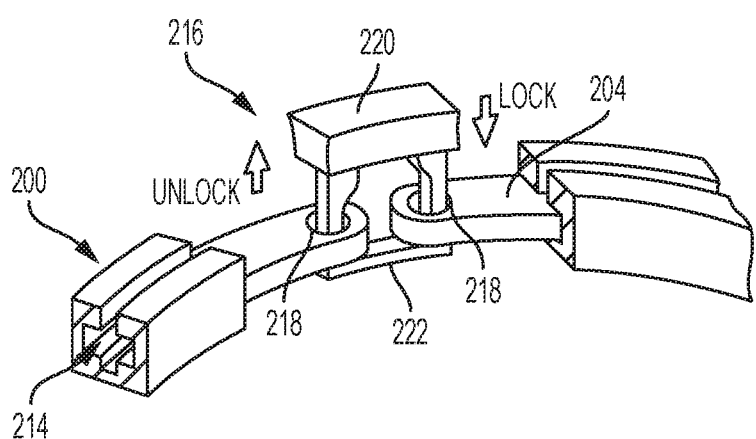
FIG. 30 is one embodiment of locking mechanism for preventing rotation of the rotatable rims of FIG. 29B.
Figure 31A:
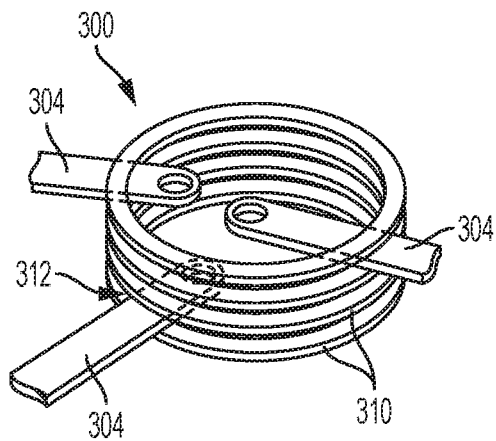
FIG. 31A is a perspective view of one embodiment of a base member with multiple rotatable rings.
Figure 31B:
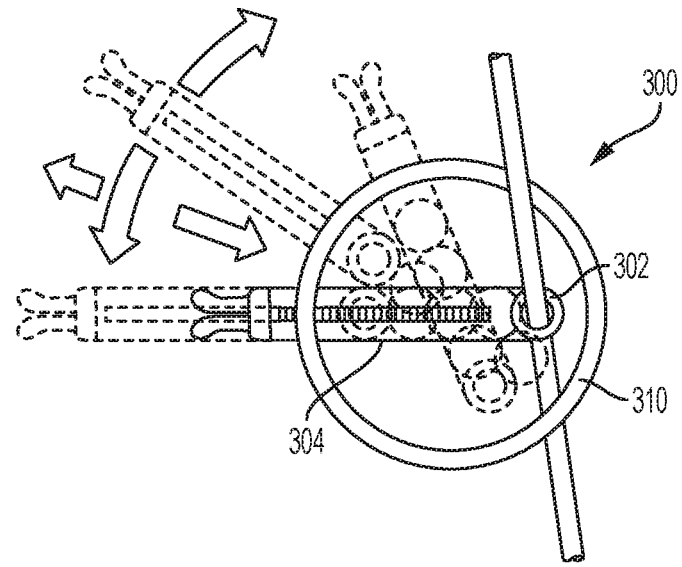
FIG. 31B is a top view of the base member of FIG. 31A showing movable flexible arms.
Figure 31C:
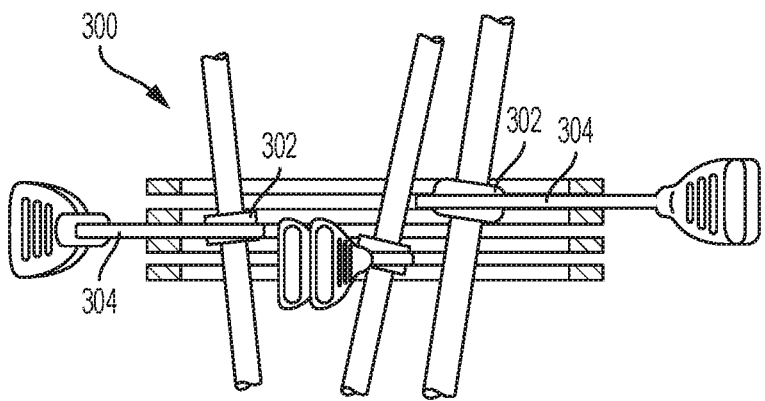
FIG. 31C is a cross-sectional view of the base member of FIG. 31A.
Figure 31D:
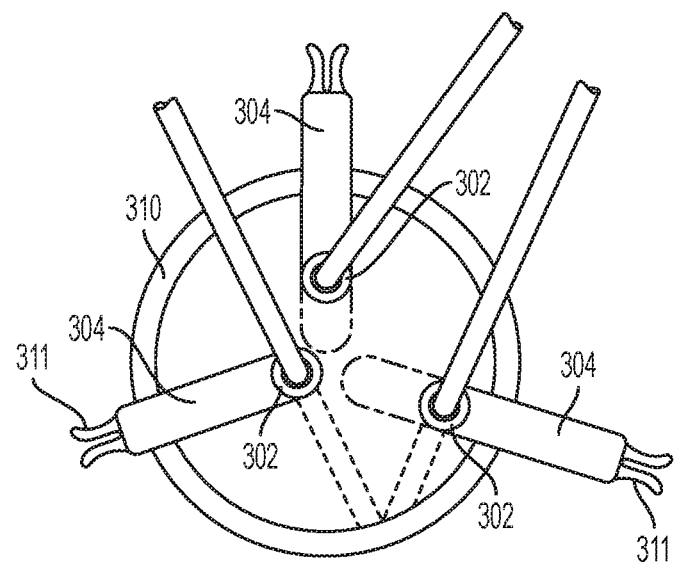
FIG. 31D is a top view of the base member of FIG. 31A.
Figure 31E:
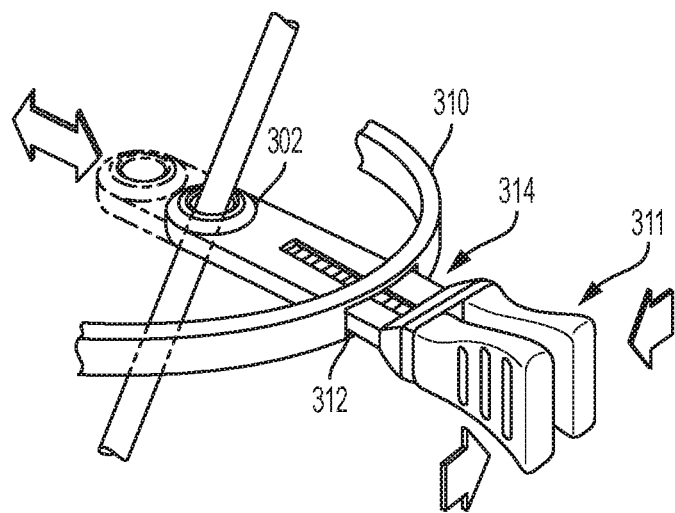
FIG. 31E is a perspective view of an adjustment mechanism of the base member of FIG. 31A.

An optional locking mechanism 216 is illustrated in FIG. 30 that can enable a position of the rotatable rims 204, and thereby the sealing elements 202, to be locked and/or secured. As shown, each rotatable rim 204 and each groove 214 can be divided into two portions. The end of each portion of the rotatable rim 204 can have an opening 218 formed therein for receiving a selectively movable latch 220 that joins the two sections together. When the latch 220 is up or disengaged, a bottom portion 222 of the latch 220 is raised to allow the rotatable rim 204 to be moved within its corresponding groove 214 and around the circumference of the base member 200. When the latch 220 is lowered or engaged, and when the latch 220 is within a space dividing the groove 214, the bottom portion 222 of the latch 220 is lower than the groove 214 and cannot be moved within the groove 214, thereby preventing movement of the rotatable rim 204.

Another exemplary embodiment of a base member 300 for a surgical access device is illustrated in FIGS. 31A-31E.

The base member 300 is similar to that described above in FIGS. 29A-29B, but includes an additional feature enabling adjustment of a radial length of an elongate member 304 of a sealing element 302 extending into a center of the base member 300. One or more slots 312 can be formed in each rotatable rim 310 to receive the elongate member 304 of the sealing element 302. An adjustment mechanism in the form of a flexible lever 314 can be inserted through the slots 312 in the rotatable rims 310 to thereby secure a radial length of the elongate member 304. In the unflexed position, the flexible lever 314 can engage sides of the slot 312 to prevent radial adjustment of the elongate member 304. By squeezing grips 311, a width of the flexible lever 314 can be decreased so that the radial length of the elongate member 304 can be adjusted. For example, the elongate member 304 of the sealing element 302 can be made longer by sliding the elongate member 304 inward within the slot 312 to thereby move the sealing element 302 further into a center portion of the base member 300. In other embodiments, the elongate member 304 of the sealing element 302 can be shortened by sliding the elongate member 304 outward within the slot 312 to thereby pull the sealing element 302 toward the outer circumference of the base member 300 and away from the center portion.

The sealing elements 302 can each be disposed through and/or formed integrally with a flexible sealing member, similar to those described above, which allows for the radius of each sealing element 302 to be adjusted. As the sealing elements 302 are each moved inward and/or outward relative to the outer circumference of the base member 300, the sealing member can bunches, stretches, twists, and otherwise deforms as needed to allow movement of the sealing element 302 while maintaining an air and gas tight seal across the working channel of the housing. In addition to radial length adjustments, the sealing elements 302 can also be independently rotated via the rotatable rims 310, as described above, and as also facilitated by the flexible sealing member. As with other embodiments, the sealing elements 302 can each be independently moved laterally, angularly, and vertically as needed due to the flexibility of the sealing member 320.

Figure 32A:
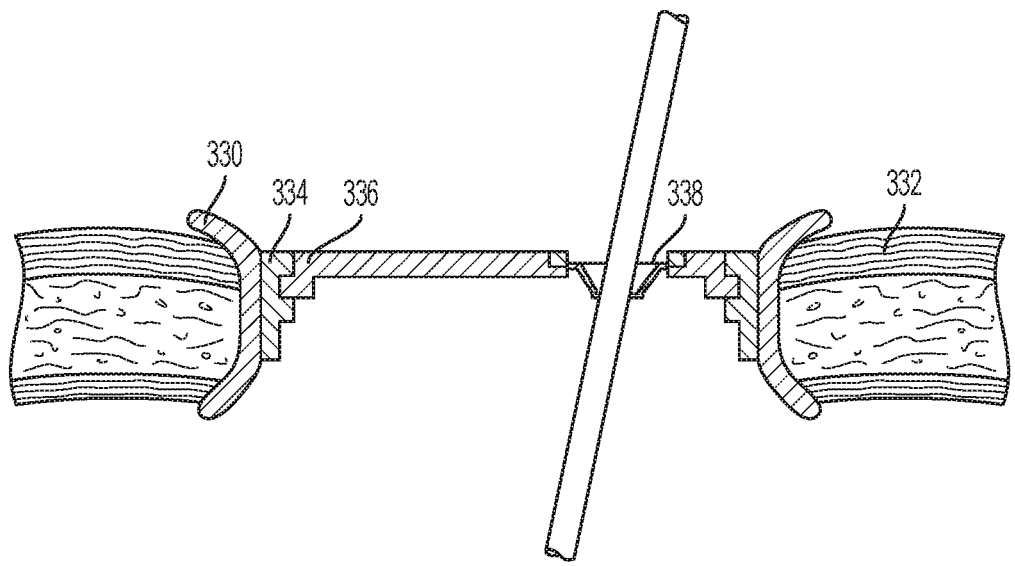
FIG. 32A is a cross-sectional view of a base member of a surgical access device having a flush sealing element.
Figure 32B:
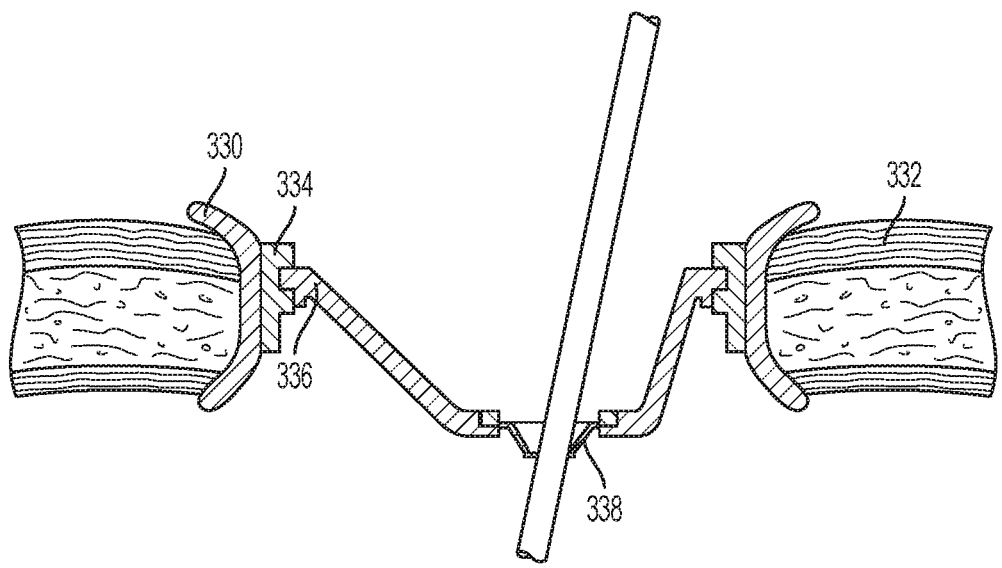
FIG. 32B is a cross-sectional view of a base member of a surgical access device having a recessed sealing element.

In another embodiment shown in FIGS. 32A and 32B, a flexible retractor 330 is positioned within tissue 332. A housing 334 is positioned within the retractor 330 and seats a rotatable base member 336 having a sealing element 338 formed therein. In some embodiments, the rotatable base member 336 can be generally flush with a top surface of the housing 334 as shown, for example, in FIG. 32A. In other embodiments, the base member 336 can extend distally at an angle with respect to the top surface of the housing 334 such that the sealing element 338 is in a recessed positioned relative to the top surface of the housing, as shown, for example, in FIG. 32B. As will be appreciated, the base member 336 can also have a semi-flexible or completely flexible sealing membrane to enable the sealing element 338 to be moved between a flush position and a recessed position.

Figure 33A:
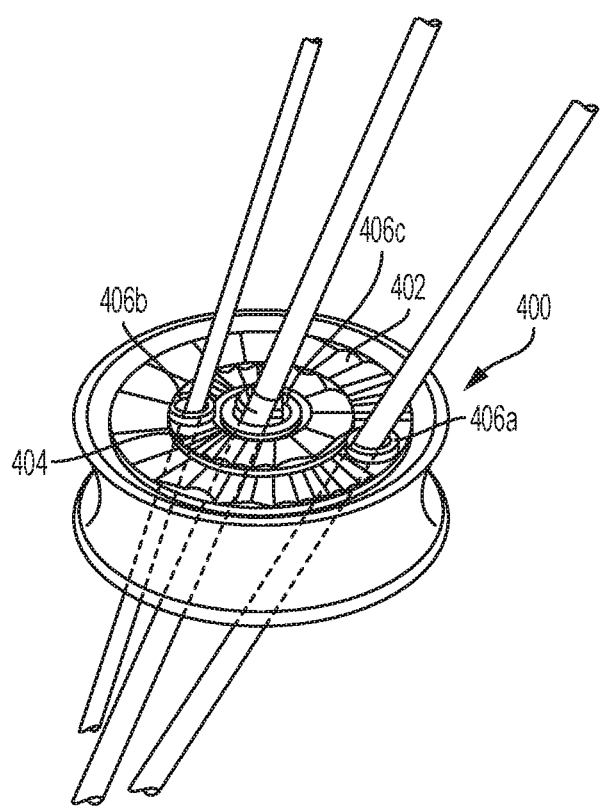
FIG. 33A is a perspective view of a base member having a flexible bellows sealing member.
Figure 33B:
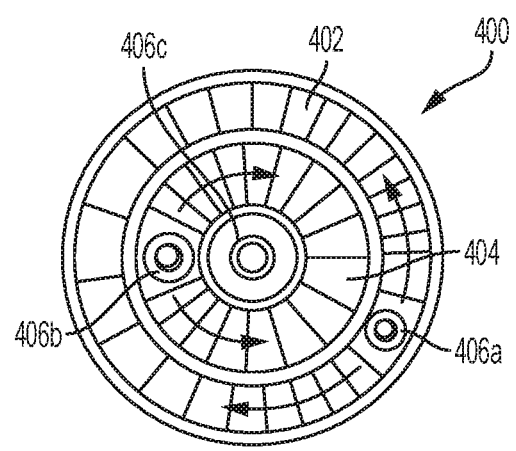
FIG. 33B is a top view of the base member of FIG. 33A.

Another exemplary embodiment of a base member 400 of a surgical access device is illustrated in FIGS. 33A and 33B. The base member 400 can include one or more rotatable pathways, for example two pathways 402, 404, extending around the base member 400 at different radii. One or more sealing elements, for example sealing elements 406a and 406b, can be disposed within each rotatable pathway 402, 404 and can be rotated 360 degrees around the base member 400 within their respective pathways 402, 404. Each pathway 402, 404 contains a flexible membrane, for example a flexible bellows, that can compress and expand in response to movement of the sealing elements 406a, 406b. Accordingly, as sealing elements 406a are moved along pathway 402, the flexible bellows or other flexible membrane can bunch and compress to allow independent movement of each sealing element 406a or 406b independent of the other. In some embodiments, a sealing element 406c can be positioned in a center portion of the base member 400.

Figure 34A:
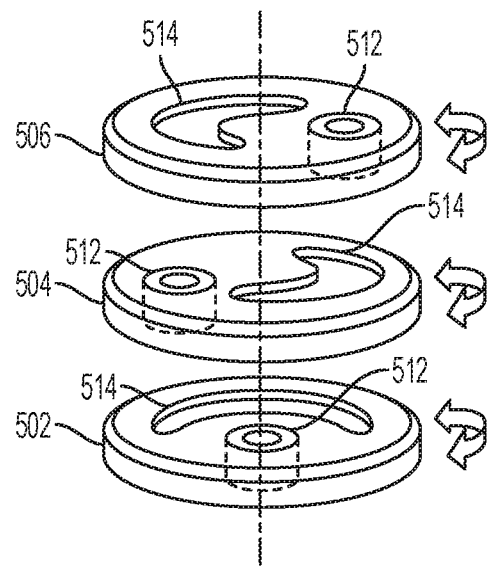
FIG. 34A is an exploded view of three rotatable base members having sealing elements therein.
Figure 34B:
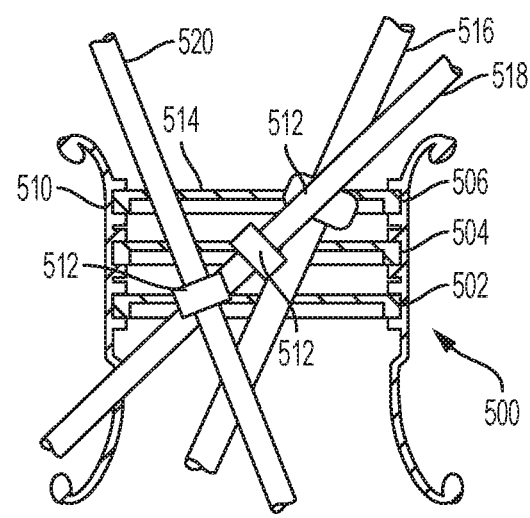
FIG. 34B is a cross-sectional view of the base members of FIG. 34A positioned in a housing.

Another exemplary embodiment of a surgical access device 500 is illustrated in FIGS. 34A and 34B. As shown, the surgical access device includes three base members 502, 504, 506 disposed within a housing 510. The three base members 502, 504, 506 are generally positioned vertically within the housing 510, one on top of another, and separated by a distance. In each base member 502, 504, 506, a sealing element 512, for example a gimbal type seal, is disposed therein and positioned, for example, on one side of each base member 502, 504, 506. A flexible sealing member 514 with various openings formed therein and having a substantially crescent or moon-like shape can be positioned on a side of the base members 502, 504, 506 opposite to the sealing element 512. In some embodiments, the sealing member 514 can be a slit seal having two thin, overlapping silicone or urethane pieces that allow a seal to be maintained between each of the three base members 502, 504, 506 when an instrument is passed therethrough. Each base member 502, 504, 506 can be disposed within the housing 510 in such a way that the sealing elements 512 and the sealing members 514 are slightly offset from one another. In addition, each base member 502, 504, 506 can be rotatable relative to the housing 510 to enable adjustment of their position relative to one another. As shown in FIG. 34B, the sealing elements 512 and sealing members 514 are offset so that a surgical instrument can be inserted through all three base members 502, 504, 506 and have a range of motion within its respective base member 502, 504, 506 relative to the other base members 502, 504, 506.

For example, a first surgical instrument 516 can be inserted into the sealing element 512 in the top or proximal most base member 506. The first surgical instrument 516 extends through the sealing element 512 and through the openings in the flexible sealing members 514 of the bottom two base members 502, 504. The first surgical instrument 516 is sealed within the sealing element 512 in the top base member 506 and can be moved laterally within the sealing members 514 of the bottom two base members 502, 504 to enable greater maneuverability. A second surgical instrument 518 can be inserted through the sealing member 514 of the top base member 506, into the sealing element 512 of the middle base member 504, and through the sealing member 514 of the bottom base member 502. Similar to the first surgical instrument 516, the second surgical instrument 518 can move laterally within the sealing members 514 of the top and bottom base members 506, 502 and is sealed within the sealing element 512 of the middle base member 504. Likewise, a third surgical instrument 520 can be inserted through the sealing members 514 of the top and middle base members 506, 504 and into the sealing element 512 of the bottom base member 502. The third surgical instrument 520 can be laterally movable relative to the top and middle base members 506, 504 and is sealed within the sealing element 512 formed in the bottom base member 502. In this way, each surgical instrument 516, 518, 520 has a greater range of maneuverability within the surgical access device 500.

Figure 35A:
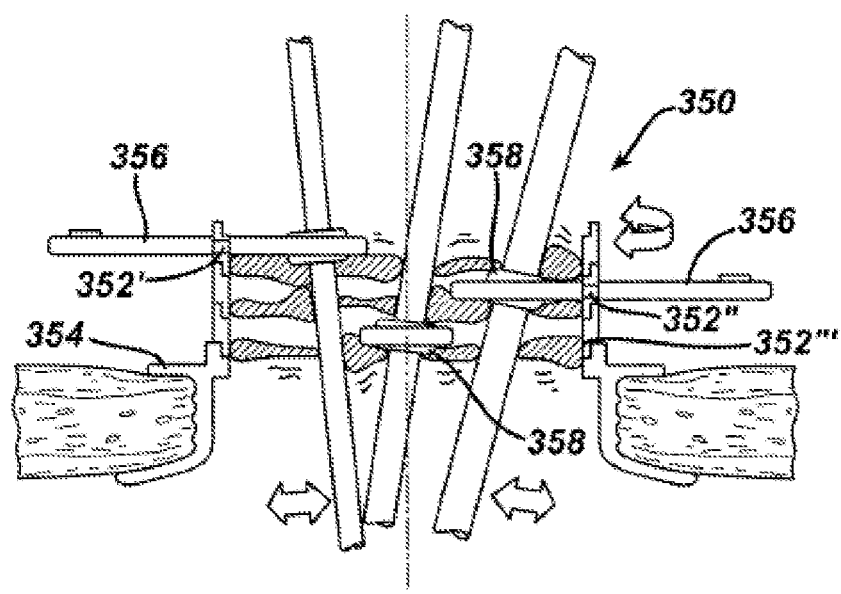
FIG. 35A is a cross-sectional view of an exemplary base member having multiple layers of sealing elements.
Figure 35B:
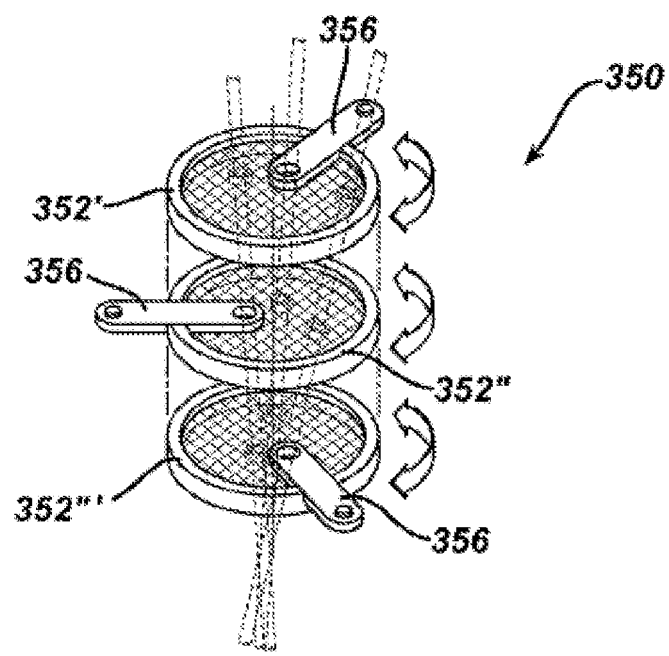
FIG. 35B is a perspective view of the base member of FIG. 35A.

Another embodiment is shown in FIGS. 35A and 35B. A base member 350 is provided having a plurality of rotatable rings 352 that can be positioned on top of a base member support 354. Each ring 352', 352", 352'" can include a movable arm 356 having a sealing element 358 disposed therein. The arm 356 can be radially adjustable to move the sealing element 358 between an outer circumference of the base member 350 and a center portion of the base member 350 by any mechanism known in the art. For example, a simple press fit or interference fit can exist between the arm 356 and the rings 352', 352", 352'" such that the arm can be held in place using friction and can be manually moved relative to the rings 352', 352", 352'" as needed. In addition, the sealing elements 358 can be movable angularly relative to the movable arm 356 to allow angular movement of a surgical instrument disposed therethrough. A flexible seal member 360', 360", 360'" can form the a center portion of each ring 352', 352", 352'" and can bunch, stretch, and deform to allow the sealing elements 358 to move with the surgical instruments.

Figure 36A:
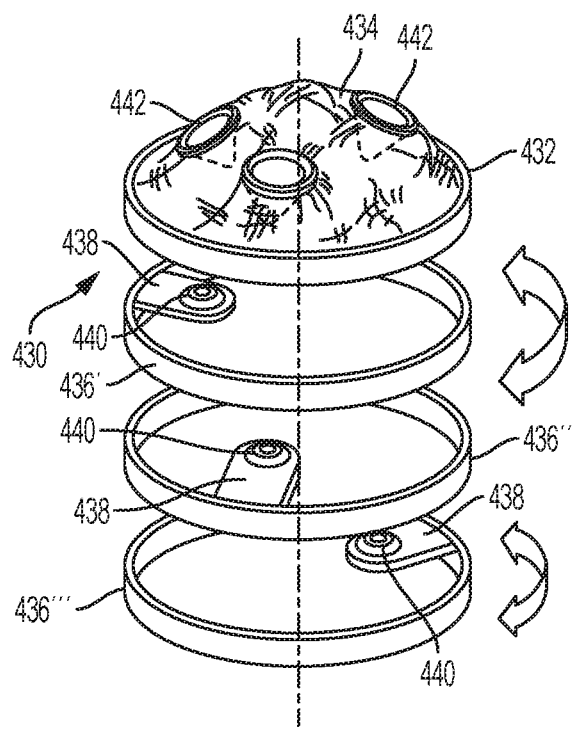
FIG. 36A is an exploded view of a base member having a flexible sealing membrane and a plurality of rotatable rims.
Figure 36B:
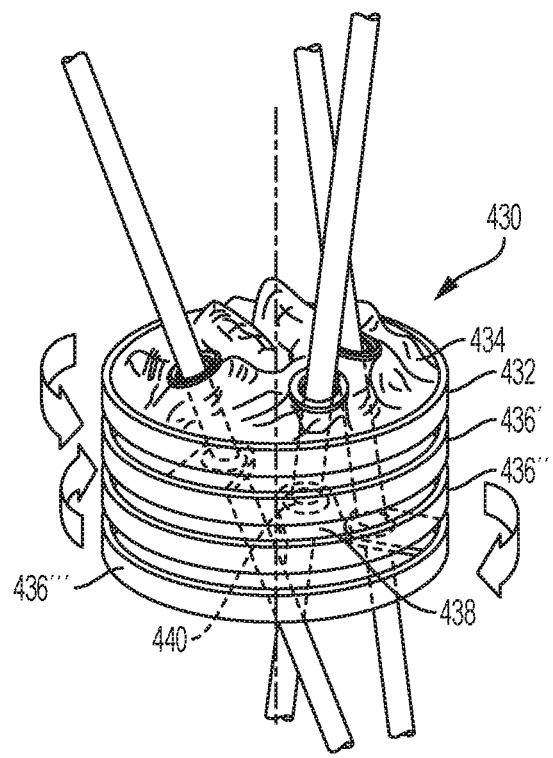
FIG. 36B is a perspective view of the base member of FIG. 36A.
Figure 37A:
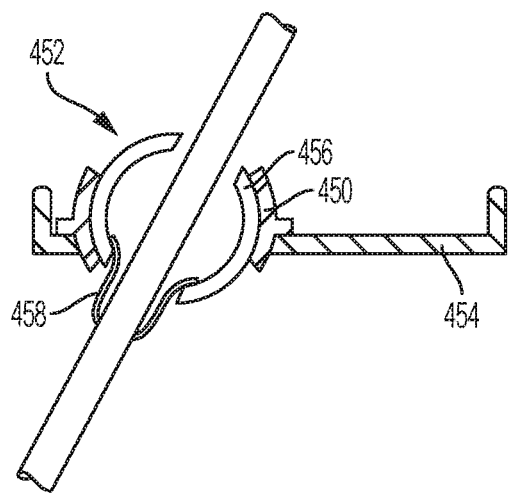
FIG. 37A is a cross-sectional view of a gimbal seal.
Figure 37B:
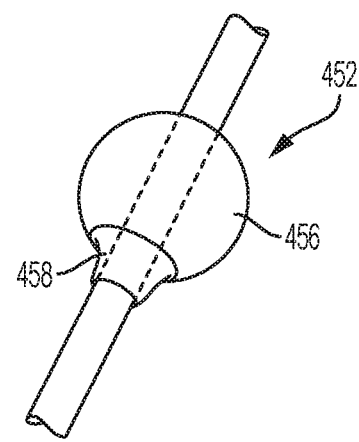
FIG. 37B is a perspective of the gimbal seal of FIG. 37A having an instrument positioned therein.
Figure 37C:
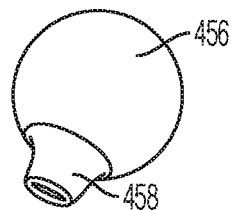
FIG. 37C is a perspective of the gimbal seal of FIG. 37A.
Figure 37D:
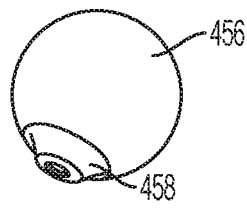
FIG. 37D is another perspective view of the gimbal seal of FIG. 37A.

In a further embodiment shown in FIGS. 36A and 36B, a base member 430 is provided having a plurality of rotatable rings. A top rotatable ring 432 can contain a flexible sealing member 434, similar to the flexible membranes described herein. In addition, in some embodiments, the sealing member 434 can include one or more sealing elements 442 disposed therethrough that can be integrally formed with the flexible sealing member 434. One or more other rotatable rings 436, for example, three rings 436', 436", 436'" each can have sealing arms 438 extending therefrom and can be stacked one on top of the other beneath the sealing member 434. Each ring 436 can be individually rotatable relative to the other rings 436', 436", 436" and relative to the sealing member 434. Each of the sealing arms 438 can include a sealing element 440 positioned at one end thereof and configured to form a seal around an instrument inserted therethrough. In use, for example, an instrument can be inserted through the sealing element 442 in the sealing member 434, and into one of the sealing elements 440 in one of the rings 436. The instrument can be used to rotate each ring 436 as needed in a procedure, and the sealing member can flex, stretch, and bunch to allow the instrument to move while still maintaining a seal around the instrument.

Figure 39A:
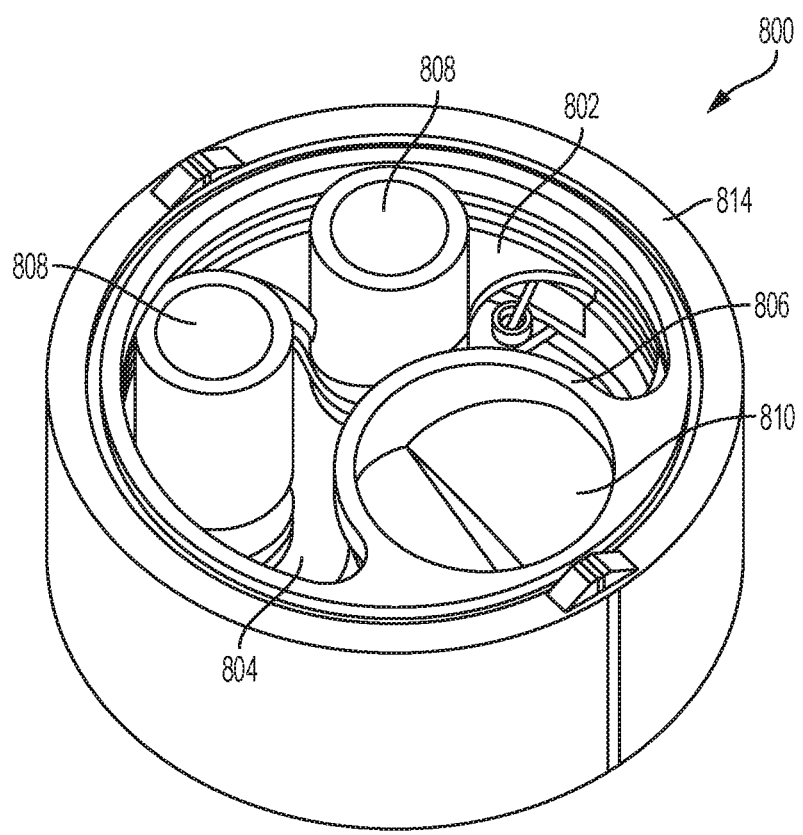
FIG. 39A is a top view of another embodiment of a base member having rotatable rims.
Figure 39B:
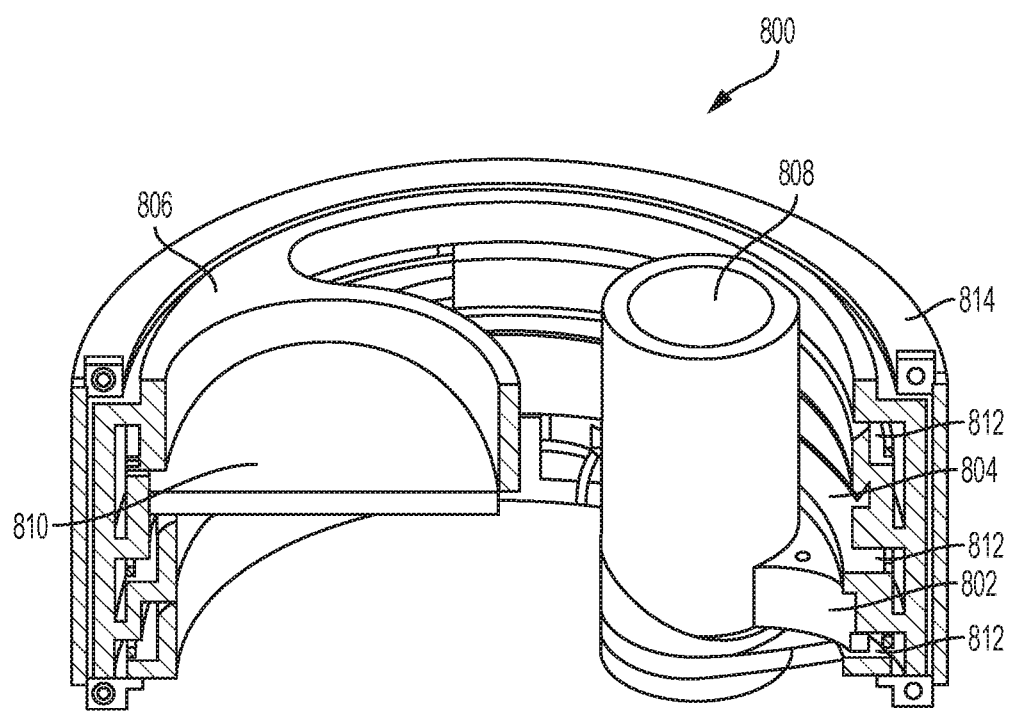
FIG. 39B is a cross-sectional view of the base member of FIG. 39A.

Another exemplary embodiment of a surgical access device 800 is shown in FIGS. 39A-39B. The surgical access device 800 can have a housing 814 with one or more, for example three, triangular-shaped base members 802, 804, 806 stacked one on top of another. Each base member 802, 804, 806 can have at least one sealing element 808 and one or more, for example two, slit seals 810 disposed therein. Similar to the embodiment illustrated in FIGS. 34A and 34B, surgical instruments can be inserted through the sealing element 808 in one base member 802, 804, 806 and can extend through the slit seals 810 in the other two base members to allow movement of the instrument within the sealing element 808 relative to the other base members while a seal is maintained. In addition, tracks 812 extending around the circumference of each base member 802, 804, 806 allows the base members 802, 804, 806 to be rotatable relative to each other and relative to the housing 814.

In any of the embodiments described herein, any type of seal known in the art can be used to form a seal around a surgical instrument and/or to seal a channel of the sealing element such that a seal is formed when no instrument is inserted therethrough. Conical seals, such as those shown in FIGS. 5 and 6, can be used to form a seal around an instrument and are simply composed of conically shaped flexible membrane have an opening at an apex of the cone. In some embodiments, a gimbal seal, such as that shown in FIGS. 37A-37D, can be used. A gimbal seal can include a frame 450 that connects a sealing element 452 to a base member 454. The sealing element 452 can include a gimbal 456 and a sealing membrane 458 extending from the gimbal 456. The gimbal 456 can rotate and move in all directions within the frame 450 to allow a full range of movement for a surgical instrument inserted through the sealing element 452. The sealing membrane 458 can form a seal around an instrument inserted therethough and generally does not form a seal when no instrument is inserted therethrough.

In other embodiments, sealing elements can take the form of a multi-layer conical instrument seal. The multi-layer conical seal can generally include a series of overlapping seal segments that are assembled in a woven arrangement to provide a complete seal body. A protective member can be positioned adjacent to the multi-layer conical seal to protect the seal from sharp instruments being inserted therethrough. The multi-layer conical seal and/or the protector can be formed of elastomeric materials and/or from a molded thermoplastic polyurethane elastomer, such as Pellethane™. Exemplary instrument seal configurations are described in more detail in U.S. Publication No. 2004/0230161 entitled "Trocar Seal Assembly," filed on Mar. 31, 2004, and U.S. application Ser. No. 10/687,502 entitled "Conical Trocar Seal," filed on Oct. 15, 2003, which are hereby incorporated by reference in their entireties.

Another type of sealing element that can be used in the surgical access devices described herein is the channel or zero-closure seal. The zero-closure seal can be, for example, in the form of a duckbill seal that is configured to form a seal in a working channel when no instrument is disposed therethrough to thus prevent the leakage of insufflation gases delivered through the surgical access device to the body cavity. The duckbill seal can generally have opposed flaps that extend at an angle toward one another in a distal direction and that come together at a distal end to form a seal face. The opposed flaps can be movable relative to one another to allow the seal face to move between a closed position, in which no instrument is disposed therethrough and the seal face seals the working channel of the surgical access device, and an open position in which an instrument is disposed therethrough. The seal can include various other features, as described in more detail in U.S. application Ser. No. 11/771,263, entitled "Duckbill Seal with Fluid Drainage Feature," filed on Jun. 29, 2007, which is hereby incorporated by reference in its entirety. In addition, the seal face of the duckbill seal can be in any nonlinear shape or configuration known in the art, for example in an S-shaped configuration, as described in more detail in U.S. Pat. No. 5,330,437, entitled "Self Sealing Flexible Elastomeric Valve and Trocar Assembly for Incorporating Same," filed Nov. 12, 1993, which is hereby incorporated by reference in its entirety.

In accordance with the present disclosure, the general structure of the seals do not generally form part of the present invention. As such, a person skilled in the art will certainly appreciate that any and all sealing elements and sealing configurations known in the art can be used within the surgical access device embodiments disclosed herein without departing from the spirit of the invention disclosed.

As will also be appreciated by those skilled in the art, any and all of the base members embodiments disclosed herein can be interchangeable with one another as needed. For example, an exemplary surgical access device kit could include multiple housings and base members with one or more retractors. Each base member and housing combination can have different pathway and/or track configurations enabling various combinations of sealing element movement as needed in particular application. Various release mechanisms known in the art can be used to releasably attach the various base members and housings to a retractor.

As surgical instruments are inserted through the surgical access device embodiments described herein, a risk can exist that a particularly sharp instrument may tear or puncture a portion of the retractor or nearby tissue. Accordingly, in any and all of the embodiments described herein, a safety shield can optionally be included to reduce the risk of tearing or puncture by a surgical instrument. In general the shield can be of a material that is relatively smooth to allow ease of passage of instruments, but resistant to tearing and puncture. For example, the shield can formed of silicone, urethane, thermoplastic elastomer, rubber, polyolefins, polyesters, nylons, fluoropolymers, and any other suitable materials known in the art. The shield can generally provide a liner for a retractor or tissue and can be detachable from a surgical access device so it can be used as needed in a particular procedure.

There are various features that can optionally be included with any and all of the surgical access device embodiments disclosed herein. For example, a component of the device, such as a base member, housing, retractor, etc., can have one or more lights formed thereon or around a circumference thereof to enable better visualization when inserted within a patient. As will be appreciated, any wavelength of light can be used for various applications, whether visible or invisible. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. application Ser. No. 12/242,333 entitled "Methods and Devices for Performing Gastrectomies and Gastroplasties" filed on Sep. 30, 2008; U.S. application Ser. No. 12/242,353 entitled "Methods and Devices for Performing Gastrectomies and Gastroplasties" filed on Sep. 30, 2008; and U.S. application Ser. No. 12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a sealing element, sealing member, base member, a housing, a retractor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). In addition, individual components of the devices described herein can be sterilized separately. For example, a surgical access device of the invention can be deconstructed into its individual component pieces, such as the housing cover, the housing support, the base member support, and/or the various components of the base member, and each can be sterilized using any of the above described techniques.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a housing including a first predefined elongate path formed therein and including a second predefined elongate path formed therein, and the housing being configured to have first and second surgical instruments extending therethrough such that a distal portion of each of the first and second surgical instruments is located in a body of a patient and a proximal portion of each of the first and second surgical instruments is located outside of the body of the patient;
a first support that seats a first sealing element, the first sealing element being configured to receive the first surgical instrument therethrough and form a seal therearound, and the first sealing element being configured to move, with the first surgical instrument received therethrough, within the first predefined elongate path relative to the housing;
a second support that seats a second sealing element, the second sealing element being configured to receive the second surgical instrument therethrough and form a seal therearound, and the second sealing element being configured to move, with the second surgical instrument received therethrough, within the second predefined elongate path relative to the housing; and a deformable membrane coupled to the housing, the deformable membrane being configured to deform in response to the movement of the first sealing element within the first predefined elongate path;

wherein the deformable membrane includes a first opening therein that is in communication with the first predefined elongate path such that the first surgical instrument extending through the first predefined elongate path also extends through the first opening; and the deformable membrane includes a second opening therein that is in communication with the second predefined elongate path such that the second surgical instrument extending through the second predefined elongate path also extends through the second opening.

2. The device of claim 1, wherein the deformable membrane is configured to deform in response to the movement of the second sealing element within the second predefined elongate path.

3. The device of claim 1, wherein the first support connects the first sealing element to the housing;

the first sealing element includes a first gimbal;

the second support connects the second sealing element to the housing; and the second sealing element includes a second gimbal.

4. The device of claim 1, wherein the first sealing element is configured to rotate in all directions relative to the first support; and the second sealing element is configured to rotate in all directions relative to the second support.

5. The device of claim 1, wherein the first support connects the first sealing element to the housing;

the first support includes a first rigid ring seating the first sealing element therein;

the second support connects the second sealing element to the housing; and the second support includes a second rigid ring seating the second sealing element therein.

6. The device of claim 1, wherein the first predefined elongate path extends circumferentially, and the second predefined elongate path extends circumferentially.

7. The device of claim 1, further comprising a third support that seats a third sealing element, the third sealing element being configured to receive a third surgical instrument therethrough and form a seal therearound, and the third sealing element being configured to move, with the third surgical instrument received therethrough, relative to the housing.

8. A surgical device, comprising:

a housing including a first predefined elongate path formed therein and including a second predefined elongate path formed therein, and the housing being configured to have first and second surgical instruments extending therethrough such that a distal portion of each of the first and second surgical instruments is located in a body of a patient and a proximal portion of each of the first and second surgical instruments is located outside of the body of the patient;

a first support that seats a first sealing element, the first sealing element being configured to receive the first surgical instrument therethrough and form a seal therearound, and the first sealing element being configured to move, with the first surgical instrument received therethrough, within the first predefined elongate path relative to the housing;

a second support that seats a second sealing element, the second sealing element being configured to receive the second surgical instrument therethrough and form a seal therearound, and the second sealing element being configured to move, with the second surgical instrument received therethrough, within the second predefined elongate path relative to the housing; and a deformable membrane coupled to the housing, the deformable membrane being configured to deform in response to the movement of the first sealing element within the first predefined elongate path;

wherein the first predefined elongate path extends radially, includes a first terminal end at a position adjacent to an outer diameter of the housing, and includes a second terminal end radially inward of the first terminal end; and the second predefined elongate path extends radially, includes a third terminal end at a position adjacent to the outer diameter of the housing, and includes a fourth terminal end radially inward of the third terminal end.

9. The device of claim 8, wherein the deformable membrane includes a first opening therein that is in communication with the first predefined elongate path such that the first surgical instrument extending through the first predefined elongate path also extends through the first opening; and the deformable membrane includes a second opening therein that is in communication with the second predefined elongate path such that the second surgical instrument extending through the second predefined elongate path also extends through the second opening.

10. The device of claim 8, wherein the deformable membrane is configured to deform in response to the movement of the second sealing element within the second predefined elongate path.

11. The device of claim 8, further comprising a third support that seats a third sealing element, the third sealing element being configured to receive a third surgical instrument therethrough and form a seal therearound, and the third sealing element being configured to move, with the third surgical instrument received therethrough, relative to the housing.

12. A surgical method, comprising:

moving a first sealing element within a first predefined elongate path formed in a housing of a surgical device, the movement of the first sealing element being relative to the housing and causing deformation of a deformable membrane of the surgical device, the first sealing element being seated in a first support of the surgical device, and the first sealing element having a first surgical instrument inserted therethrough and forming a seal around the first surgical instrument; and moving a second sealing element within a second predefined elongate path formed in the housing, the movement of the second sealing element being relative to the housing, the second sealing element being seated in a second support of the surgical device, and the second sealing element having a second surgical instrument inserted therethrough and forming a seal around the second surgical instrument;

wherein the first predefined elongate path extends radially, includes a first terminal end at a position adjacent to an outer diameter of the housing, and includes a second terminal end radially inward of the first terminal end; and the second predefined elongate path extends radially, includes a third terminal end at a position adjacent to the outer diameter of the housing, and includes a fourth terminal end radially inward of the third terminal end.

13. The method of claim 12, wherein the first sealing element includes a first gimbal;
- the method further comprises rotating the first gimbal relative to the first support and the housing;
- the second sealing element includes a second gimbal; and
- the method further comprises rotating the second gimbal relative to the second support and the housing.

14. The method of claim 12, wherein the first support connects the first sealing element to the housing;
- the first support includes a first rigid ring seating the first sealing element therein;
- the second support connects the second sealing element to the housing; and
- the second support includes a second rigid ring seating the second sealing element therein.

15. The method of claim 12, wherein the first predefined elongate path extends circumferentially, and the second predefined elongate path extends circumferentially.

16. The method of claim 12, further comprising moving a third sealing element of the surgical device relative to the housing, the third sealing element being seated in a third support of the surgical device, and the third sealing element having a third surgical instrument inserted therethrough and forming a seal around the third surgical instrument.

17. The method of claim 12, further comprising advancing the first surgical instrument through the first sealing element and through a working channel of a retractor of the surgical device to position a distal portion of the first surgical instrument within a body of a patient, the retractor being positioned within an opening in skin of the patient; and
- advancing the second surgical instrument through the second sealing element and through the working channel to position a distal portion of the second surgical instrument within the body of the patient.

18. The method of claim 17, wherein the movement of the first sealing element and the movement of the second sealing element each occur with the first surgical instrument extending through the first sealing element and the working channel and with the second surgical instrument extending through the second sealing element and the working channel.

\* \* \* \* \*